US006916798B2

(12) United States Patent
Green et al.

(10) Patent No.: US 6,916,798 B2
(45) Date of Patent: Jul. 12, 2005

(54) INHIBITORS OF GSK-3 AND USES THEREOF

(75) Inventors: Jeremy Green, Burlington, MA (US); Michael J. Arnost, North Andover, MA (US); Albert Pierce, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 79 days.

(21) Appl. No.: 10/212,471

(22) Filed: Aug. 2, 2002

(65) Prior Publication Data

US 2004/0024040 A1 Feb. 5, 2004

Related U.S. Application Data

(60) Provisional application No. 60/309,838, filed on Aug. 3, 2001.

(51) Int. Cl.$^7$ ................. A61K 31/4152; A61K 31/655; C07D 231/08; C07D 231/20; C07D 401/02
(52) U.S. Cl. ....................... 514/150; 514/407; 534/753; 534/769; 534/774; 534/775; 548/364.1; 548/364.4; 548/364.7; 548/365.1; 548/365.7
(58) Field of Search ................................ 534/753, 769, 534/774, 775; 548/364.1, 364.4, 364.7, 365.1, 365.7; 514/150, 407

(56) References Cited

U.S. PATENT DOCUMENTS

| | | | | |
|---|---|---|---|---|
| 2,908,677 | A | * 10/1959 | Straley et al. | ............... 534/710 |
| 4,666,933 | A | 5/1987 | Jelich et al. | ................. 514/404 |
| 4,743,615 | A | 5/1988 | Jelich et al. | ................. 514/404 |
| 4,968,687 | A | 11/1990 | Findeisen et al. | ........... 514/269 |
| 4,968,714 | A | 11/1990 | Lunkenheimer et al. | .... 514/404 |
| 4,988,718 | A | 1/1991 | Findeisen et al. | ........... 514/363 |

FOREIGN PATENT DOCUMENTS

| | | | |
|---|---|---|---|
| EP | 1072597 | * | 1/2001 |
| JP | 47-49167 | * | 12/1972 |
| WO | WO-01/09121 | * | 2/2001 |
| WO | WO-01/32653 | * | 5/2001 |

OTHER PUBLICATIONS

Sueda et al., Chemical Abstracts, 80:38356, 1974.*
Etman et al., J. Indian Chem. Soc., 67, 213–215, 1990.*
Junek et al., Chemical Abstracts, 110:153632, 1989.*
Ledrut et al., Chemical Abstracts, 70:37708, 1969.*
Mancy et al., Chemical Abstracts, 122:265785, 1995.*
Mustafa et al., Chemical Abstracts, 69:2800, 1968.*
Prakash et al., Chemical Abstracts, 66:55436, 1967.*
Saharia et al., Chemical Abstracts, 81:105390, 1974.*
Sekily et al., Carbohydrate Research, 112, 151–157, 1983.*
Abass et al., Synthetic Communications, 31(21), 3361–3376, 2001.*
Al–Hajjar, Chemical Abstracts, 88:136510, 1978.*
Baig et al., J. Chem. Soc., Perkin Transactions 1, 8, 1811–1819, 1982.*
Elnagdi et al., Chemical Abstracts, 77:152053, 1972.*
Abass, et al., "Chemistry of Substituted Quinolinones. III", Synthesis and Reactions of Some Novel 3–Pyrazolyl–2–Quinolinones, *Synthetic Communications*, 31(21):3361–3376, 2001.
Hafez, et al., "New Heterocyclo–Substituted Pyrazolo[3, 4–b]Pyridine Derivatives", *Collect. Czech. Chem. Commun.* 58: 1198–1202, 1993.
Keats, et al., "Mass Spectral Fragmentation Pattern of 5–Methyl–4–[Phenylamino)Methylene]2, 4–Dihydro–3H–Pyrazol–3–One and Its 2–Methyl and 2–Phenyl Derivatives", *J. Heterocyclic Chem.*, 19: 55–59, 1982.

* cited by examiner

*Primary Examiner*—Fiona T. Powers
(74) *Attorney, Agent, or Firm*—Andrea L.C. Robidoux; Choate, Hall & Stewart LLP

(57) ABSTRACT

The present invention relates to compounds of formula I that are useful as GSK-3 inhibitors. The invention also relates to methods of using compounds of formula I or pharmaceutical compositions comprising compounds of formula I to inhibit GSK-3 activity. The invention further provides methods of utilizing these compounds and pharmaceutical compositions in the treatment and prevention of various disorders, such as diabetes and Alzheimer's disease. The invention also relates to methods for inhibiting Aurora-2 activity and for treating or preventing Aurora-2-mediated diseases using compounds of formula I or pharmaceutical compositions comprising compounds of formula I. The invention also relates to methods for inhibiting cyclin-dependent kinase-2 activity and for treating or preventing inhibiting cyclin-dependent kinase-2-mediated diseases using compounds of formula I or pharmaceutical compositions comprising compounds of formula I.

10 Claims, No Drawings

INHIBITORS OF GSK-3 AND USES THEREOF

CROSS REFERENCE TO RELATED APPLICATIONS

This application claims priority to U.S. Provisional Patent Application 60/309,838, filed Aug. 3, 2001, the contents of which is incorporated by reference.

TECHNICAL FIELD OF INVENTION

The present invention relates to inhibitors of glycogen synthase kinase-3 (GSK-3), a serine/threonine protein kinase. The invention provides methods of using these compounds or pharmaceutical compositions comprising these compounds to inhibit GSK-3 activity. The invention further provides methods of utilizing these compounds or pharmaceutical compositions in the treatment and prevention of various disorders, such as diabetes and Alzheimer's disease. The invention also relates to methods for inhibiting Aurora-2 protein kinase or cyclin-dependent kinase-2, using these compounds or pharmaceutical compositions.

BACKGROUND OF THE INVENTION

The search for new therapeutic agents has been greatly aided in recent years by a better understanding of the structure of enzymes and other biomolecules associated with target diseases. One important class of enzymes that has been the subject of extensive study is protein kinases.

Protein kinases mediate intracellular signal transduction. They do this by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor $\alpha$ (TNF-$\alpha$)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis and regulation of cell cycle.

Many disease states are associated with abnormal cellular responses triggered by protein kinase-mediated events. These diseases include autoimmune diseases, inflammatory diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents. A challenge has been to find protein kinase inhibitors that act in a selective manner. Since there are numerous protein kinases that are involved in a variety of cellular responses, non-selective inhibitors may lead to unwanted side effects.

Glycogen synthase kinase-3 (GSK-3) is a serine/threonine protein kinase comprised of $\alpha$ and $\beta$ isoforms that are each encoded by distinct genes [Coghlan et al., *Chemistry & Biology*, 7, 793–803 (2000); and Kim and Kimmel, *Curr. Opinion Genetics Dev.*, 10, 508–514 (2000)]. GSK-3 has been implicated in various diseases including diabetes, Alzheimer's disease, CNS disorders such as manic depressive disorder and neurodegenerative diseases, and cardiomyocete hypertrophy [see, e.g., WO 99/65897; WO 00/38675; and Haq et al., *J. Cell Biol.* (2000) 151, 117]. These diseases may be caused by, or may result in, the abnormal operation of certain cell signaling pathways in which GSK-3 plays a role.

GSK-3 has been found to phosphorylate and modulate the activity of a number of regulatory proteins. These include glycogen synthase, which is the rate-limiting enzyme required for glycogen synthesis, the microtubule-associated protein Tau, the gene transcription factor $\beta$-catenin, the translation initiation factor e1F-2B, as well as ATP citrate lyase, axin, heat shock factor-1, c-Jun, c-myc, c-myb, CREB, and CEPB$\alpha$. These diverse targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. GSK-3 is a negative regulator of the insulin-induced signal in this pathway. Normally, the presence of insulin causes inhibition of GSK-3-mediated phosphorylation and deactivation of glycogen synthase. The inhibition of GSK-3 leads to increased glycogen synthesis and glucose uptake [Klein et al., *PNAS*, 93, 8455–9 (1996); Cross et al., *Biochem. J.*, 303, 21–26 (1994); Cohen, *Biochem. Soc. Trans.*, 21, 555–567 (1993); and Massillon et al., *Biochem J.* 299, 123–128 (1994)]. However, where the insulin response is impaired in a diabetic patient, glycogen synthesis and glucose uptake fail to increase despite the presence of relatively high blood levels of insulin. This leads to abnormally high blood levels of glucose with acute and chronic effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [WO 00/38675]. Therapeutic inhibitors of GSK-3 are therefore potentially useful for treating diabetic patients suffering from an impaired response to insulin.

GSK-3 activity has also been associated with Alzheimer's disease. This disease is characterized by the presence of the well-known $\beta$-amyloid peptide and the formation of intracellular neurofibrillary tangles. The neurofibrillary tangles contain hyperphosphorylated Tau protein, in which Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., *Current Biology* 4, 1077–86 (1994); and Brownlees et al., *Neuroreport* 8, 3251–55 (1997)]. Therefore, it is believed that GSK-3 activity may promote generation of neurofibrillary tangles and progression of Alzheimer's disease.

Another substrate of GSK-3 is $\beta$-catenin, which is degradated after phosphorylation by GSK-3. Reduced levels of $\beta$-catenin have been reported in schizophrenic patients and have also been associated with other diseases related to increase in neuronal cell death [Zhong et al., *Nature*, 395, 698–702 (1998); Takashima et al., *PNAS*, 90, 7789–93 (1993); Pei et al., *J. Neuropathol. Exp*, 56, 70–78 (1997); and Smith et al., *Bio-org. Med. Chem.* 11, 635–639 (2001)].

Small molecule inhibitors of GSK-3 have recently been reported [WO 99/65897 (Chiron) and WO 00/38675 (SmithKline Beecham)]; however, there is a continued need to find new therapeutic agents to treat human diseases. The protein kinase GSK-3, in particular GSK-3$\beta$, is an especially attractive target for the discovery of new therapeutics due to its important role in diabetes, Alzheimer's disease and other diseases.

Aurora-2 is another serine/threonine protein kinase that has been implicated in human cancer, such as colon, breast and other solid tumors. This kinase is believed to be involved in protein phosphorylation events that regulate the cell cycle. Specifically, Aurora-2 may play a role in controlling the accurate segregation of chromosomes during mitosis. Misregulation of the cell cycle can lead to cellular proliferation and other abnormalities. In human colon cancer tissue, the Aurora-2 protein has been found to be overexpressed [Bischoff et al., *EMBO J.*, 17, 3052–3065 (1998); Schumacher et al., *J. Cell Biol.*, 143, 1635–1646 (1998); and Kimura et al., *J. Biol. Chem.*, 272, 13766–13771 (1997)].

Cyclin-dependent kinases (CDKs) inhibitors have been described as anticancer agents [Fischer, P. M. and Lane, D. P., *Current Medicinal Chemistry*, 7, 1213–1245 (2000); Mani, S., Wang, C., Wu, K., Francis, R. and Pestell, R., *Exp. Opin. Invest. Drugs*, 9, 1849 (2000); and Fry, D. W. and Garrett, M. D., *Current Opinion in Oncologic, Endocrine & Metabolic Investigational Drugs*, 2, 40–59 (2000)]. Although some CDK-2 inhibitors have been disclosed, it would be desirable to have other CDK-2 inhibitors for treating human diseases.

Therefore, there is a need to inhibit protein kinases, particularly glycogen synthase kinases, Aurora and cyclin-dependent kinases, more particularly GSK-3, Aurora-2 and CDK-2, for treatment of human diseases.

SUMMARY OF THE INVENTION

The present invention provides methods for effectively inhibiting protein kinases, particularly glycogen synthase kinases, Aurora and cyclin-dependent kinases, and more particularly GSK-3, Aurora-2 and CDK-2, utilizing compounds and pharmaceutical compositions described herein. These compounds have the general formula I:

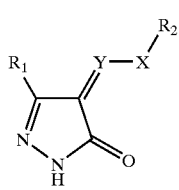

I or a pharmaceutically acceptable derivative or prodrug thereof, wherein:

$R_1$ is selected from H; alkyl; carbocyclyl; heterocyclyl; aryl; heteroaryl; —CN; —C(O)R; —CO$_2$R; or —CON(R)$_2$; wherein said alkyl, carbocyclyl, or heterocyclyl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, —NRS(O)$_2$R, =O, =S, =NN(R)$_2$, =N—OR, =NN(R)COR, =NNRCO$_2$R, =NNRSO$_2$R, =N—CN, or =NR; and wherein said aryl or heteroaryl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, or —NRS(O)$_2$R;

$R_2$ is selected from H; alkyl; carbocyclyl; heterocyclyl; aryl; or heteroaryl; wherein said alkyl, carbocyclyl, or heterocyclyl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, —NRS(O)$_2$R, =O, =S, =NN(R)$_2$, =N—OR, =NN(R)COR, =NNRCO$_2$R, =NNRSO$_2$R, =N—CN, or =NR; and wherein said aryl or heteroaryl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, or —NRS(O)$_2$R;

X is O, S or —NH;

Y is N or CH;

each R is independently selected from H; alkyl; carbocyclyl; heterocyclyl; aryl; heteroaryl; or any two R groups taken together form a carbocyclyl, heterocyclyl, aryl or heteroaryl group; wherein said alkyl, carbocyclyl, or heterocyclyl is optionally substituted with one to four substituents independently selected from halo, —R', —OR', —SR', —NO$_2$, —CN, —N(R')$_2$, —NR'C(O)R', —NR'C(O)N(R')$_2$, —N(R')CO$_2$R', —CO$_2$R', —C(O)R', —C(O)N(R')$_2$, —S(O)$_2$R', —S(O)$_2$N(R')$_2$, —S(O)R', —N(R')S(O)$_2$R', =O, =S, =NN(R')$_2$, =N—OR', =NN(R')COR', =NN(R')CO$_2$R', =NN(R')SO$_2$R', =N—CN, or =NR'; and wherein said aryl or heteroaryl is optionally substituted with one to four substituents independently selected from halo, —R', —OR', —SR', —NO$_2$, —CN, —N(R')$_2$, —NR'C(O)R', —NR'C(O)N(R')$_2$, —N(R')CO$_2$R', —CO$_2$R', —C(O)R', —C(O)N(R')$_2$, —S(O)$_2$R', —S(O)$_2$N(R')$_2$, —S(O)R', or —N(R')S(O)$_2$R';

each R' is independently selected from H; alkyl; carbocyclyl; heterocyclyl; aryl; heteroaryl; or any two R' groups taken together form a carbocyclyl, heterocyclyl, aryl or heteroaryl group; wherein said alkyl, carbocyclyl, or heterocyclyl is optionally substituted with one to four substituents independently selected from halo, CF$_3$, —R", —OR", —SR", —NO$_2$, —CN, —N(R")$_2$, —NR"C(O)R", —NR"C(O)N(R")$_2$, —N(R")CO$_2$R", —CO$_2$R", —C(O)R", —C(O)N(R")$_2$, —S(O)$_2$R", —S(O)$_2$N(R")$_2$, —S(O)R", —N(R")S(O)$_2$R", =O, =S, =NN(R")$_2$, =N—OR", =NN (R")COR", =NN(R")CO$_2$R", =NN(R")SO$_2$R", =N—CN, or =NR"; and wherein said aryl or heteroaryl is optionally substituted with one to four substituents independently selected from halo, CF$_3$, —R", —OR", —SR—, —NO$_2$, —CN, —N(R")$_2$, —NR"C(O)R", —NR"C(O)N(R")$_2$, —N(R")CO$_2$R", —CO$_2$R", —C(O)R", —C(O)N(R")$_2$, —S(O)$_2$R", —S(O)$_2$N(R")$_2$, —S(O)R", or —N(R")S(O)$_2$R"; and each R" is independently selected from H or alkyl.

In one embodiment, the invention provides compositions comprising compounds of formula I. The compounds and compositions of the present invention may be utilized in methods for treating or preventing a variety of GSK-3 mediated disorders, such as autoimmune diseases, inflammatory diseases, metabolic, neurological and neurodegenerative diseases, cardiovasclular diseases, allergy, asthma, diabetes, Alzheimer's disease, Huntington's Disease, Parkinson's Disease, AIDS-associated dementia, amyotrophic lateral sclerosis (AML, Lou Gehrig's Disease), multiple sclerosis (MS), schizophrenia, cardiomyocyte hypertrophy, reperfusion/ischemia, and baldness.

The compounds and compositions of this invention are also useful in methods for enhancing glycogen synthesis and/or lowering blood levels of glucose and therefore are especially useful for diabetic patients. These compounds and compositions are also useful in methods for inhibiting the production of hyperphosphorylated Tau protein, which is useful in halting or slowing the progression of Alzheimer's disease. Another embodiment of this invention relates to a method for inhibiting the phosphorylation of β-catenin, which is useful for treating schizophrenia.

In another embodiment, the invention provides methods for preparing pharmaceutical compositions comprising compounds of formula I.

In yet another embodiment, the invention provides methods for effectively inhibiting Aurora-2 activity and for treating or preventing Aurora-2-mediated conditions utilizing compounds of formula I and pharmaceutical compositions thereof.

In another embodiment, the invention provides methods for effectively inhibiting CDK-2 activity and for treating or preventing CDK-2-mediated conditions utilizing compounds of formula I and pharmaceutical compositions thereof.

DETAILED DESCRIPTION OF THE INVENTION

The following abbreviations are used throughout the specifications (including in chemical formulae):

iPr=isopropyl
t-Bu or tBu=tert-butyl
Et=ethyl
Me=methyl
Cbz=benzyloxycarbonyl
DEAD=diethyl azodicarboxylate
Ph=phenyl
Bn=benzyl
DMF=N,N-dimethylformamide THF=tetrahydrofuran
DCM=dichloromethane
dba=dibenzylidene-acetone
BINAP=2,2'-bis(diphenylphosphino)-1,1'-binaphthyl
DMSO=dimethylsulfoxide
HPLC=high pressure liquid chromatography As used herein, the following definitions shall apply unless otherwise indicated. Also, combinations of substituents or variables are permissible only if such combinations result in stable compounds.

The term "alkyl" as used herein, alone or in combination with any other term, refers to straight chain or branched $C_1$–$C_{12}$ hydrocarbons that are completely saturated or that contain one or more units of unsaturation. The term "alkyl" includes hydrocarbons that contain at least one carbon-carbon double bond (i.e., alkenyl) or at least one carbon-carbon triple bond (i.e., alkynyl). Preferably, alkyl radicals contain one to six carbon atoms. Examples of alkyl radicals include, but are not limited to, methyl, ethyl, n-propyl, isopropyl, n-butyl, i-butyl, t-butyl, pentyl, isoamyl, n-hexyl, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z-hexadienyl, ethynyl, propynyl, 1-butynyl, 2-butynyl, 1-pentynyl, 2-pentynyl and the like. The term "alkoxy" refers to —O-alkyl.

The term "carbocylyl" or "carbocyclic", alone or in combination with any other term, refers to monocyclic or polycyclic non-aromatic hydrocarbon ring systems, which may contain a specified number of carbon atoms, preferably from 3 to 14 carbon atoms, which are completely saturated or which contain one or more units of unsaturation. A carbocyclic ring system may be monocyclic, bicyclic or tricyclic. A carbocylyl ring may be fused to another ring, such as an aryl ring or another carbocyclic ring, where the radical or point of attachment is on the carbocylyl ring. Five- to seven-membered monocyclic and nine- to eleven-membered bicyclic carbocyclic ring systems are preferred. Examples of carbocyclic rings include cyclohexyl, cyclopentyl, cyclobutyl, cyclopropyl, cyclohexenyl, cyclopentenyl, indanyl, tetrahydronaphthyl and the like. The term "carbocyclic" or "carbocylyl" also encompasses hybrids of alkyl and carbocyclic groups, such as (cycloalkyl) alkyl.

The term "halogen" or "halo" means F, Cl, Br, or I.

The term "heteroatom" means N, O, or S and shall include any oxidized form of nitrogen and sulfur, such as N(O), S(O), S(O)$_2$ and the quaternized form of any basic nitrogen.

The term "heterocyclic" or "heterocyclyl" refers to non-aromatic saturated or unsaturated monocyclic or polycyclic ring systems containing one or more heteroatoms and with a ring size of three to fourteen. One having ordinary skill in the art will recognize that the maximum number of heteroatoms in a stable, chemically feasible heterocyclic ring is determined by the size of the ring, degree of unsaturation, and valence. In general, a heterocyclic ring may have one to four heteroatoms so long as the heterocyclic ring is chemically feasible and stable and may be fused to another ring, such as a carbocyclic, aryl or heteroaryl ring, or to another heterocyclic ring. A heterocyclic ring system may be monocyclic, bicyclic or tricyclic. Five- to seven-membered monocyclic and nine- to eleven-membered bicyclic heterocyclic ring systems are preferred. The term "heterocyclylalkyl" refers to an alkyl group substituted by a heterocyclyl. Also included within the scope of the term "heterocyclic" or "heterocyclyl", as used herein, are radicals wherein one or more carbocyclic rings are fused to a heteroaryl.

Examples of heterocyclic rings include, but are not limited to, 3-1H-benzimidazol-2-one, 3-1H-alkyl-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxane, benzotriazol-1-yl, benzopyrrolidine, benzopiperidine, benzoxolane, benzothiolane, benzothiane, aziranyl, oxiranyl, azetidinyl, pyrrolinyl, dioxolanyl, imidazolinyl, imidazolidinyl, pyrazolinyl, pyrazolidinyl, pyranyl, dioxanyl, dithianyl, trithianyl, quinuclidinyl, oxepanyl, and thiepanyl.

The term "aryl", alone or in combination with other terms, refers to monocyclic or polycyclic aromatic carbon ring systems having five to fourteen members. Five- to seven-membered monocyclic and nine- to eleven-membered bicyclic aryl ring systems are preferred. Examples of aryl groups include, but are not limited to, phenyl (Ph), 1-naphthyl, 2-naphthyl, 1-anthracyl and 2-anthracyl. Also included within the scope of the term "1aryl", as it is used herein, is a group in which an aryl is fused to one or more aryl or carbocyclic rings, such as in an indanyl, phenanthridinyl, or tetrahydronaphthyl, where the radical or point of attachment is on the aryl. The term "aralkyl" refers to an alkyl group substituted by an aryl. Examples of aralkyl groups include, but are not limited to, benzyl and phenethyl.

The term "heteroaryl", alone or in combination with any other term, refers to monocyclic or polycyclic heterocyclic aromatic ring systems having five to fourteen members. One having ordinary skill in the art will recognize that the maximum number of heteroatoms in a stable, chemically feasible hetearoaryl ring is determined by the size of the ring and valence. Five- to seven-membered monocyclic and nine- to eleven-membered bicyclic heteroaryl ring systems are preferred. The term "heteroaralkyl" refers to an alkyl group substituted by a heteroaryl. In general, a heteroaryl ring may have one to four heteroatoms. Heteroaryl groups include, without limitation, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, and 3-thienyl.

Also included within the scope of the term "heteroaryl", as used herein, are radicals wherein one or more heteroaryl rings are fused to a heteroaryl, an aryl, a carbocyclic or a heterocyclic ring, where the radical or point of attachment is on the heteroaryl. Examples of such fused polycyclic heteroaryl ring systems include, benzimidazolyl, benzothienyl, benzofuranyl, indolyl, quinolinyl, benzothiazolyl, benzoxazolyl, benzimidazolyl, isoquinolinyl, isoindolyl, acridinyl, benzoisoxazolyl, tetrahydroquinolinyl, tetrahydroisoquinolinyl, and pyrido[3,4-d]pyrimidinyl and the like.

Guided by this specification, the selection of suitable substituents of radicals defined herein is within the knowledge of one skilled in the art.

A substitutable nitrogen on a heteroaryl or a non-aromatic heterocyclic ring is optionally substituted. Suitable substituents on the nitrogen include $R^0$, $COR^0$, $S(O)_2R^0$, $S(O)_2$-aryl such as phenyl, and $CO_2R^0$, wherein $R^0$ is H or alkyl.

The term "chemically feasible or stable", as used herein, refers to a compound structure that is sufficiently stable to allow manufacture and administration to a patient by methods known in the art. Typically, such compounds are stable at a temperature of 40° C. or less, in the absence of moisture or other chemically reactive conditions, for at least one week.

One object of the instant invention is to provide compounds having formula (I):

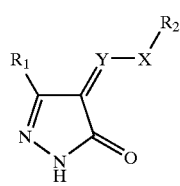

I or a pharmaceutically acceptable derivative or prodrug thereof, wherein:

$R_1$ is selected from H; alkyl; carbocyclyl; heterocyclyl; aryl; heteroaryl; —CN; —C(O)R; —$CO_2R$; or —$CON(R)_2$; wherein said alkyl, carbocyclyl, or heterocyclyl is optionally substituted with one to four substituents independently selected from halo, —R, —OR, —SR, —$NO_2$, —CN, —$N(R)_2$, —NRC(O)R, —NRC(O)N(R)$_2$, —$NRCO_2R$, —$CO_2R$, —C(O)R, —C(O)N(R)$_2$, —S(O)$_2$R, —S(O)$_2$N(R)$_2$, —S(O)R, —NRS(O)$_2$R, =O, =S, =NN(R)$_2$, =N-OR, =NN(R)COR, =NNRCO$_2$R, =NNRSO$_2$R, =N—CN, or =NR; and wherein said aryl or heteroaryl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, or —NRS(O)$_2$R;

$R_2$ is selected from H; alkyl; carbocyclyl; heterocyclyl; aryl; or heteroaryl; wherein said alkyl, carbocyclyl, or heterocyclyl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, —NRS(O)$_2$R, =O, =S, =NN(R)$_2$, =N—OR, =NN(R)COR, =NNRCO$_2$R, =NNRSO$_2$R, =N—CN, or =NR; and wherein said aryl or heteroaryl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, or —NRS(O)$_2$R;

X is O, S or —NH;

Y is N or CH;

each R is independently selected from H; alkyl; carbocyclyl; heterocyclyl; aryl; heteroaryl; or any two R groups taken together form a carbocyclyl, heterocyclyl, aryl or heteroaryl group; wherein said alkyl, carbocyclyl, or heterocyclyl is optionally substituted with one to four substituents independently selected from halo, —R', —OR', —SR', —NO$_2$, —CN, —N(R')$_2$, —NR'C(O)R—, —NR'C(O)N(R')$_2$, —N(R')CO$_2$R', —CO$_2$R', —C(O)R', —C(O)N(R')$_2$, —S(O)$_2$R', —S(O)$_2$N(R')$_2$, —S(O)R', —N(R')S(O)$_2$R', =O, =S, =NN(R')$_2$, =N—OR', =NN(R')COR', =NN(R')CO$_2$R', =NN(R')SO$_2$R', =N—CN, or =NR'; and wherein said aryl or heteroaryl is optionally substituted with one to four substituents independently selected from halo, —R', —OR', —SR', —NO$_2$, —CN, —N(R')$_2$, —NR'C(O)R', —NR'C(O)N(R')$_2$, —N(R')CO$_2$R', —CO$_2$R', —C(O)R', —C(O)N(R')$_2$, —S(O)$_2$R', —S(O)$_2$N(R')$_2$, —S(O)R', or —N(R')S(O)$_2$R';

each R' is independently selected from H; alkyl; carbocyclyl; heterocyclyl; aryl; heteroaryl; or any two R' groups taken together form a carbocyclyl, heterocyclyl, aryl or heteroaryl group; wherein said alkyl, carbocyclyl, or heterocyclyl is optionally substituted with one to four substituents independently selected from halo, CF$_3$, —R", —OR", —SR", —NO$_2$, —CN, —N (R")$_2$, —NR"C(O)R", —NR"C(O)N(R")$_2$, —N (R")CO$_2$R", —CO$_2$R", —C(O)R", C(O)N(R")$_2$, —S(O)$_2$R", —S(O)$_2$N(R")$_2$, —S(O)R", —N(R")S(O)$_2$R", =O, S, =NN(R")$_2$, =N—OR", =NN(R")COR", =NN(R")CO$_2$R", =NN(R")SO$_2$R", =N—CN, or =NR"; and wherein said aryl or heteroaryl is optionally substituted with one to four substituents independently selected from halo, CF$_3$, —R", —OR", —SR", —NO$_2$, —CN, —N (R")$_2$, —NR"C(O) R", —NR"C(O)N(R")$_2$, —N(R")CO$_2$R", —CO$_2$R", —C(O)R", —C(O)N(R")$_2$, —S(O)$_2$R", —S(O)$_2$N (R")$_2$, —S(O)R", or —N(R")S(O)$_2$R"; and each R" is independently selected from H or alkyl.

It will be apparent to one skilled in the art that certain compounds of this invention may exist in tautomeric forms, all such tautomeric forms of the compounds being within the scope of the invention. For example, a tautomeric form of compounds of formula I is shown in formula II wherein Y is N.

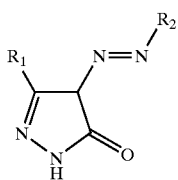

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

Certain preferred compounds of the present invention are those having the formula I:

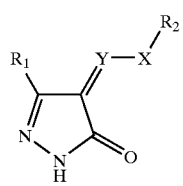

wherein:

$R_1$ is selected from H; alkyl; carbocyclyl; heterocyclyl; aryl; heteroaryl; —CN; —C(O)R; —CO$_2$R; or —CON(R)$_2$; wherein said alkyl, carbocyclyl, or heterocyclyl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, —NRS(O)$_2$R, =O, =S, =NN(R)$_2$, =N—OR, =NN(R)COR, =NNRCO$_2$R, =NNRSO$_2$R, =N—CN, or =NR; and wherein said aryl or heteroaryl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, or —NRS(O)$_2$R;

$R_2$ is selected from H; alkyl; carbocyclyl; heterocyclyl; aryl; or heteroaryl; wherein said alkyl, carbocyclyl, or heterocyclyl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, —NRS(O)$_2$R, =O, =S, =NN(R)$_2$, =N—OR, =NN(R)COR, =NNRCO$_2$R, =NNRSO$_2$R, =N—CN, or =NR; and wherein said aryl or heteroaryl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, or —NRS(O)$_2$R;

X is O, S or —NH;

Y is CH;

each R is independently selected from H; alkyl; carbocyclyl; heterocyclyl; aryl; heteroaryl; or any two R groups taken together form a carbocyclyl, heterocyclyl, aryl or heteroaryl group; wherein said alkyl, carbocyclyl, or heterocyclyl is optionally substituted with one to four substituents independently selected from halo, —R', —OR', —SR', —NO$_2$, —CN, —N(R')$_2$, —NR'C(O)R', —NR"C(O)N(R')$_2$, —N(R')CO$_2$R', —CO$_2$R', —C(O)R', —C(O)N(R')$_2$, —S(O)$_2$', —S(O)$_2$N(R')$_2$, —S(O)R', —N(R')S(O)$_2$ R', =O, =S, =NN(R')$_2$, =N—OR', =NN(R')COR', =NN(R')CO$_2$R', =NN(R')SO$_2$R', =N—CN, or =NR'; and wherein said aryl or heteroaryl is optionally substituted with one to four substituents independently selected from halo, —R', —OR', —SR', —NO$_2$, —CN, —N(R')$_2$, —NR'C(O)R', —NR'C(O)N(R')$_2$, —N(R')CO$_2$R', —CO$_2$R', —C(O)R', —C(O)N(R')$_2$, —S(O)$_2$R', —S(O)$_2$ N(R')$_2$, —S(O)R', or —N(R')S(O)$_2$R';

each R' is independently selected from H; alkyl; carbocyclyl; heterocyclyl; aryl; heteroaryl; or any two R' groups taken together form a carbocyclyl, heterocyclyl, aryl or heteroaryl group; wherein said alkyl, carbocyclyl, or heterocyclyl is optionally substituted with one to four substituents independently selected from halo, CF$_3$, —R", —OR", —SR", —NO$_2$, —CN, —N(R")$_2$, —NR"C(O)R", —NR"C(O)N(R")$_2$, —N(R")CO$_2$R", —CO$_2$R", —C(O)R", —C(O)N(R")$_2$, —S(O)$_2$R", —S(O)$_2$N(R")$_2$, —S(O)R", —N(R")S(O)$_2$R", =O, =S, =NN(R")$_2$, =N—OR", =NN(R")COR", =NN(R")CO$_2$R", =NN(R")SO$_2$R", =N—CN, or =NR"; and wherein said aryl or heteroaryl is optionally substituted with one to four substituents independently selected from halo, CF$_3$, —R", —OR", —SR", —NO$_2$, —CN, —N (R")$_2$, —NR"C(O)R", —NR"C(O)N(R")$_2$, —N(R")CO$_2$R", —CO$_2$R", —C(O)R", —C(O)N(R")$_2$, —S(O)$_2$R", —S(O)$_2$N(R")$_2$, —S(O)R", or —N(R")S(O)$_2$R"; and each R" is independently selected from H or alkyl;

with the proviso that when X is NH and $R_1$ is an unsubstituted phenyl, then $R_2$ is not

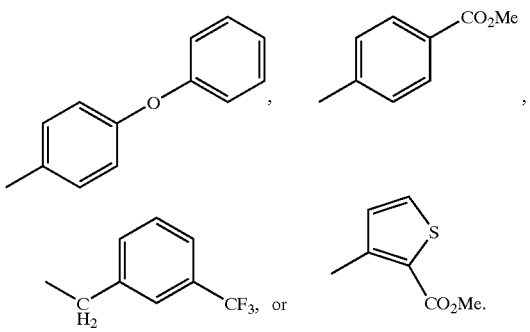

In a preferred embodiment, X is —NH or O and all other variables are as defined immediately above.

Other preferred compounds of the instant invention are those having the formula I:

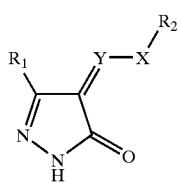

wherein:

R₁ is selected from carbocyclyl; heterocyclyl; aryl; heteroaryl; or —CN; wherein said carbocyclyl or heterocyclyl is optionally substituted with one to four substituents independently selected from halo, —R, —OR, —SR, —NO₂, —CN, —N(R)₂, —NRC(O)R, —NRC(O)N(R)₂, —NRCO₂R, —CO₂R, —C(O)R, —C(O)N(R)₂, —S(O)₂R, —S(O)₂N(R)₂, —S(O)R, —NRS(O)₂R, =O, =S, =NN(R)₂, =N—OR, =NN(R)COR, =NNRCO₂R, =NNRSO₂R, =N—CN, or =NR; and wherein said aryl or heteroaryl is optionally substituted with one to four substituents independently selected from halo, —R, —OR, —SR, —NO₂, —CN, —N(R)₂, —NRC(O)R, —NRC(O)N(R)₂, —NRCO₂R, —CO₂R, —C(O)R, —C(O)N(R)₂, —S(O)₂R, —S(O)₂N(R)₂, —S(O)R, or —NRS(O)₂R;

R₂ is selected from aryl; heteroaryl; carbocyclyl; or heterocyclyl; wherein said carbocyclyl or heterocyclyl is optionally substituted with one to four substituents independently selected from halo, —R, —OR, —SR, —NO₂, —CN, —N(R)₂, —NRC(O)R, —NRC(O)N(R)₂, —NRCO₂R, —CO₂R, —C(O)R, —C(O)N(R)₂, —S(O)₂R, —S(O)₂N(R)₂, —S(O)R, —NRS(O)₂R, =O, =S, =NN(R)₂, =N—OR, =NN(R)COR, =NNRCO₂R, =NNRSO₂R, =N—CN, or =NR; and wherein said aryl or heteroaryl is optionally substituted with one to four substituents independently selected from halo, —R, —OR, —SR, —NO₂, —CN, —N(R)₂, —NRC(O)R, —NRC(O)N(R)₂, —NRCO₂R, —CO₂R, —C(O)R, —C(O)N(R)₂, —S(O)₂R, —S(O)₂N(R)₂, —S(O)R, or —NRS(O)₂R;

X is O, S or —NH;

Y is N;

each R is independently selected from H; alkyl; carbocyclyl; heterocyclyl; aryl; heteroaryl; or any two R groups taken together form a carbocyclyl, heterocyclyl, aryl or heteroaryl group; wherein said alkyl, carbocyclyl, or heterocyclyl is optionally substituted with one to four substituents independently selected from halo, —R', —OR', —SR', —NO₂, —CN, —N(R')₂, —NR'C(O)R', —NR'C(O)N(R')₂, —N(R')CO₂R', —CO₂R', —C(O)R', —C(O)N(R')₂, —S(O)₂R', —S(O)₂N(R')₂, —S(O)R', —N(R')S(O)₂R', =O, =S, =NN(R')₂, =N—OR', =NN(R')COR', =NN(R')CO₂R', =NN(R')SO₂R', =N—CN, or =NR'; and wherein said aryl or heteroaryl is optionally substituted with one to four substituents independently selected from halo, —R', —OR', —SR', —NO₂, —CN, —N(R')₂, —NR'C(O)R', —NR'C(O)N(R')₂, —N(R') CO₂R', —CO₂R', —C(O)R', —C(O)N(R')₂, —S(O)₂R', —S(O)₂N(R')₂, —S(O)R', or —N(R')S(O)₂R';

each R' is independently selected from H; alkyl; carbocyclyl; heterocyclyl; aryl; heteroaryl; or any two R' groups taken together form a carbocyclyl, heterocyclyl, aryl or heteroaryl group; wherein said alkyl, carbocyclyl, or heterocyclyl is optionally substituted with one to four substituents independently selected from halo, CF₃, —R", —OR", —SR", —NO₂, —CN, —N(R")₂, —NR"C(O)R", —NR"C(O)N(R")₂, —N(R")CO₂R", —CO₂R", —C(O)R", —C(O)N(R")₂, —S(O)₂R", —S(O)₂N(R")₂, —S(O)R", —N(R")S(O)₂R", =O, =S, =NN(R")₂, =N—OR", =NN(R")COR", =NN(R")CO₂R", =NN(R")SO₂R", =N—CN, or =NR"; and wherein said aryl or heteroaryl is optionally substituted with one to four substituents independently selected from halo, CF₃, —R", —OR", —SR", —NO₂, —CN, —N(R")₂, —NR"C(O)R", —NR"C(O)N(R")₂, —N(R")CO₂R", —CO₂R", —C(O)R", —C(O)N(R")₂, —S(O)₂R", —S(O)₂N(R")₂, —S(O)R", or —N(R")S(O)₂R"; and each R" is independently selected from H or alkyl; with the proviso that:

i) when X is —NH and R₂ is an unsubstituted phenyl, then R₁ is not an unsubstituted phenyl;

ii) when X is O and R₁ is heterocyclyl, aryl or heteroaryl, then R₂ is not heteroaryl or heterocyclyl; and iii) R₁ excludes the following groups: unsubstituted 3-pyridyl, unsubstituted naphthyl,

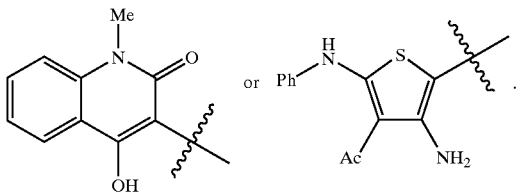

In a preferred embodiment, X is —NH or O and all other variables are as defined immediately above.

In another preferred embodiment, R₂ is an optionally substituted phenyl. In certain embodiments, R₁ is substituted aryl or substituted heteroaryl and R₂ is an optionally substituted phenyl. In other embodiments, R₁ is an unsubstituted phenyl or an substituted pyridyl and R₂ is an optionally substituted phenyl. In further preferred embodiments, R₁ is phenyl or pyridyl wherein said phenyl or pyridyl is substituted with —R₈, —O-(alkyl optionally substituted with —CO₂R₃, —OR₃ or —N(R₃)₂), —O-aralkyl, —O-carbocyclyl, —CO₂R₃, —SO₂R₃, —SO₂N (R₃)₂, —CF₃, halo, —CN, or heterocyclyl optionally substituted with =O or alkyl; R₂ is phenyl optionally substituted with —NO₂, —N(R₃)₂, —OR₃, —O-aryl, —O-aralkyl, —O-heterocyclylalkyl, —O-(alkyl optionally substituted with R⁺ or R₁₀), —O—CF₃, —CF₃, halo, —CN, —C(O)NH₂, —C(O)N(R₁₀)₂, —CO₂R₃, —S(O)₂NH₂, —S(O)₂N (R₁₀)₂, —S(O)₂N(R₄)₂, —S(O)₂R₁₀, R₃, R₄, —NR₃C(O) R₁₀, R₁₀, R⁺, —C(O)-aryl, or aryl optionally substituted with —NR"C(O)R", —N(R")₂, —CF₃, halo, —CN, —C(O) R", —OR", —O-aryl, or R₁₀; each R₃ is independently selected from H or alkyl; each R₄ is independently heteroaryl or heterocyclyl, wherein heterocyclyl is optionally substituted with =O, —CO₂R" or alkyl; each R₁₀ is independently alkyl optionally subsutituted with one or four substituents independently selected from the group consisting of —OR", —CO₂R", SO₂N(R")₂, —N(R")₂, NR"C(O) R" and CN; and R⁺ is —N(R')₂ wherein R' is alkyl optionally substituted with —OR'.

In another preferred embodiment, R₁ is selected from H, alkyl, heterocyclyl, aryl, or heteroaryl, wherein said alkyl or heterocyclyl is optionally substituted with one to four substituents independently selected from halo, —R, —OR, —SR, —NO₂, —CN, —N(R)₂, —NRC(O)R, —NRC(O)N (R)₂, —NRCO₂R, —CO₂R, —C(O)R, —C(O)N(R)₂, —S(O)₂R, —S(O)₂N(R)₂, —S(O)R, —NRS(O)₂R, =O, =S, =NN(R)$_2$, =N—OR, =NN(R)COR, =NNRCO$_2$R, =NNRSO$_2$R, =N—CN, or =NR, and wherein said aryl or heteroaryl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, or —NRS(O)$_2$R; R$_2$ is alkyl, carbocyclyl, heterocyclyl, aryl or heteroaryl, wherein said alkyl, carbocyclyl, or heterocyclyl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, —NRS(O)$_2$R, =O, =S, =NN(R)$_2$, =N—OR, =NN(R)COR, =NNRCO$_2$R, =NNRSO$_2$R, =N—CN, or =NR, and wherein said aryl or heteroaryl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, or —NRS(O)$_2$R; X is —NH or O and Y is N or CH.

In another preferred embodiment, R$_1$ is H, alkyl, heterocyclyl, aryl, or heteroaryl, wherein said alkyl, heterocyclyl, aryl, or heteroaryl is optionally substituted with one to four substituents independently selected from —OR, —CO$_2$R, —SO$_2$N(R)$_2$, —SO$_2$R, R$_8$, —CF$_3$, halo, —CN, or heterocyclyl optionally substituted with =O or alkyl; R$_2$ is alkyl, carbocyclyl, heterocyclyl, heterocyclyl substituted by =O, aryl or heteroaryl, wherein said alkyl, carbocyclyl, heterocyclyl, aryl or heteroaryl is optionally substituted with one to four substituents independently selected from —NO$_2$, —N(R)$_2$, —OR, —CF$_3$, halo, —CN, —CO$_2$R, —C(O)R, —C(O)N(R)$_2$, —N(R)C(O)R, —S(O)$_2$N(R)$_2$, —SO$_2$R, R$^+$, or R; R is H, CF$_3$, alkyl optionally substituted with R$_7$, aralkyl, heteroaryl optionally substituted with R$_9$, heterocyclyl optionally substituted with R$_7$, heterocyclylalkyl, carbocyclyl, or aryl optionally substituted with —NR"C(O)R", —N(R")$_2$, —NR"C(O)N(R")$_2$, —NR"S(O)$_2$R", —NO$_2$, —CF$_3$, halo, —CN, —CO$_2$R", —C(O)N(R")$_2$, —C(O)R", —SR", —S(O)R", —S(O)$_2$R", —S(O)$_2$N(R")$_2$, —OR", —O-aryl, or alkyl optionally substituted with —OR" or —CO$_2$R"; R$^+$ is —N(R')$_2$ wherein R' is alkyl optionally substituted with —OR"; R$_7$ is independently selected from the group consisting of =O, OR", R$^+$, —N(R")$_2$, R$_8$, —CO$_2$R", —SO$_2$N(R")$_2$, —NR"C(O)R", —CN and R"; R$_8$ is alkyl substituted with —OR"; R$_9$ is heterocyclyl or alkyl wherein alkyl is optionally substituted with one or more substituents independently selected from the group consisting of —OR" and —CO$_2$R"; X is —NH or O and Y is N or CH.

In yet another preferred embodiment, each R$_1$ and R$_2$ is independently heterocyclyl, aryl or heteroaryl, wherein said heterocyclyl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N (R)$_2$, —S(O)R, —NRS(O)$_2$R, =O, =S, =NN (R)$_2$, =N—OR, =NN (R)COR, =NNRCO$_2$R, =NNRSO$_2$R, =N—CN, or =NR, and wherein said aryl or heteroaryl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, or —NRS(O)$_2$R; X is —NH or O and Y is N or CH.

In another preferred embodiment, R$_1$ is H, alkyl, heterocyclyl, heteroaryl, or aryl, wherein each member of R$_1$ except H is optionally substituted with one to four substituents independently selected —OH, —R$_8$, —O-(alkyl optionally substituted with —CO$_2$R$_3$, —OR$_3$ or —N(R$_3$)$_2$), —O-aralkyl, —O-carbocyclyl, —CO$_2$R$_3$, —SO$_2$R$_3$, —SO$_2$N(R$_3$)$_2$, —CF$_3$, halo, —CN, or heterocyclyl optionally substituted with =O or alkyl; R$_2$ is alkyl, carbocyclyl, heterocyclyl, heterocyclyl substituted with =O, aryl or heteroaryl, wherein each member of R$_2$ is optionally substituted with one to four substituents independently selected from —NO$_2$, —N(R$_3$)$_2$, —OR$_3$, —O-aryl, —O-aralkyl, —O-heterocyclylalkyl, —O-(alkyl optionally substituted with R$^+$ or R$_{10}$), —O—CF$_3$, —CF$_3$, halo, —CN, —C(O)NH$_2$, —C(O)N(R$_{10}$)$_2$, —CO$_2$R$_3$, —S(O)$_2$NH$_2$, —S(O)$_2$N(R$_{10}$)$_2$, —S(O)$_2$N(R$_4$)$_2$, —S(O)$_2$R$_{10}$, R$_3$, R$_4$, —NR$_3$C(O) R$_{10}$, R$_{10}$, R$^+$, —C(O)-aryl, or aryl optionally substituted with —NR"C(O)R", —N(R")$_2$, —NO$_2$, —CF$_3$, halo, —CN, —C(O)R", —OR", —O-aryl, or R$_{10}$; each R$_3$ is independently selected from H or alkyl; each R$_4$ is independently heteroaryl or heterocyclyl, wherein heterocyclyl is optionally substituted with =O, —CO$_2$R" or alkyl; each R$_{10}$ is independently alkyl optionally subsutituted with one or four substituents independently selected from the group consisting of —OR", —CO$_2$R", SO$_2$N(R")$_2$, —N(R")$_2$, NR"C(O) R" and CN; X is —NH or O and Y is N or CH.

In yet another preferred embodiment, R$_1$ is H, methyl, i-propyl, benzodioxolyl, dihydrobenzodioxinyl, thienyl, pyridyl, phenyl, dihydrobenzodioxepinyl, pyrrolyl, or benzofuranyl, wherein benzodioxolyl, dihydrobenzodioxinyl, thienyl, pyridyl, phenyl, dihydrobenzodioxepinyl, pyrrolyl, or benzofuranyl is optionally substituted with one to four substituents independently selected from —OH, morpholinyl, dimethylazetidinone, —O-cyclopropyl, —O-cyclopentyl, R$_8$, —O-(alkyl optionally substituted with —CO$_2$R$_3$, —OR$_3$ or —N(R$_3$)$_2$), —O-aralkyl, —CO$_2$R$_3$, —SO$_2$R$_3$, —SO$_2$N (R$_3$)$_2$, —F, —CF$_3$, or —CN; R$_2$ is phenyl, dihydrobenzodioxinyl, tetrahydropyrimidinone, triazolyl, thiazolyl, hexahydropyridopyrazinone, dihydrobenzothiophene dioxide, dihydrobenzodioxepinyl, tetrahydroquinolinyl, dihydroindolyl, thienyl, pyridyl, benzyl, benzodioxolyl, carbazolyl, fluorenonyl, pyrazolyl, or cyclohexyl, wherein said phenyl, dihydrobenzodioxinyl, tetrahydropyrimidinone, triazolyl, thiazolyl, hexahydropyridopyrazinone, dihydrobenzothiophene dioxide, dihydrobenzodioxepinyl, tetrahydroquinolinyl, dihydroindolyl, thienyl, pyridyl, benzyl, benzodioxolyl, carbazolyl, fluorenonyl, pyrazolyl, or cyclohexyl is optionally substituted with one to four substituents independently selected from —NO$_2$, pyrazolidinone, dioxolanyl, —N(R$_3$)$_2$, —O(R$_3$)$_2$, —O—CF$_3$, —CF$_3$, —F, —Cl, —Br, —CN, —C(O)N(R$_{10}$)$_2$, R$_{10}$, R$_8$, morpholinyl, —SO$_2$N(R$_3$)$_2$, —SO$_2$-morpholinyl, —SO$_2$-piperazinedione, —SO$_2$N(R$_3$)$_2$, —SO$_2$R$_8$, —CO$_2$R$_3$, —CO$_2$R$_8$, —NR$_3$C(O)R$_3$, —O-phenyl, —O-Bn, —O-pyridyl, —C(O)-phenyl, pyridyl, thienyl, benzodioxolyl, furanyl, tetrahydrofuranyl optionally substituted with R$_8$, pyrrolidinone optionally substituted with —CO$_2$R", imidazolyl, —N-methylpiperazinyl, R$^+$, —O-alkyl wherein alkyl is substituted with R$_{10}$ or morpholinyl, or phenyl optionally substituted with one to four substituents independently selected from —N(R")$_2$, —OR", alkyl optionally substituted with —OR" or —CO$_2$R", benzodioxolyl, pyrrolyl, piperazinedione, —C(O)R", —NR"CO(R"), or —OPh; X is —NH or O and Y is N or CH.

In another preferred embodiment of the invention, X is —NH.

Another preferred embodiment of the invention is shown in formula III:

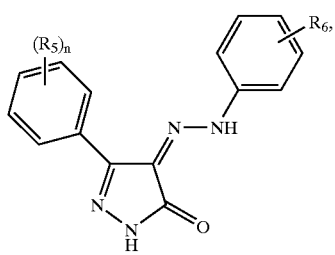

wherein R₅ is H, —R₈, —O-(alkyl optionally substituted with —CO₂R₃, —OR₃ or —N(R₃)₂), —O-aralkyl, —O-carbocyclyl, —CO₂R₃, —SO₂R₃, —SO₂N(R₃)₂, —CF₃, halo, —CN, or heterocyclyl optionally substituted with =O or alkyl; R₆ is —NO₂, —N(R₃)₂, —OR₃, —O-aryl, —O-aralkyl, —O-heterocyclylalkyl, —O-(alkyl optionally substituted with R⁺ or R₁₀), —O—CF₃, —CF₃, halo, —CN, —C(O)NH₂, —C(O)N(R₁₀)₂, —CO₂R₃, —S(O)₂NH₂, —S(O)₂N(R₁₀)₂, —S(O)₂N(R₄)₂, —S(O)₂R₁₀, R₃, R₄, —NR₃C(O)R₁₀, R₁₀, R⁺, —C(O)-aryl, or aryl optionally substituted with —NR"C(O)R", —N(R")₂, —CF₃, halo, —CN, —C(O)R", —OR", —O-aryl, or R₁₀; each R₃ is independently selected from H or alkyl; each R₄ is independently heteroaryl or heterocyclyl, wherein heterocyclyl is optionally substituted with =O, —CO₂R" or alkyl; each R₁₀ is independently alkyl optionally subsutituted with one or four substituents selected from the group consisting of —OR", —CO₂R", SO₂N(R")₂, —N(R")₂, NR"C(O)R" and CN; and and n is 1, 2, or 3. More preferably, R₅ is H, CF₃, F, morpholinyl, tetrahydropyrimidinone, —O—CH₂CH₂N(CH₃)₂, CN or —OCH₃ and R₆ is —NO₂, halo, —OCH₃, —O-cyclopropyl, —O-cyclopentyl, CH₃, —N(CH₃)₂, —N(CH₂CH₃)₂, pyridyl, pyrrolidinone, N-methylpiperazinyl, thienyl, benzodioxolyl, morpholinyl, furanyl, imidazolyl, tetrahydrofuranyl, dioxolanyl, —NHCOMe, —CF₃, —CONH₂, —CN, —OPh, —OBn, —COPh, —SO₂NH₂, —CO₂Me, —N(Et)(CH₂CH₂OH), —O—(CH₂)₃—NMe₂, —O—(CH₂)₃-morpholinyl, or phenyl optionally substituted by —O-phenyl, —C(O)Me, F, —NHCOMe, —NH₂, —NMe₂, —OMe, —OEt, benzodioxolyl, pyrrolyl, piperazinedione, —CH₂CH₂CO₂H, or —CH₂OH.

Representative examples of compounds of the present invention are shown below in Table 1 (the downward bond on the right side in the R₁ column and the downward bond on the left side in the R₂ column indicate the point of attachment to the remainder of the molecule).

TABLE 1

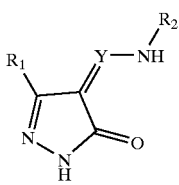

| Compound No. | Y | R₁ | R₂ |
| --- | --- | --- | --- |
| 1 | N | H | 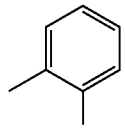 2-Cl-phenyl |
| 2 | N | H | 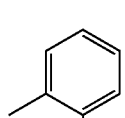 2-CF₃-phenyl |
| 3 | N | H₃C— |  3-CF₃-phenyl |
| 4 | N | H₃C— | 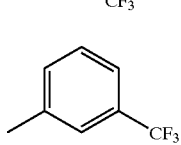 4-Br-phenyl |
| 5 | N | H |  3-Cl-phenyl |

TABLE 1-continued
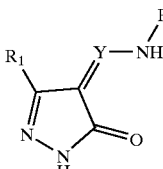
| Compound No. | Y | R₁ | R₂ |
|---|---|---|---|
| 6 | N |  | 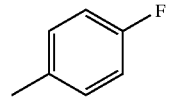 |
| 7 | N |  | 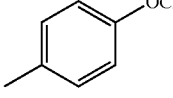 |
| 8 | N |  | 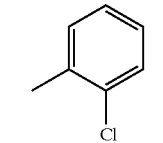 |
| 9 | N |  | 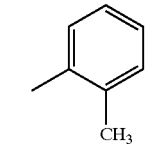 |
| 10 | N |  | 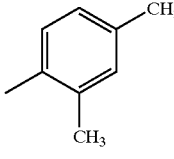 |
| 11 | N | H | 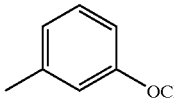 |
| 12 | N | 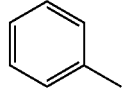 | 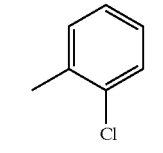 |
| 13 | N | 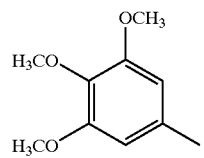 | 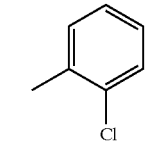 |
| 14 | N | 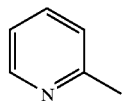 | 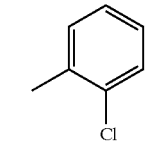 |

TABLE 1-continued

| Compound No. | Y | $R_1$ | $R_2$ |
|---|---|---|---|
| 15 | N | pyridin-3-yl | 2-chlorophenyl |
| 16 | N | pyridin-4-yl | 2-chlorophenyl |
| 17 | N | pyridin-2-yl | 4-chlorophenyl |
| 18 | N | pyridin-3-yl | 4-chlorophenyl |
| 19 | N | phenyl | 4-methoxyphenyl |
| 20 | N | pyridin-3-yl | 4-methoxyphenyl |
| 21 | N | pyridin-4-yl | 4-methoxyphenyl |
| 22 | N | 3,4,5-trimethoxyphenyl | 4-methoxyphenyl |
| 23 | N | 3,4,5-trimethoxyphenyl | 4-chlorophenyl |
| 24 | N | pyridin-4-yl | 4-chlorophenyl |

TABLE 1-continued
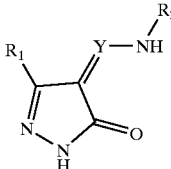
| Compound No. | Y | R₁ | R₂ |
| --- | --- | --- | --- |
| 25 | N | 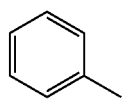 | 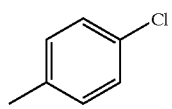 |
| 26 | N | 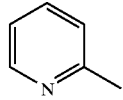 | 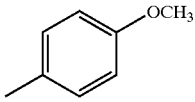 |
| 27 | N | 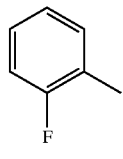 | 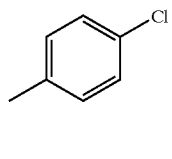 |
| 28 | N |  | 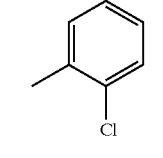 |
| 29 | N | 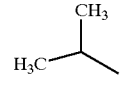 | 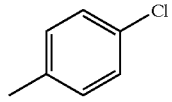 |
| 30 | N | 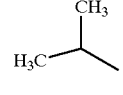 | 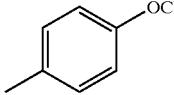 |
| 31 | N | 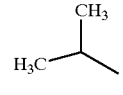 | 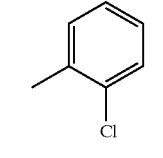 |
| 32 | N | 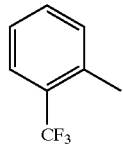 | 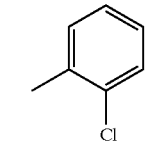 |
| 33 | N | 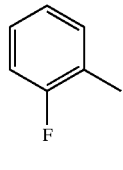 | 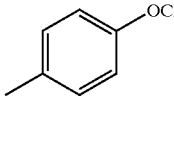 |

TABLE 1-continued
| Compound No. | Y | R₁ | R₂ |
|---|---|---|---|
| 34 | N | 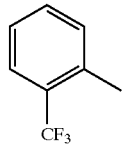 | 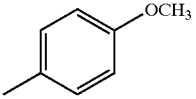 |
| 35 | N | 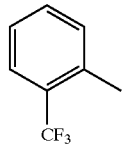 | 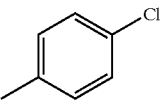 |
| 36 | N | 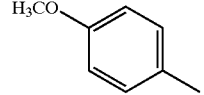 | 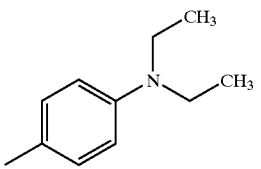 |
| 37 | N | 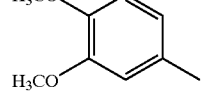 | 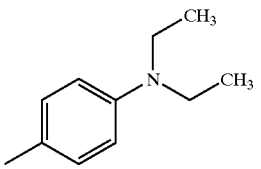 |
| 38 | N | 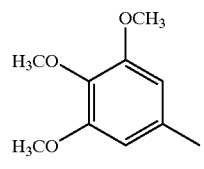 | 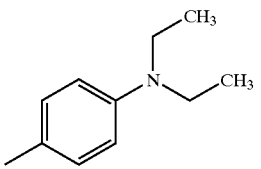 |
| 39 | N | 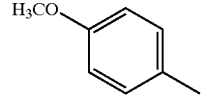 | 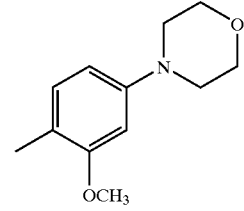 |
| 40 | N | 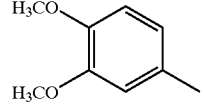 | 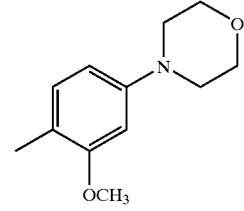 |

TABLE 1-continued
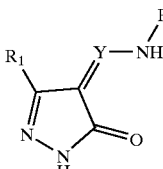
| Compound No. | Y | R₁ | R₂ |
| --- | --- | --- | --- |
| 41 | N | 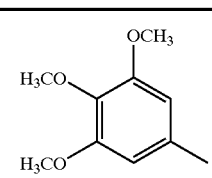 | 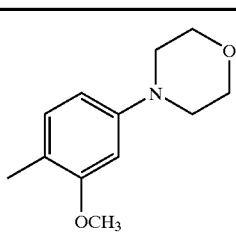 |
| 42 | N | 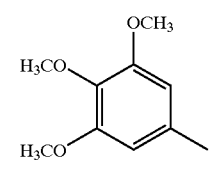 | 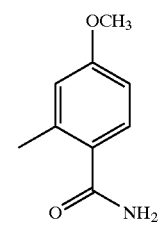 |
| 43 | N | 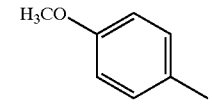 | 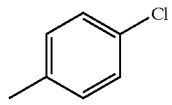 |
| 44 | N | 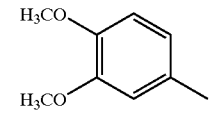 | 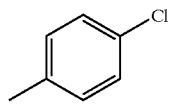 |
| 45 | N | 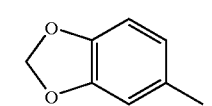 | 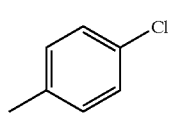 |
| 46 | N | 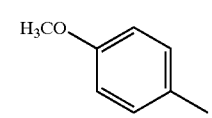 | 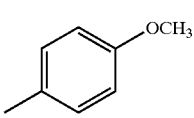 |
| 47 | N | 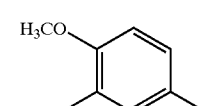 | 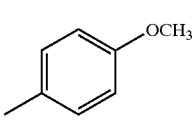 |
| 48 | N | 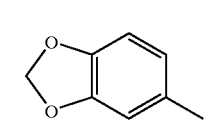 | 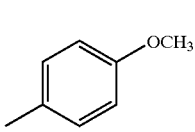 |
| 49 | N | 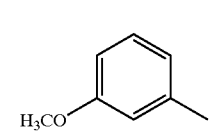 | 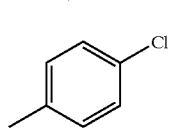 |

TABLE 1-continued
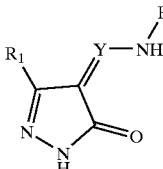
| Compound No. | Y | R₁ | R₂ |
|---|---|---|---|
| 50 | N | 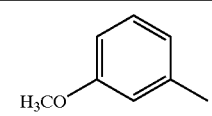 | 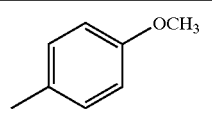 |
| 51 | N | 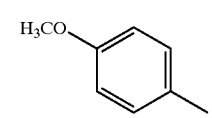 | 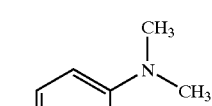 |
| 52 | N | 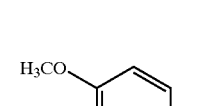 | 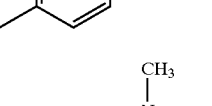 |
| 53 | N | 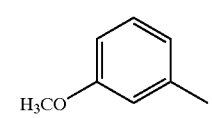 | 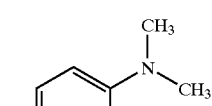 |
| 54 | N | 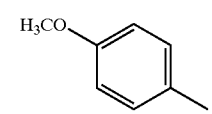 | 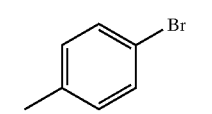 |
| 55 | N | 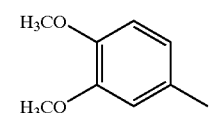 | 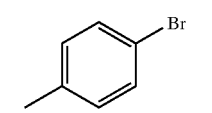 |
| 56 | N | 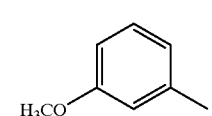 | 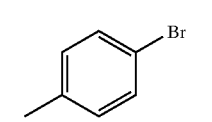 |
| 57 | N | 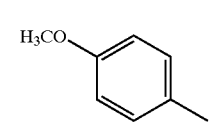 | 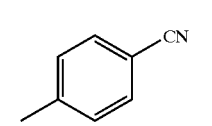 |
| 58 | N | 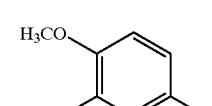 | 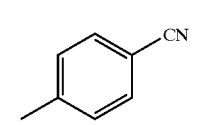 |
| 59 | N | 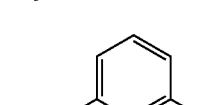 | 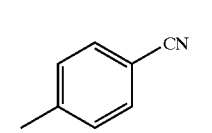 |

TABLE 1-continued

| Compound No. | Y | R₁ | R₂ |
|---|---|---|---|
| 60 | N | 4-H₃CO-C₆H₄- | 4-(morpholin-4-yl)-C₆H₄- |
| 61 | N | 3,4-(H₃CO)₂-C₆H₃- | 4-(morpholin-4-yl)-C₆H₄- |
| 62 | N | 3-H₃CO-C₆H₄- | 4-(morpholin-4-yl)-C₆H₄- |
| 63 | N | 4-H₃CO-C₆H₄- | 4-CF₃-C₆H₄- |
| 64 | N | 3,4-(H₃CO)₂-C₆H₃- | 4-CF₃-C₆H₄- |
| 65 | N | 3-H₃CO-C₆H₄- | 4-CF₃-C₆H₄- |
| 66 | N | 4-H₃CO-C₆H₄- | 3-CF₃-C₆H₄- |
| 67 | N | 3,4-(H₃CO)₂-C₆H₃- | 3-CF₃-C₆H₄- |
| 68 | N | 3-H₃CO-C₆H₄- | 3-CF₃-C₆H₄- |
| 69 | N | 4-H₃CO-C₆H₄- | 3-Cl-C₆H₄- |

TABLE 1-continued

| Compound No. | Y | R₁ | R₂ |
|---|---|---|---|
| 70 | N | 3,4-di(H₃CO)-phenyl | 3-Cl-phenyl |
| 71 | N | 3-H₃CO-phenyl | 3-Cl-phenyl |
| 72 | N | 4-H₃CO-phenyl | 3-OCH₃-phenyl |
| 73 | N | 3,4-di(H₃CO)-phenyl | 3-OCH₃-phenyl |
| 74 | N | 3-H₃CO-phenyl | 3-OCH₃-phenyl |
| 75 | N | 4-NC-phenyl | 4-Cl-phenyl |
| 76 | N | 4-NC-phenyl | 4-OCH₃-phenyl |
| 77 | N | 4-H₃CO-phenyl | 4-NO₂-phenyl |
| 78 | N | 3-H₃CO-phenyl | 4-NO₂-phenyl |
| 79 | N | 4-H₃CO-phenyl | 4-biphenyl |

US 6,916,798 B2
TABLE 1-continued
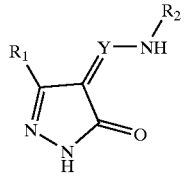
| Compound No. | Y | R₁ | R₂ |
|---|---|---|---|
| 80 | N | 3,4-dimethoxyphenyl | 4-biphenyl |
| 81 | N | 3-methoxyphenyl | 4-biphenyl |
| 82 | N | 4-methoxyphenyl | 4'-fluoro-4-biphenyl |
| 83 | N | 3,4-dimethoxyphenyl | 4'-fluoro-4-biphenyl |
| 84 | N | 3-methoxyphenyl | 4'-fluoro-4-biphenyl |
| 85 | N | 4-methoxyphenyl | 4-phenoxyphenyl |
| 86 | N | 3,4-dimethoxyphenyl | 4-phenoxyphenyl |
| 87 | N | 3-methoxyphenyl | 4-phenoxyphenyl |
| 88 | N | 4-methoxyphenyl | 3-phenoxyphenyl |

TABLE 1-continued
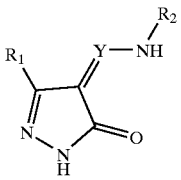
| Compound No. | Y | R₁ | R₂ |
| --- | --- | --- | --- |
| 89 | N | 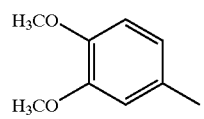 | 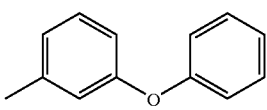 |
| 90 | N | 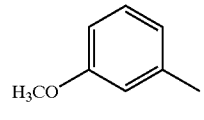 | 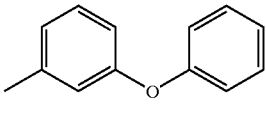 |
| 91 | CH | 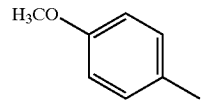 | 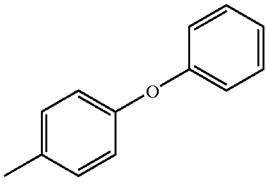 |
| 92 | CH | 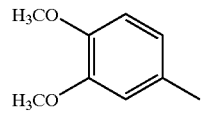 | 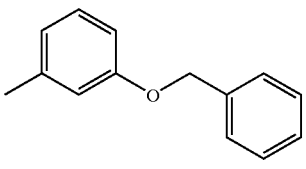 |
| 93 | CH | 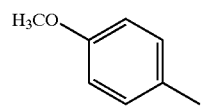 | 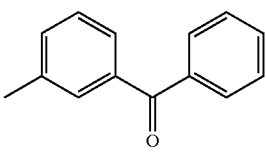 |
| 94 | CH | 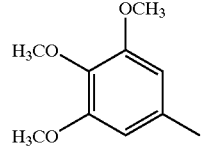 | 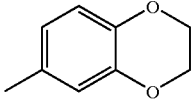 |
| 95 | CH | 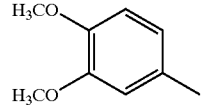 | 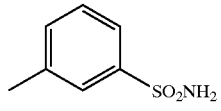 |
| 96 | CH | 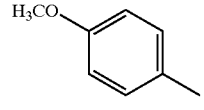 | 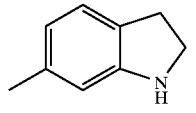 |

TABLE 1-continued
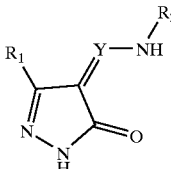
| Compound No. | Y | R₁ | R₂ |
|---|---|---|---|
| 97 | CH | 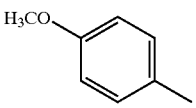 | 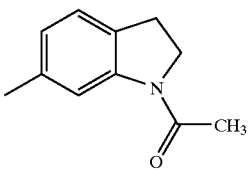 |
| 98 | CH | 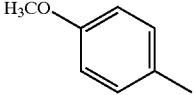 | 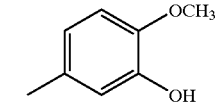 |
| 99 | CH | 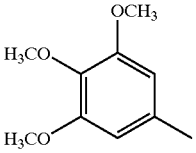 | 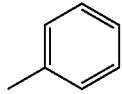 |
| 100 | CH | 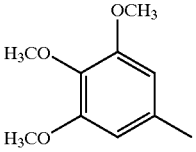 | 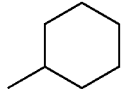 |
| 101 | CH | 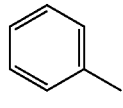 | 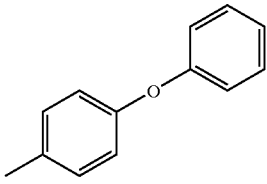 |
| 102 | CH | 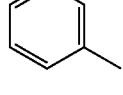 | 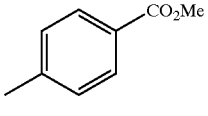 |
| 103 | CH | 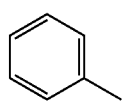 | 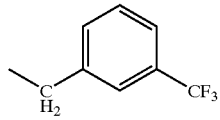 |
| 104 | CH | 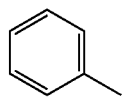 | 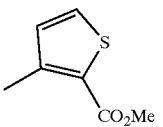 |

TABLE 1-continued
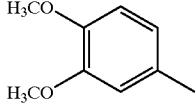
| Compound No. | Y | R₁ | R₂ |
|---|---|---|---|
| 105 | N | 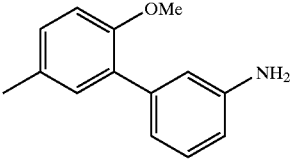 | 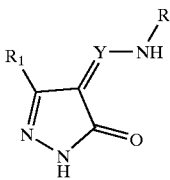 |
| 106 | N | 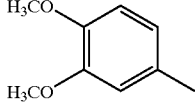 | 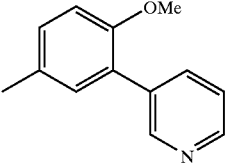 |
| 107 | N | 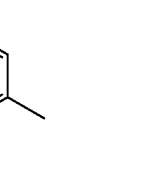 | 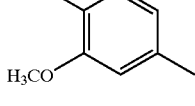 |
| 108 | N | 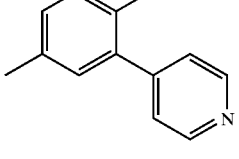 | 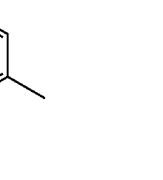 |
| 109 | N | 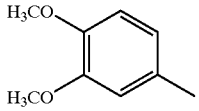 | 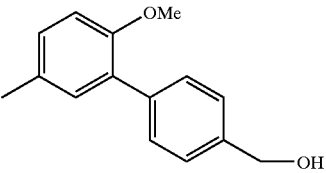 |
| 110 | N | 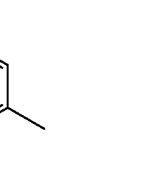 | 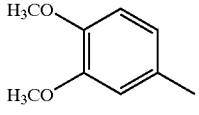 |
| 111 | N | 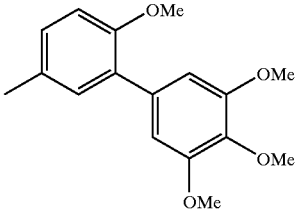 | 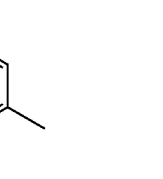 |

TABLE 1-continued
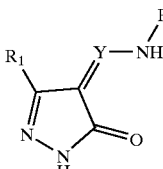
| Compound No. | Y | R₁ | R₂ |
|---|---|---|---|
| 112 | N | 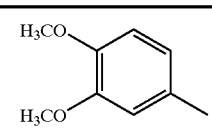 | 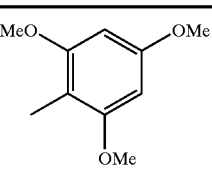 |
| 113 | N | 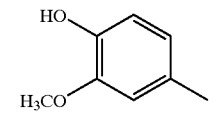 | 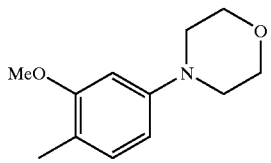 |
| 114 | N | 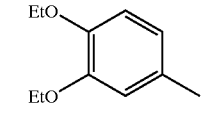 | 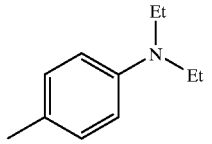 |
| 115 | N | 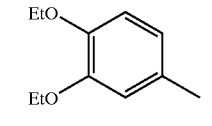 | 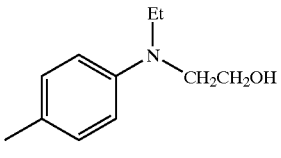 |
| 116 | N | 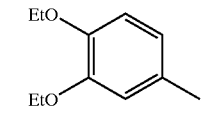 | 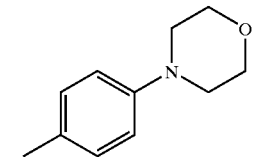 |
| 117 | N | 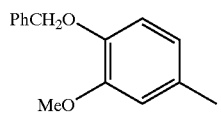 | 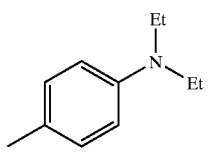 |
| 118 | N | 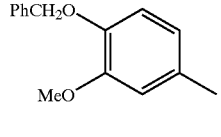 | 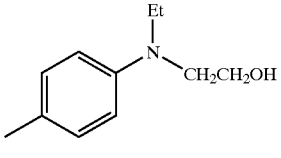 |
| 119 | N | 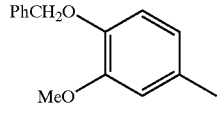 | 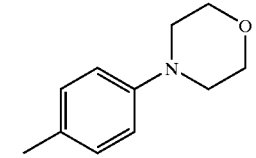 |

TABLE 1-continued

| Compound No. | Y | R₁ | R₂ |
|---|---|---|---|
| 120 | N | 3,4-dimethoxyphenyl | 2-(3-(N-methyl-N-(2-hydroxyethyl)amino)propoxy)-5-methyl-biphenyl |
| 121 | N | 3,4-dimethoxyphenyl | 2-(3-(dimethylamino)propoxy)-5-methyl-biphenyl |
| 122 | N | 3,4-dimethoxyphenyl | 2-(3-morpholinopropoxy)-5-methyl-biphenyl |
| 123 | N | 3,4-dimethoxyphenyl | 2-methoxy-5-methyl-3-morpholinophenyl |
| 124 | N | 3,4-dimethoxyphenyl | 2-methoxy-5-methyl-3-(4-methylpiperazin-1-yl)phenyl |
| 125 | N | 3,4,5-trimethoxyphenyl | 2-methoxy-5-methyl-3-morpholinophenyl |

TABLE 1-continued
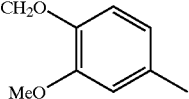
| Compound No. | Y | R₁ | R₂ |
|---|---|---|---|
| 126 | N | 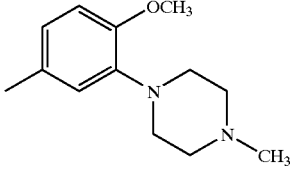 | 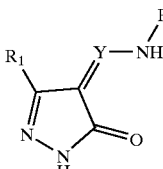 |
| 127 | N | 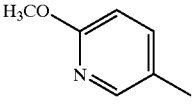 | 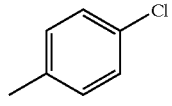 |
| 128 | N | 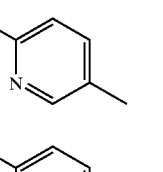 | 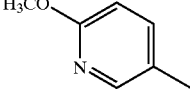 |
| 129 | N | 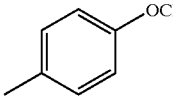 | 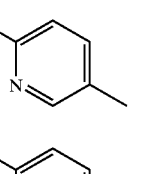 |
| 130 | N | 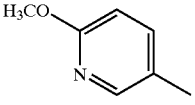 | 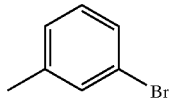 |
| 131 | N | 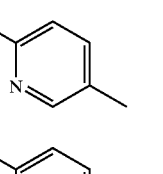 | 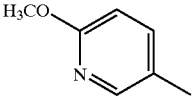 |
| 132 | N | 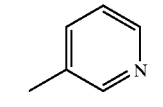 | 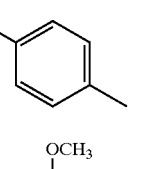 |
| 133 | N | 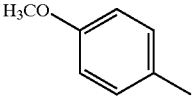 | 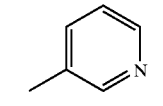 |
| 134 | N | 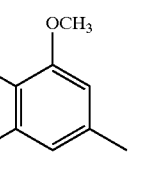 | 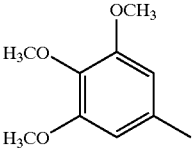 |

TABLE 1-continued
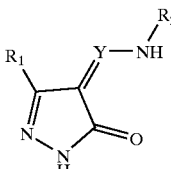
| Compound No. | Y | R₁ | R₂ |
| --- | --- | --- | --- |
| 135 | N | 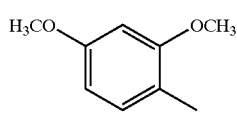 | 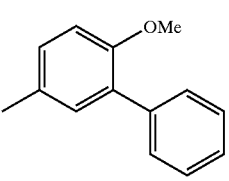 |
| 136 | N | 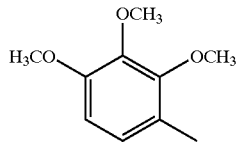 | 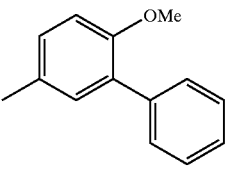 |
| 137 | N | 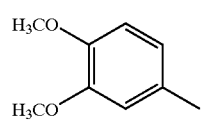 | 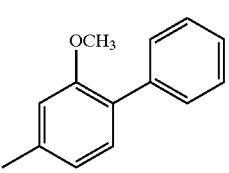 |
| 138 | N | 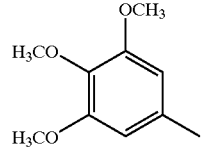 | 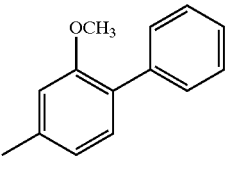 |
| 139 | N | 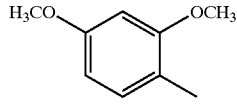 | 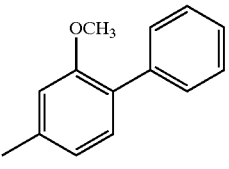 |
| 140 | N | 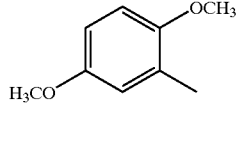 | 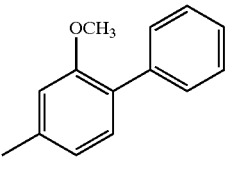 |
| 141 | N | 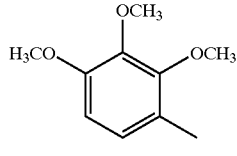 | 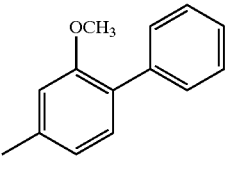 |

TABLE 1-continued
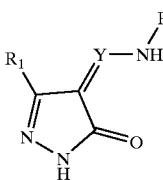
| Compound No. | Y | R₁ | R₂ |
|---|---|---|---|
| 142 | N | 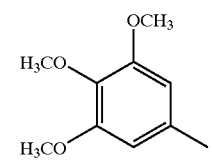 | 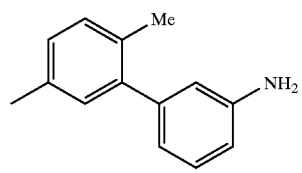 |
| 143 | N | 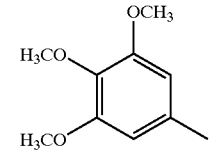 | 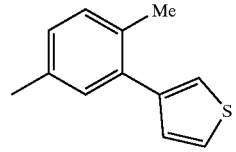 |
| 144 | N | 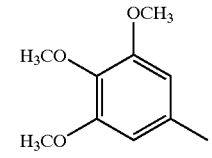 | 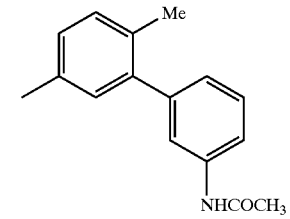 |
| 145 | N | 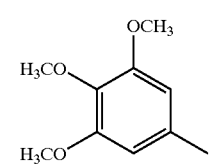 | 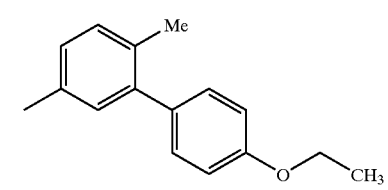 |
| 146 | N | 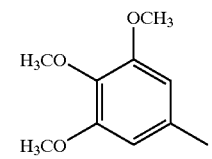 | 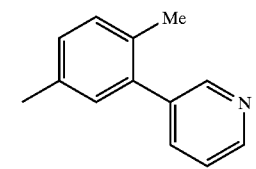 |
| 147 | N | 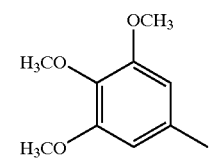 | 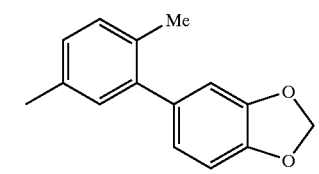 |
| 148 | N | 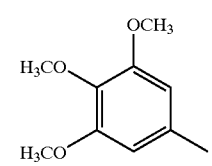 | 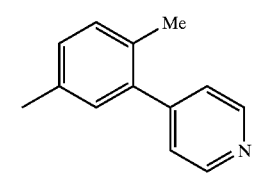 |

TABLE 1-continued
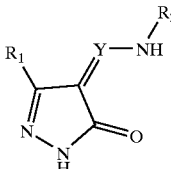
| Compound No. | Y | R₁ | R₂ |
|---|---|---|---|
| 149 | N | 3,4,5-trimethoxyphenyl | 4-acetyl-2',5'-dimethylbiphenyl |
| 150 | N | 3,4,5-trimethoxyphenyl | 2',5'-dimethyl-3,4,5-trimethoxybiphenyl |
| 151 | N | 2,4-dimethoxy-phenyl | 3-amino-2',5'-dimethylbiphenyl |
| 152 | N | 2,4-dimethoxy-phenyl | 4-(hydroxymethyl)-2',5'-dimethylbiphenyl |
| 153 | N | 2,4-dimethoxy-phenyl | 2',5'-dimethyl-3,4-methylenedioxybiphenyl |
| 154 | N | 2,4-dimethoxy-phenyl | 2',5'-dimethyl-3,4,5-trimethoxybiphenyl |

TABLE 1-continued

| Compound No. | Y | R₁ | R₂ |
|---|---|---|---|
| 155 | N | 2,4-dimethoxy-3-methylphenyl | 2',5'-dimethyl-4-phenoxy-biphenyl-3-yl |
| 156 | N | 2,4-dimethoxy-3-methylphenyl | 3'-(acetylamino)-2,5-dimethyl-biphenyl-3-yl |
| 157 | N | 2,4-dimethoxy-3-methylphenyl | 4'-ethoxy-2,5-dimethyl-biphenyl-3-yl |
| 158 | N | 2,4-dimethoxy-3-methylphenyl | 2-methyl-5-(pyridin-3-yl)phenyl |
| 159 | N | 2,4-dimethoxy-3-methylphenyl | 4'-(hydroxymethyl)-2,5-dimethyl-biphenyl-3-yl |
| 160 | N | 2,4-dimethoxy-3-methylphenyl | 2,5-dimethyl-3',4',5'-trimethoxy-biphenyl-3-yl |

TABLE 1-continued

| Compound No. | Y | R₁ | R₂ |
|---|---|---|---|
| 161 | N | 3,4,5-trimethoxyphenyl (OCH₃ at 2, H₃CO at 3, H₃CO at 5) | 2-methyl-5-methyl-4'-phenoxybiphenyl |
| 162 | N | 3,4,5-trimethoxyphenyl | 2-methyl-5-methyl-3'-ethoxybiphenyl |
| 163 | N | 3,4-dimethoxyphenyl | 2-Me-5-methyl-4'-(hydroxymethyl)biphenyl |
| 164 | N | 3,4-dimethoxyphenyl | 2-methyl-5-methyl-phenyl-4-pyridyl |
| 165 | N | 3,4-dimethoxyphenyl | 2-methyl-5-methyl-3',4',5'-trimethoxybiphenyl |
| 166 | N | 2,4-dimethoxyphenyl | 2-methyl-5-methyl-4'-phenoxybiphenyl |

TABLE 1-continued

| Compound No. | Y | R₁ | R₂ |
|---|---|---|---|
| 167 | N | 2,5-dimethoxy-4-methylphenyl | 2-methyl-5-methyl-phenyl with 3-thienyl substituent |
| 168 | N | 2,5-dimethoxy-4-methylphenyl | 2-methyl-5-methyl-biphenyl with 3-NHCOCH₃ |
| 169 | N | 2,5-dimethoxy-4-methylphenyl | 2-methyl-5-methyl-biphenyl with 4-OEt |
| 170 | N | 2,5-dimethoxy-4-methylphenyl | 2-methyl-5-methyl-phenyl with 3-pyridyl |
| 171 | N | 2,5-dimethoxy-4-methylphenyl | 2-methyl-5-methyl-phenyl with 3-furyl |
| 172 | N | 2,4-dimethoxy-3-methylphenyl | 2-methyl-5-methyl-phenyl with 3-thienyl |
| 173 | N | 2,4-dimethoxy-3-methylphenyl | 2-methyl-5-methyl-biphenyl with 3-OEt |

TABLE 1-continued

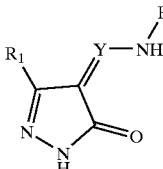

| Compound No. | Y | R₁ | R₂ |
|---|---|---|---|
| 174 | N | 2,4-dimethoxy-methylphenyl | 2-methyl-5-(pyridin-4-yl)phenyl |
| 175 | N | 2,4-dimethoxy-methylphenyl | 4'-acetyl-2,5-dimethylbiphenyl |
| 176 | N | 2,3-dimethoxy-6-methoxy-methylphenyl | 2-methyl-5-(thiophen-3-yl)phenyl |
| 177 | N | 2,3-dimethoxy-6-methoxy-methylphenyl | 4'-ethoxy-2,5-dimethylbiphenyl |
| 178 | N | 2,3-dimethoxy-6-methoxy-methylphenyl | 2-methyl-5-(pyridin-3-yl)phenyl |
| 179 | N | 2,3-dimethoxy-6-methoxy-methylphenyl | 3',4',5'-trimethoxy-2,5-dimethylbiphenyl |
| 180 | N | 2,3-dimethoxy-6-methoxy-methylphenyl | 2-methyl-5-(furan-3-yl)phenyl |

TABLE 1-continued
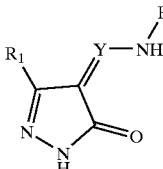
| Compound No. | Y | R₁ | R₂ |
|---|---|---|---|
| 181 | N | 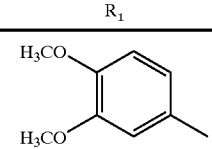 | 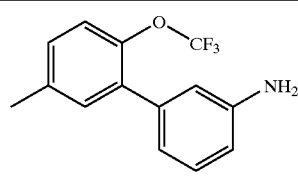 |
| 182 | N | 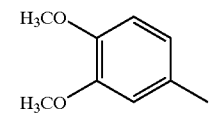 | 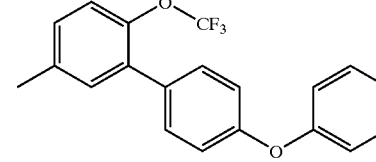 |
| 183 | N | 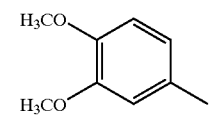 | 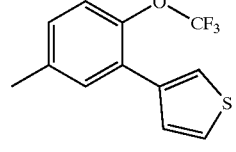 |
| 184 | N | 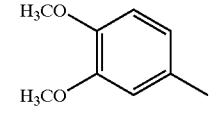 | 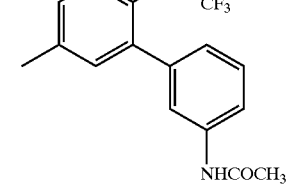 |
| 185 | N | 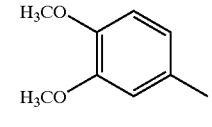 | 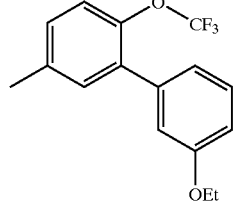 |
| 186 | N | 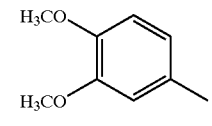 | 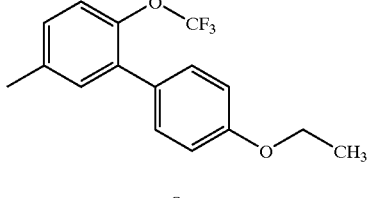 |
| 187 | N | 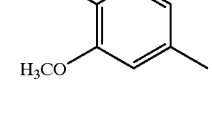 | 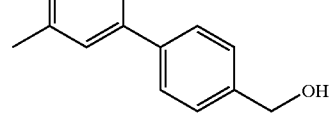 |

TABLE 1-continued
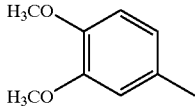
| Compound No. | Y | R₁ | R₂ |
|---|---|---|---|
| 188 | N | 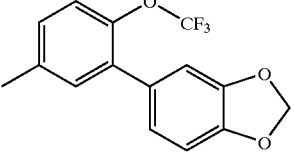 | 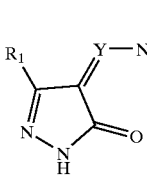 |
| 189 | N | 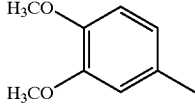 | 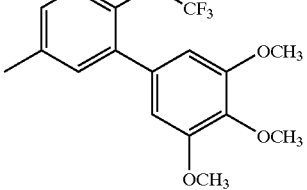 |
| 190 | N |  | 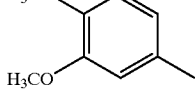 |
| 191 | N | 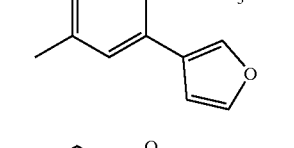 | 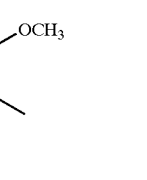 |
| 192 | N | 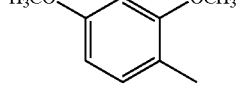 | 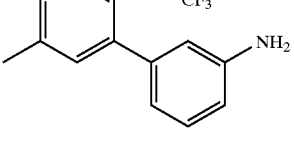 |
| 193 | N | 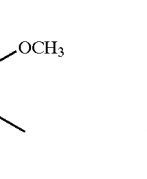 | 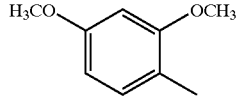 |
| 194 | N | 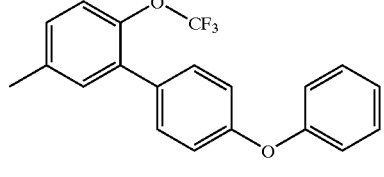 | 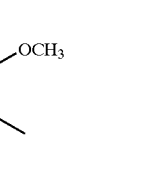 |

TABLE 1-continued
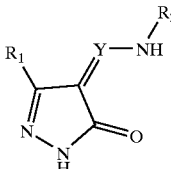
| Compound No. | Y | R$_1$ | R$_2$ |
|---|---|---|---|
| 195 | N | 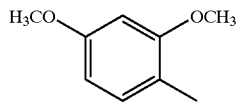 | 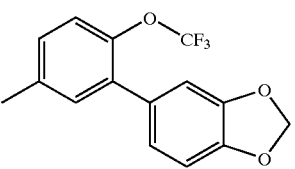 |
| 196 | N | 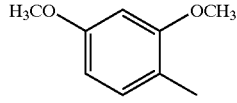 | 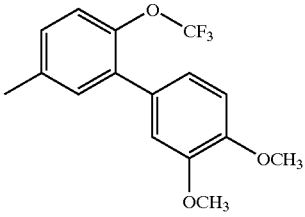 |
| 197 | N | 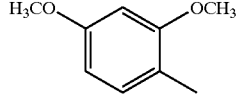 | 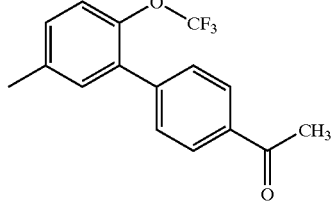 |
| 198 | N | 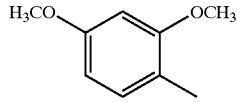 | 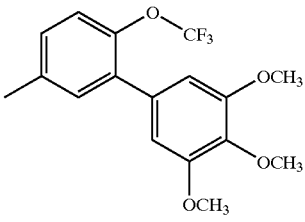 |
| 199 | N | 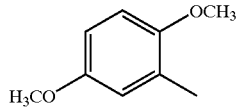 | 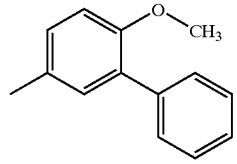 |
| 200 | N | 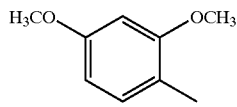 | 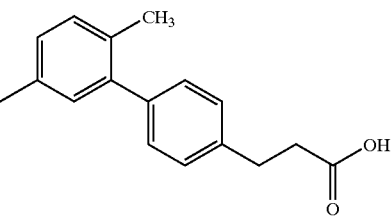 |

TABLE 1-continued
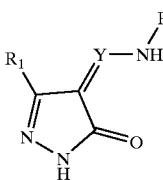
| Compound No. | Y | R₁ | R₂ |
|---|---|---|---|
| 201 | N | 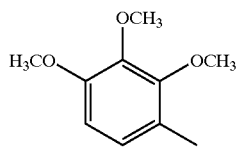 | 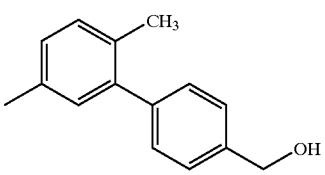 |
| 202 | N | 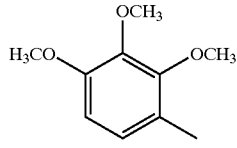 | 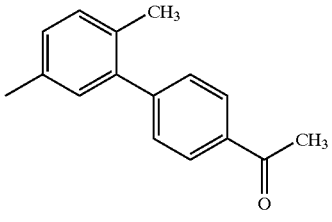 |
| 203 | N | 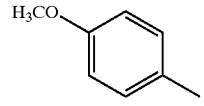 | 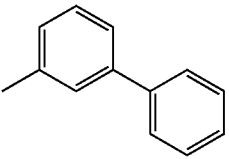 |
| 204 | N | 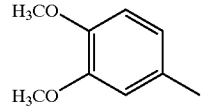 | 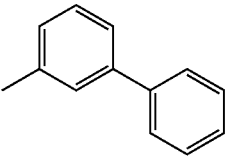 |
| 205 | N | 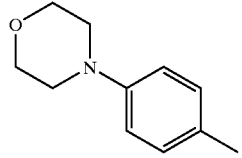 | 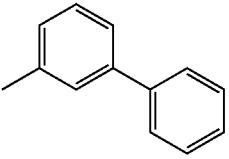 |
| 206 | N | 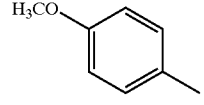 | 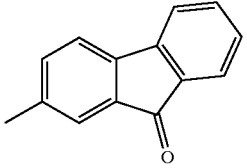 |
| 207 | N | 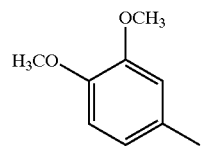 | 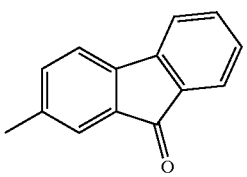 |

TABLE 1-continued
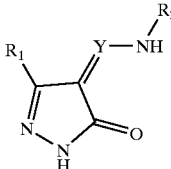
| Compound No. | Y | R₁ | R₂ |
|---|---|---|---|
| 208 | N | 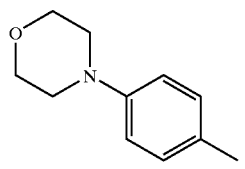 | 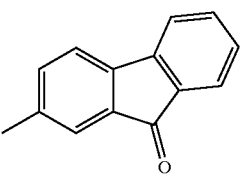 |
| 209 | N | 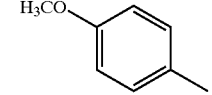 | 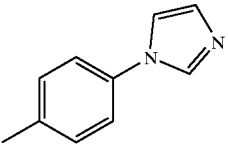 |
| 210 | N | 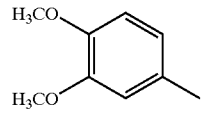 | 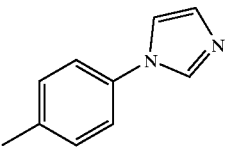 |
| 211 | N | 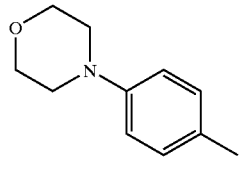 | 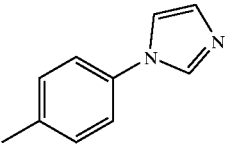 |
| 212 | N | 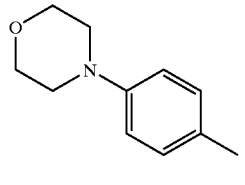 | 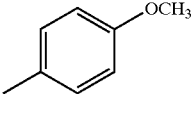 |
| 213 | N | 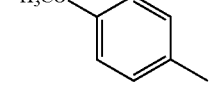 | 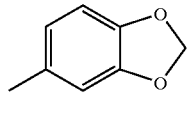 |
| 214 | N | 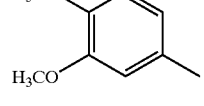 | 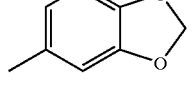 |
| 215 | N | 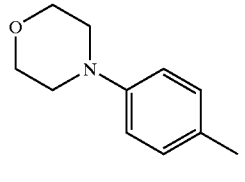 | 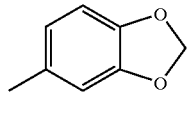 |

TABLE 1-continued
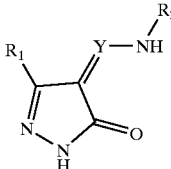
| Compound No. | Y | R₁ | R₂ |
|---|---|---|---|
| 216 | N | 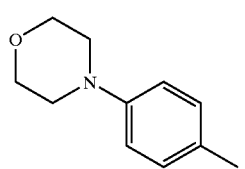 | 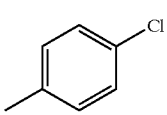 |
| 217 | N | 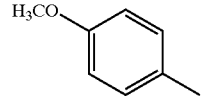 | 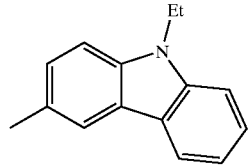 |
| 218 | N | 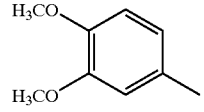 | 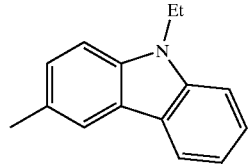 |
| 219 | N | 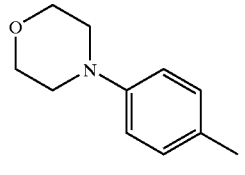 | 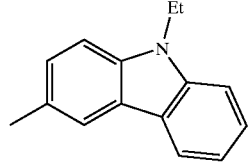 |
| 220 | N | 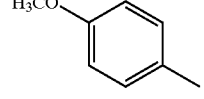 | 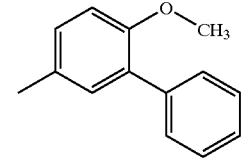 |
| 221 | N | 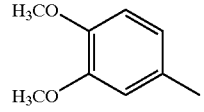 | 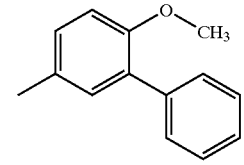 |
| 222 | N | 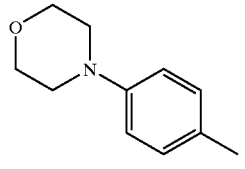 | 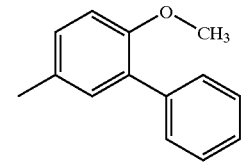 |

TABLE 1-continued
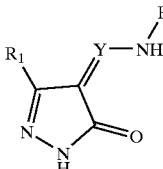
| Compound No. | Y | R₁ | R₂ |
|---|---|---|---|
| 223 | N | 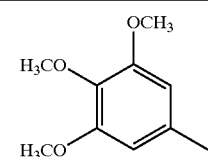 | 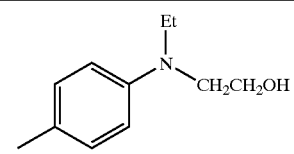 |
| 224 | CH | 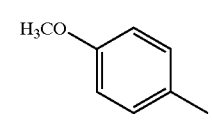 | 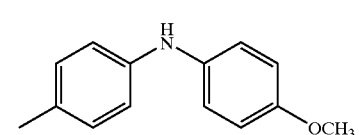 |
| 225 | N | 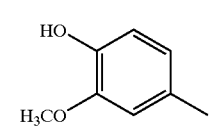 | 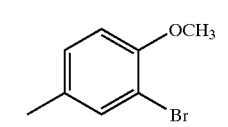 |
| 226 | N | 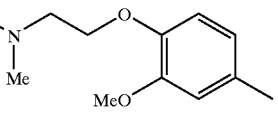 | 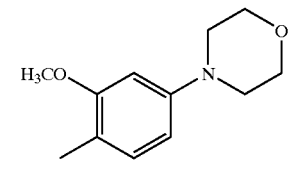 |
| 227 | CH | 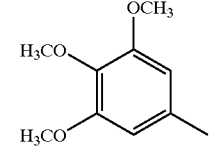 | 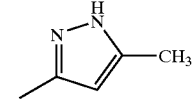 |
| 228 | N | 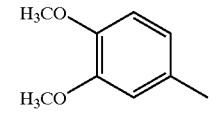 | 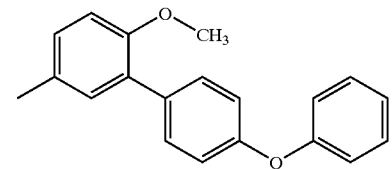 |
| 229 | N | 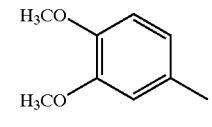 | 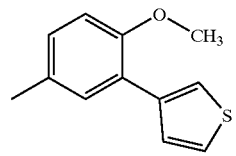 |
| 230 | N | 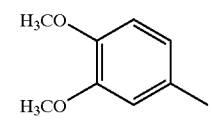 | 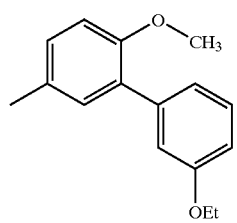 |

TABLE 1-continued

| Compound No. | Y | R₁ | R₂ |
|---|---|---|---|
| 231 | N | 3,4-dimethoxyphenyl | 2-methoxy-5-(4-ethoxyphenyl)phenyl |
| 232 | N | 3,4-dimethoxyphenyl | 2-methoxy-5-(furan-2-yl)phenyl |
| 233 | N | 3,4-dimethoxyphenyl | 2-methoxy-5-(3,4-dimethoxyphenyl)phenyl |
| 234 | N | 3,4-dimethoxyphenyl | 2-methoxy-5-(2-hydroxyphenyl)phenyl |
| 235 | N | 3,4-dimethoxyphenyl | 2-methoxy-5-(furan-3-yl)phenyl |
| 236 | N | 3,4-dimethoxyphenyl | 2-methoxy-5-(2-acetylphenyl)phenyl |
| 237 | N | 3,4,5-trimethoxyphenyl | 2-methoxy-5-(3-aminophenyl)phenyl |

TABLE 1-continued
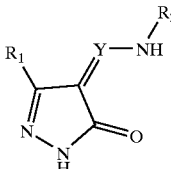
| Compound No. | Y | R₁ | R₂ |
|---|---|---|---|
| 238 | N | 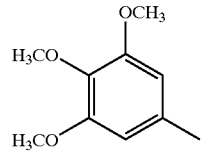 | 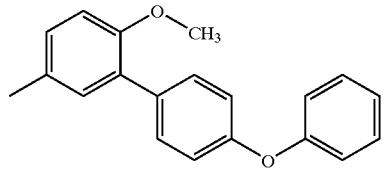 |
| 239 | N | 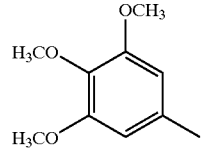 | 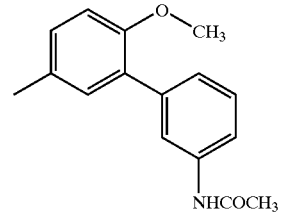 |
| 240 | N | 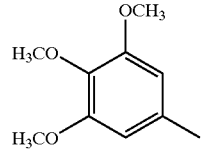 | 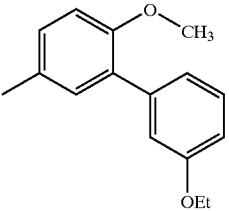 |
| 241 | N | 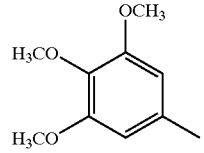 | 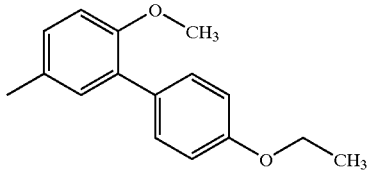 |
| 242 | N | 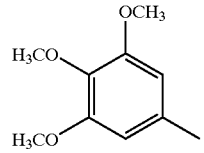 | 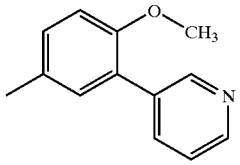 |
| 243 | N | 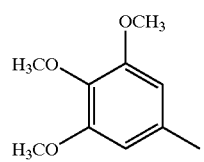 | 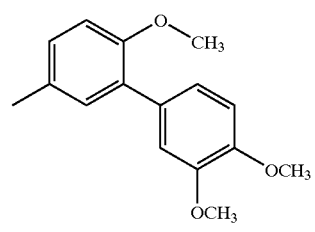 |

TABLE 1-continued
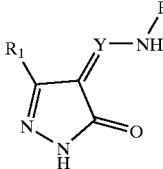
| Compound No. | Y | R₁ | R₂ |
|---|---|---|---|
| 244 | N | 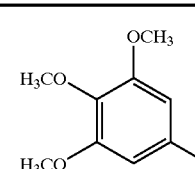 | 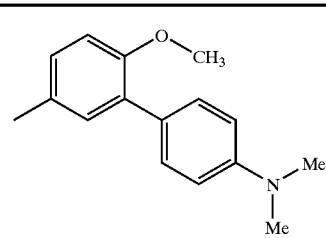 |
| 245 | N | 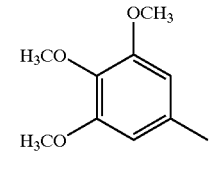 | 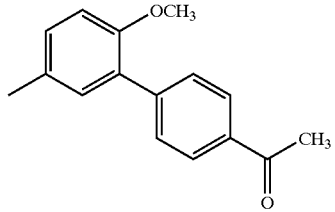 |
| 246 | N | 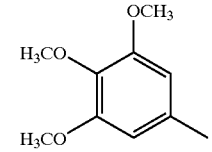 | 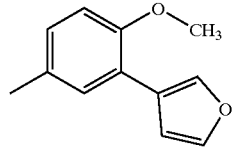 |
| 247 | N | 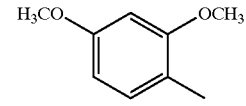 | 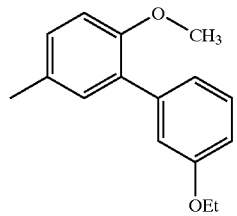 |
| 248 | N | 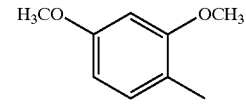 | 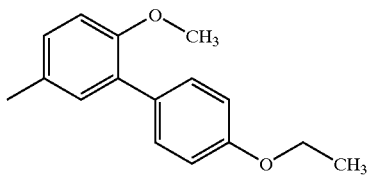 |
| 249 | N | 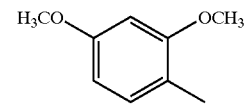 | 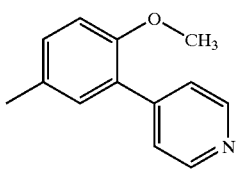 |

TABLE 1-continued
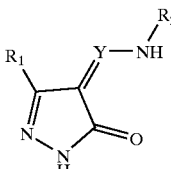
| Compound No. | Y | R₁ | R₂ |
|---|---|---|---|
| 250 | N | 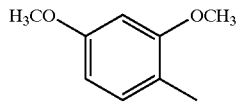 | 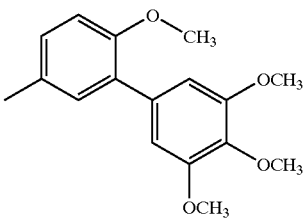 |
| 251 | N | 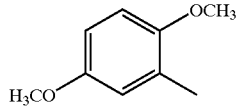 | 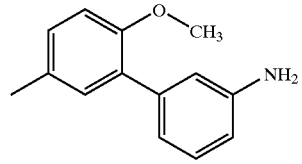 |
| 252 | N | 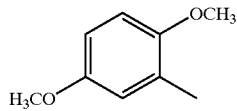 | 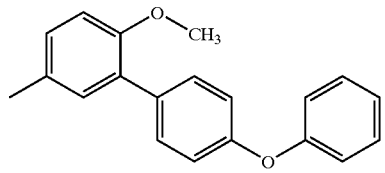 |
| 253 | N | 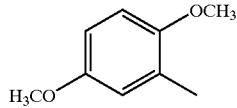 | 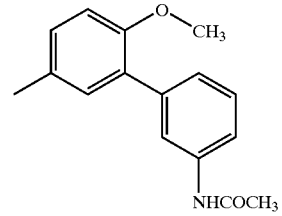 |
| 254 | N | 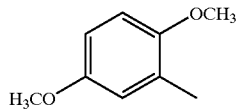 | 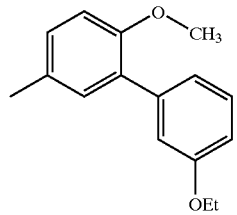 |
| 255 | N | 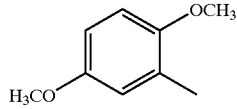 | 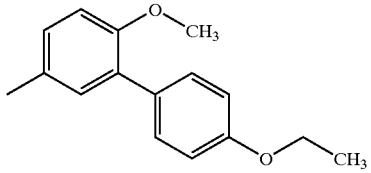 |

US 6,916,798 B2
TABLE 1-continued
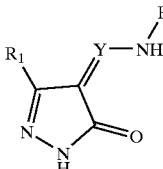
| Compound No. | Y | R₁ | R₂ |
|---|---|---|---|
| 256 | N | 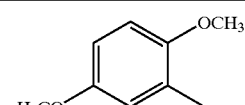 | 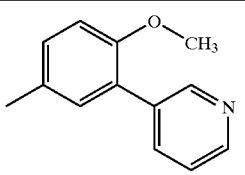 |
| 257 | N | 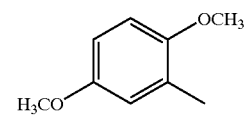 | 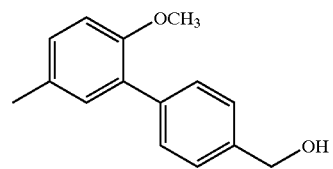 |
| 258 | N | 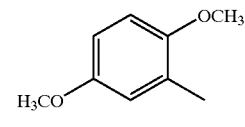 | 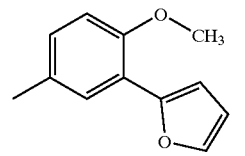 |
| 259 | N | 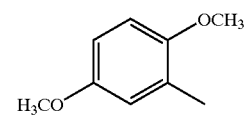 | 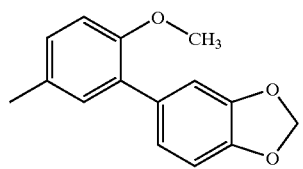 |
| 260 | N | 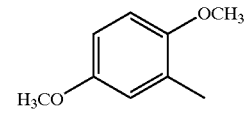 | 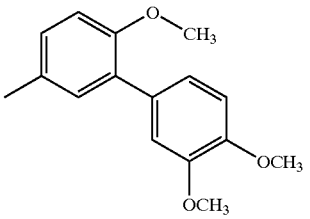 |
| 261 | N | 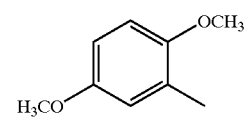 | 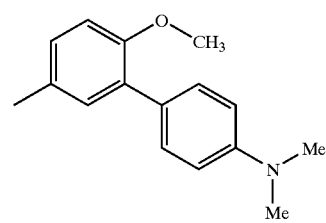 |
| 262 | N | 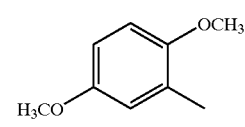 | 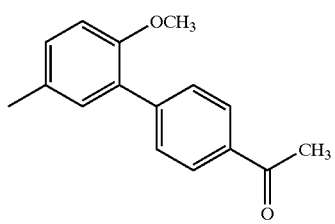 |

TABLE 1-continued

| Compound No. | Y | R₁ | R₂ |
|---|---|---|---|
| 263 | N | 2,5-dimethoxy-4-methylphenyl | 2-methoxy-5-methyl-3',4',5'-trimethoxybiphenyl |
| 264 | N | 2,5-dimethoxy-4-methylphenyl | 2-methoxy-5-methyl-phenyl-(furan-3-yl) |
| 265 | N | 2,3-dimethoxy-6-methoxy-4-methylphenyl | 2-methoxy-5-methyl-3'-aminobiphenyl |
| 266 | N | 2,3-dimethoxy-6-methoxy-4-methylphenyl | 2-methoxy-5-methyl-4'-phenoxybiphenyl |
| 267 | N | 2,3-dimethoxy-6-methoxy-4-methylphenyl | 2-methoxy-5-methyl-phenyl-(thiophen-3-yl) |
| 268 | N | 2,3-dimethoxy-6-methoxy-4-methylphenyl | 2-methoxy-5-methyl-3'-(NHCOCH₃)biphenyl |
| 269 | N | 2,3-dimethoxy-6-methoxy-4-methylphenyl | 2-methoxy-5-methyl-4'-ethoxybiphenyl |

TABLE 1-continued

| Compound No. | Y | R₁ | R₂ |
|---|---|---|---|
| 270 | N | 2,3-dimethoxy-4-methoxyphenyl (H₃CO, OCH₃, OCH₃ on benzene with methyl) | 2-methoxy-5-methyl-phenyl-(pyridin-3-yl) |
| 271 | N | 2,3-dimethoxy-4-methoxyphenyl | 2-methoxy-5-methyl-phenyl-(4-hydroxymethylphenyl) |
| 272 | N | 2,3-dimethoxy-4-methoxyphenyl | 2-methoxy-5-methyl-phenyl-(furan-2-yl) |
| 273 | N | 2,3-dimethoxy-4-methoxyphenyl | 2-methoxy-5-methyl-phenyl-(benzo[1,3]dioxol-5-yl) |
| 274 | N | 2,3-dimethoxy-4-methoxyphenyl | 2-methoxy-5-methyl-phenyl-(pyridin-4-yl) |
| 275 | N | 2,3-dimethoxy-4-methoxyphenyl | 2-methoxy-5-methyl-phenyl-(3,4-dimethoxyphenyl) |
| 276 | N | 2,3-dimethoxy-4-methoxyphenyl | 2-methoxy-5-methyl-phenyl-(2-hydroxyphenyl) |

TABLE 1-continued
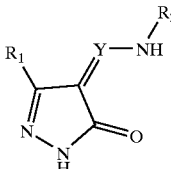
| Compound No. | Y | R₁ | R₂ |
|---|---|---|---|
| 277 | N | 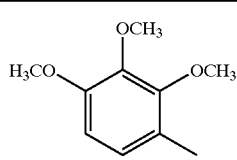 | 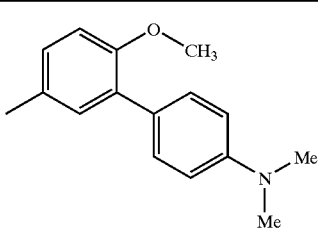 |
| 278 | N | 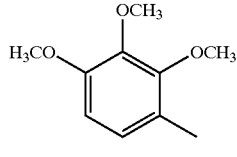 | 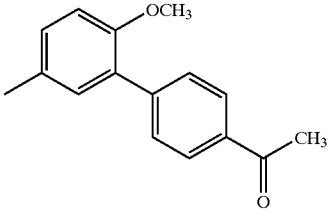 |
| 279 | N | 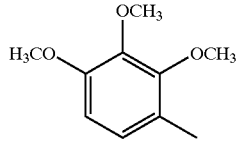 | 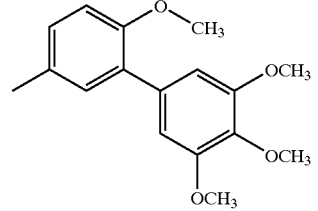 |
| 280 | N | 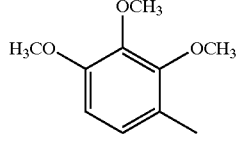 | 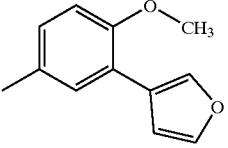 |
| 281 | N | 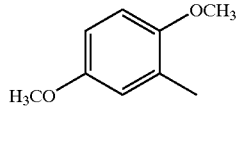 | 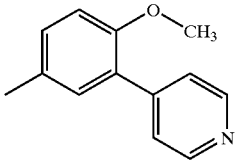 |
| 282 | N | 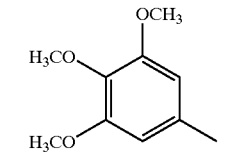 | 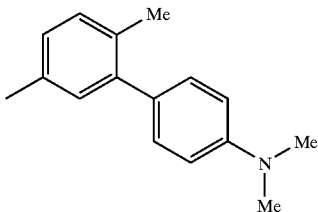 |

TABLE 1-continued

| Compound No. | Y | R₁ | R₂ |
|---|---|---|---|
| 283 | N | 3,4-dimethoxyphenyl | 2'-(trifluoromethoxy)-3,4-dimethoxy-biphenyl-methyl |
| 284 | N | 3,4,5-trimethoxyphenyl | 2-methyl-5-(furan-2-yl)phenyl |
| 285 | N | 3,4-dimethoxyphenyl | 2-methyl-5-(furan-3-yl)phenyl |
| 286 | N | 2,4-dimethoxyphenyl | 2'-(trifluoromethoxy)-3'-ethoxy-biphenyl |
| 287 | N | 2,4-dimethoxyphenyl | 2'-(trifluoromethoxy)-4'-(hydroxymethyl)-biphenyl |
| 288 | N | 2,4-dimethoxyphenyl | 2'-methoxy-3'-amino-biphenyl |
| 289 | N | 3,4,5-trimethoxyphenyl | 2'-methoxy-3',4',5'-trimethoxy-biphenyl |

TABLE 1-continued

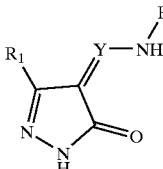

| Compound No. | Y | R₁ | R₂ |
|---|---|---|---|
| 290 | N | 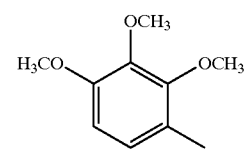 | 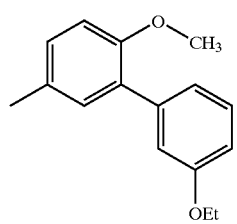 |

The exemplary compounds of this invention generally may be prepared from known starting materials, following methods known to those skilled in the art for analogous compounds, as illustrated by general Schemes I–III.

Scheme I

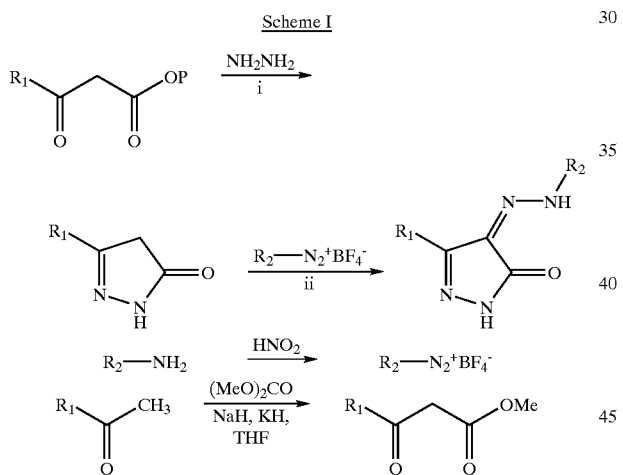

Scheme I shows a general approach for making the present compounds. The starting material β-keto esters were either commercially available or readily synthesized following methods known in the art, for instance, those described in Jung, M. E., Lau, P., Mansuri, M. M. and Speltz, L. M., *J. Org. Chem.*, 50, 1087 (1985). Step (i) was carried out following the method as described in Zauhar, J. and Ladoucheur, B. F., *Can. J. Chem.*, 46, 1079 (1968) and step (ii) was carried out following the method as described in Zollinger, H. *Color Chemistry: Synthesis, Properties and Applications of Organic Dyes and Pigments*, 2$^{nd}$ ed., VCH, pp. 109–180 (1991).

In certain embodiments of the invention, compounds of formula I can be prepared from the reagents ($R_1COCH_3$ and $R_2$—$NH_2$) depicted below in Tables 2A and 2B.

TABLE 2A

Exemplary Reagents - $R_1COCH_3$

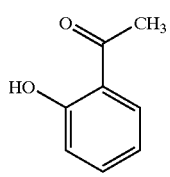

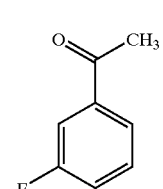

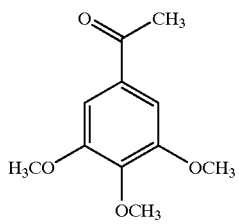

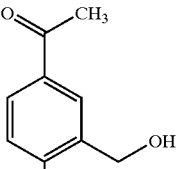

TABLE 2A-continued
Exemplary Reagents - R₁COCH₃
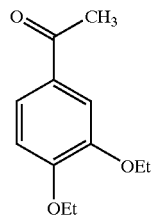
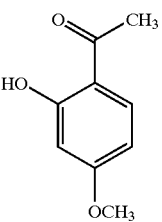
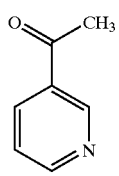
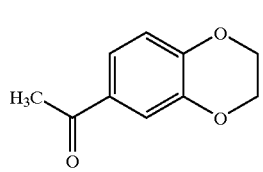
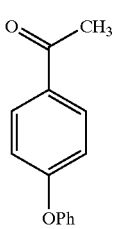
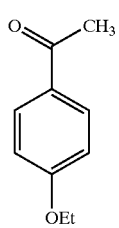
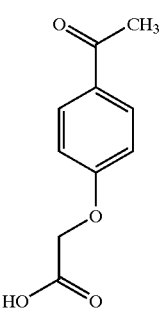
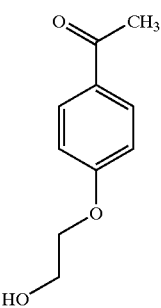
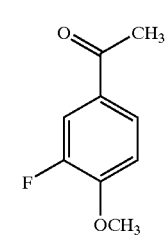
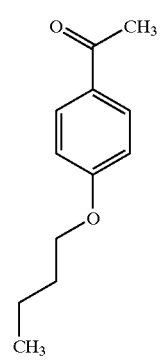
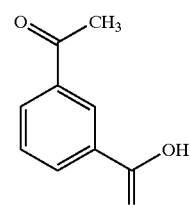
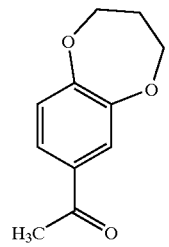

TABLE 2A-continued
Exemplary Reagents - R₁COCH₃
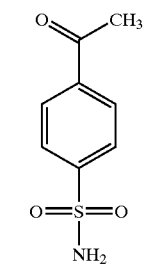
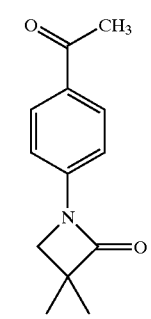
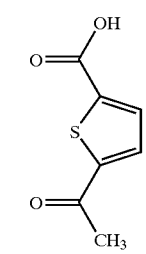
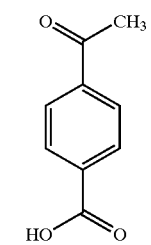
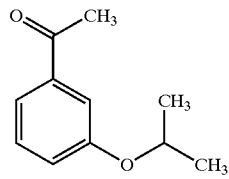
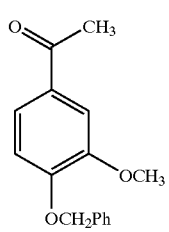
TABLE 2A-continued
Exemplary Reagents - R₁COCH₃
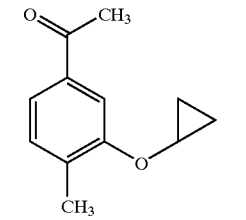
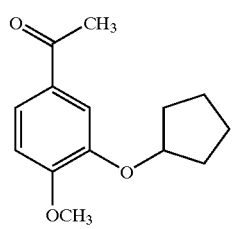
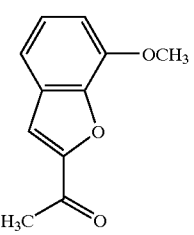
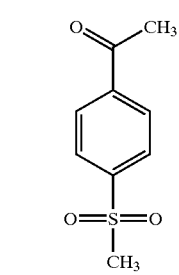
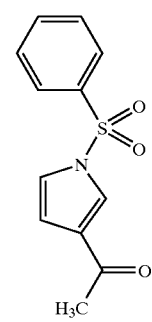
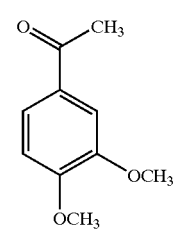

TABLE 2A-continued
Exemplary Reagents - R₁COCH₃
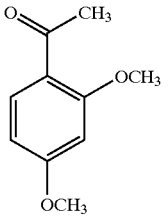
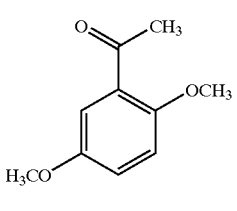
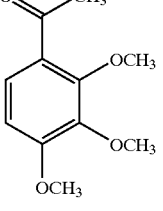
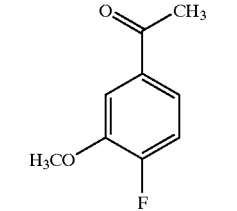
TABLE 2B
Exemplary Reagents - R₂—NH₂
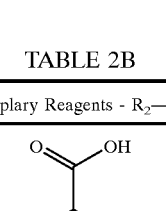
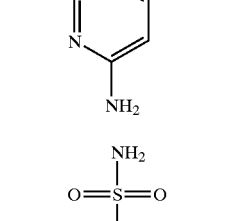
TABLE 2B-continued
Exemplary Reagents - R₂—NH₂
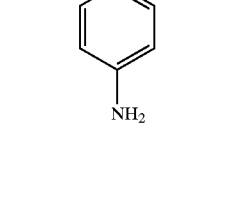
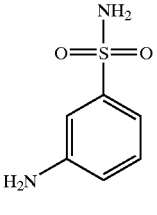
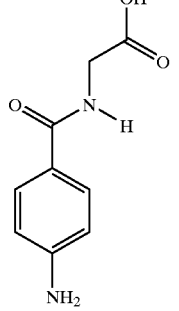
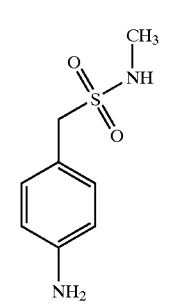
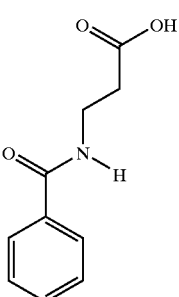

TABLE 2B-continued
Exemplary Reagents - R₂—NH₂
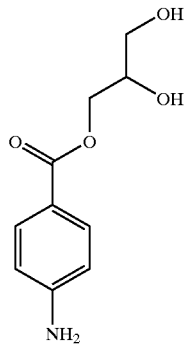
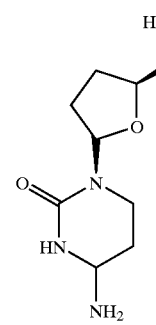
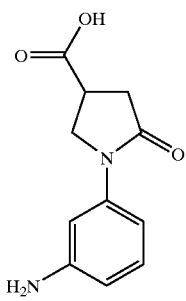
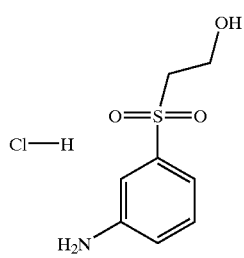
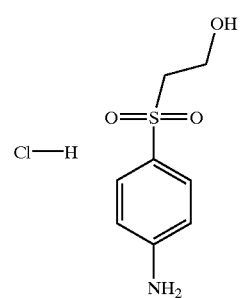
TABLE 2B-continued
Exemplary Reagents - R₂—NH₂
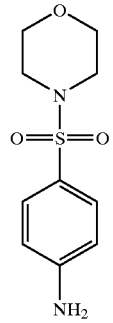
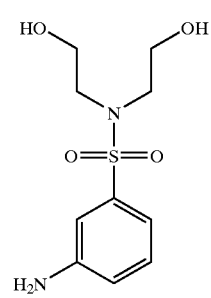
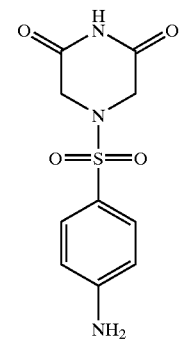
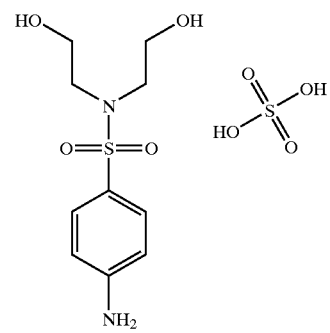
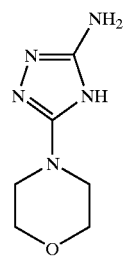

TABLE 2B-continued

Exemplary Reagents - R$_2$—NH$_2$

TABLE 2B-continued
Exemplary Reagents - R$_2$—NH$_2$
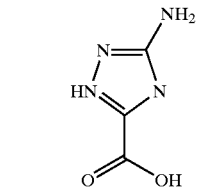
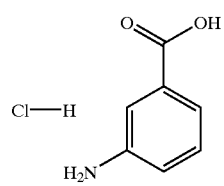
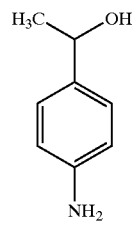
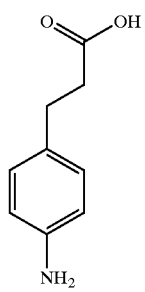
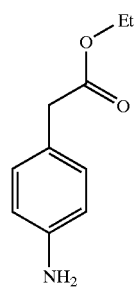
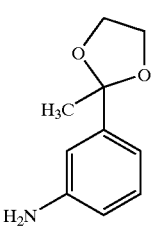
TABLE 2B-continued
Exemplary Reagents - R$_2$—NH$_2$
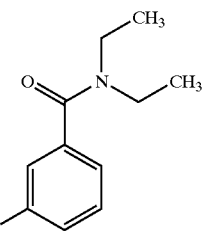
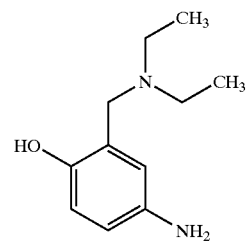
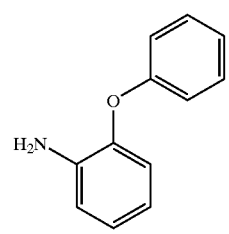
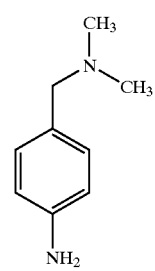
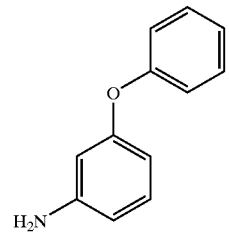
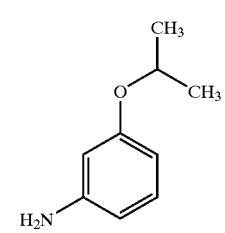

TABLE 2B-continued
Exemplary Reagents - $R_2$—$NH_2$
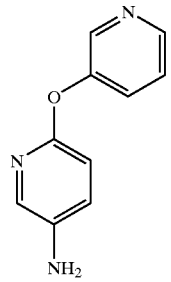
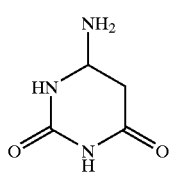
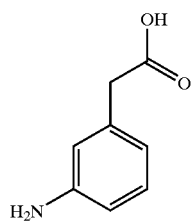
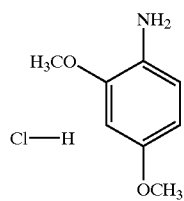
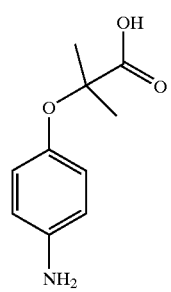
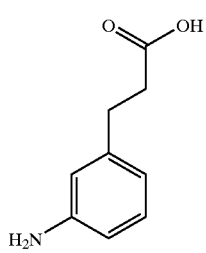
TABLE 2B-continued
Exemplary Reagents - $R_2$—$NH_2$
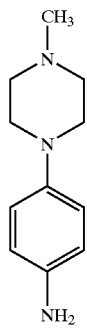
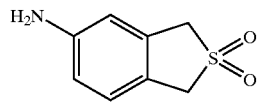
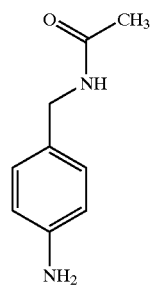
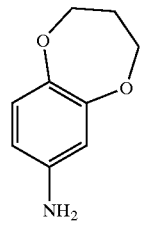
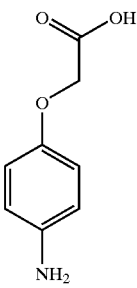
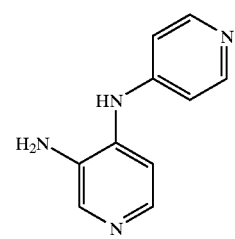

TABLE 2B-continued
Exemplary Reagents - R$_2$—NH$_2$
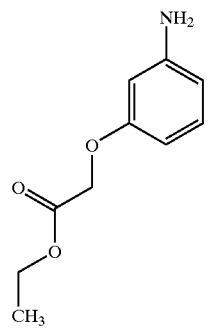
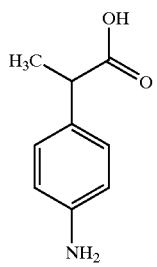
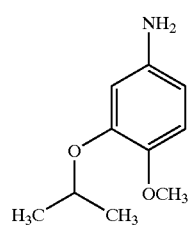
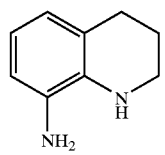
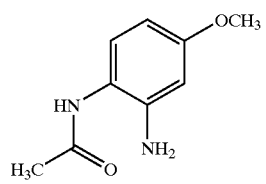
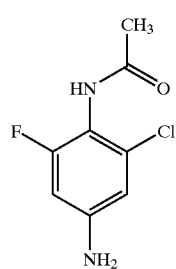
TABLE 2B-continued
Exemplary Reagents - R$_2$—NH$_2$
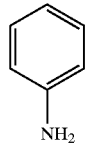
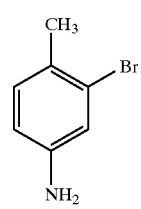
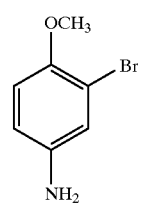
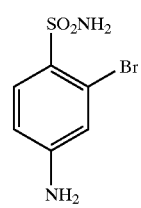
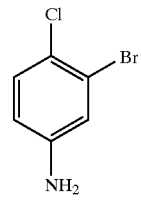
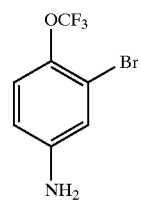

Scheme II

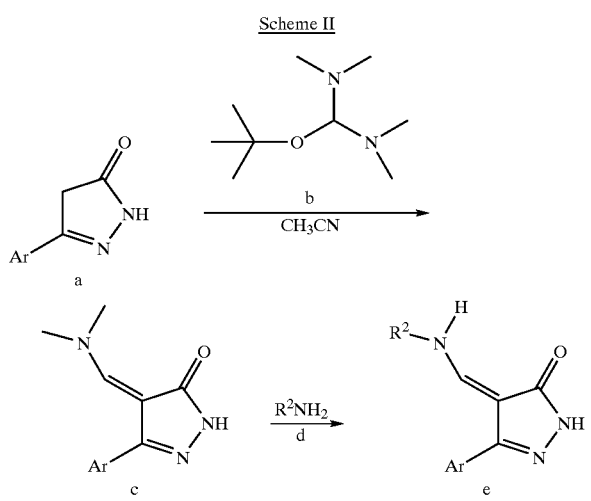

Scheme II shows a general synthetic route that is used for preparing the compounds of formula I where Y is CH and $R^1$ is aryl (denoted as Ar in Scheme II).

5-Aryl-2,4-dihydro-pyrazol-3-one (a) in dry actonitrile was added C-tert-butoxy-N,N,N',N'-tetramethylmethanediamine (b) and stirred. The reaction was monitored by HPLC. After 36 hours, the solid (c) was filtered and rinsed with dry acetonitrile and dried under nitrogen pressure.

4-Dimethylaminomethylene-5-aryl-2,4-dihydro-pyrazol-3-one (c) was combined with amine (d) in acetonitrile and heated to reflux for 8~16 hours with/without catalytic amount of acetic acid. The reaction was monitored by HPLC. After the reaction was complete, the mixture was kept at room temperature to form solid. The product (e) was filtered and washed with acetonitrile/methanol. The details of the conditions used for producing these compounds are set forth in the Examples.

Scheme III

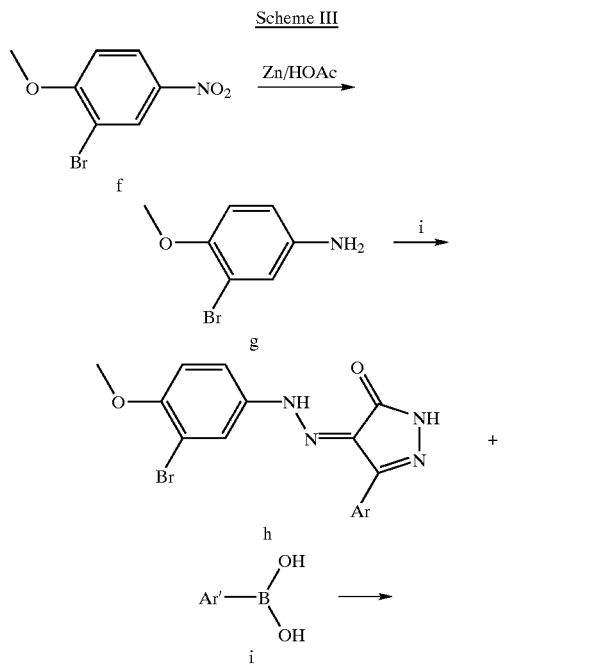

-continued

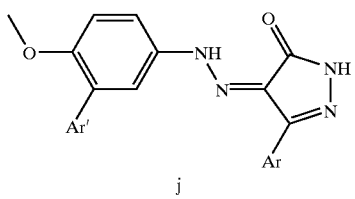

Scheme III above shows a general synthetic route that is used for preparing the compounds of formula I where X is NH, Y is N, $R^1$ is aryl (denoted as Ar in Scheme III) and $R^2$ is an Ar' substituted anisole (Ar' denotes an aryl) by Suzuki coupling which was described by O'Neill et al., *J. Med. Chem.*, 40, pp. 437–448 (1997).

Step i was carried out following the method as described in Zollinger, H. *Color Chemistry: Synthesis, Properties and Applications of Organic Dyes and Pigments*, $2^{nd}$ ed., VCH, pp. 109–180 (1991). After the aryl bromide (h, 50 mg, 0.11 mmol) was partially dissolved in toluene (1 mL), ethanol (0.2 mL) and several drops of water, sodium carbonate (24 mg, 0.22 mmol), an aromatic boronic acid (i, 0.12 mmol) and tetrakis(triphenylphosphine) palladium (12 mg) were subsequently added. The reaction tube was sealed and heated to 100° C. for 5–12 hours. After cooling, several mL of brine were added and the mixture was extracted with methylene chloride. The solvent was dried and removed. The residue was then purified by silica gel chromatography or reverse phase HPLC to give the product (j). Exemplary aromatic boronic acids (i) are depicted below in Table 3.

TABLE 3

Exemplary Aromatic Boronic Acids i

TABLE 3-continued
Exemplary Aromatic Boronic Acids i
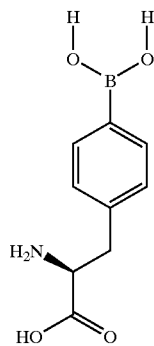
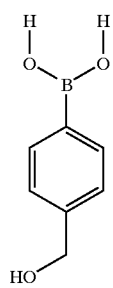
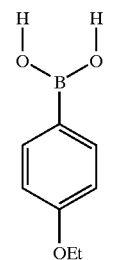
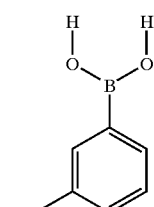
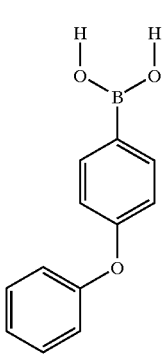
TABLE 3-continued
Exemplary Aromatic Boronic Acids i
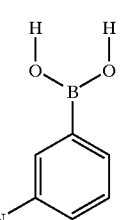
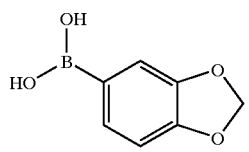
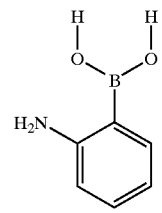
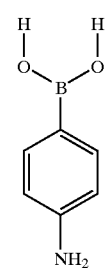
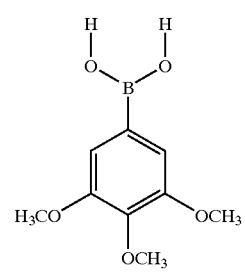
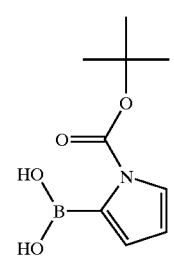

TABLE 3-continued

Exemplary Aromatic Boronic Acids i

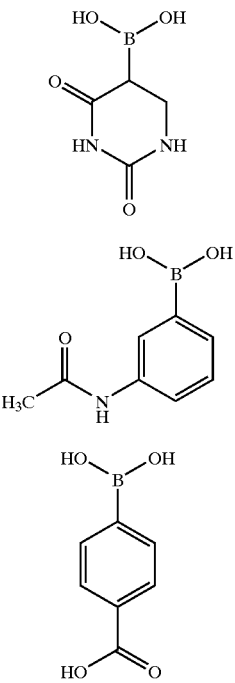

One having ordinary skill in the art may synthesize other compounds of this invention following the teachings of the specification using reagents that are readily synthesized or commercially available.

Another object of the instant invention is to provide methods for inhibiting GSK-3 activity comprising the step of administering compounds having formula (I).

The activity of the compounds as protein kinase inhibitors, particularly as GSK-3 inhibitors, may be assayed in vitro, in vivo or in a cell line. In vitro assays include assays that determine inhibition of either the phosphorylation activity or ATPase activity of activated GSK-3. Alternate in vitro assays quantitate the ability of the inhibitor to bind to GSK-3. Inhibitor binding may be measured by radiolabelling the inhibitor prior to binding, isolating the inhibitor/GSK-3 complex and determining the amount of radiolabel bound. Alternatively, inhibitor binding may be determined by running a competition experiment where new inhibitors are incubated with GSK-3 bound to known radioligands.

The compounds of the present invention may also be effective as Aurora protein kinase inhibitors or cyclin-dependent kinases, particularly as Aurora-2 or CDK-2 inhibitors. Accordingly, these compounds are useful for treating or preventing Aurora-2- or CDK-2-mediated conditions and in methods for inhibiting Aurora-2 or CDK-2 activity.

The activity of the compounds as Aurora-2 or CDK-2 inhibitors may be assayed in vitro, in vivo or in a cell line using similar procedures as described above for GSK-3.

According to one embodiment of the invention, compounds of formula I or salts thereof may be formulated into compositions. In a preferred embodiment, the composition is a pharmaceutical composition. In one embodiment, the composition comprises an amount of the protein kinase inhibitor effective to inhibit a protein kinase, particularly GSK-3, in a biological sample or in a patient. In another embodiment, compounds of this invention and pharmaceutical compositions thereof, which comprise an amount of the protein kinase inhibitor effective to treat or prevent a GSK-3-mediated condition and a pharmaceutically acceptable carrier, adjuvant, or vehicle, may be formulated for administration to a patient.

Another aspect of this invention relates to a method of enhancing glycogen synthesis and/or lowering blood levels of glucose in a patient in need thereof, which method comprises administering to the patient a therapeutically effective amount of a compound of formula I or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of the invention relates to inhibiting GSK-3 activity in a biological sample, which method comprises contacting the biological sample with the GSK-3 inhibitor of formula I.

Another aspect of this invention relates to a method of inhibiting Aurora-2 activity in a patient, which method comprises administering to the patient a compound of formula I or a composition comprising said compound.

Another aspect of this invention relates to a method for treating or preventing an Aurora-2-mediated disease state with an Aurora-2 inhibitor, which method comprises administering to a patient in need of such a treatment a therapeutically effective amount of a compound of formula I or a pharmaceutical composition thereof.

Another aspect of the invention relates to inhibiting Aurora-2 activity in a biological sample, which method comprises contacting the biological sample with the Aurora-2 inhibitor of formula I, or a composition thereof.

Another aspect of the invention relates to inhibiting CDK-2 activity in a biological sample or a patient, which method comprises administering to the patient a compound of formula I or a composition comprising said compound.

Another aspect of this invention relates to a method for treating or preventing a CDK-2-mediated disease state with a CDK-2 inhibitor, which method comprises administering to a patient in need of such a treatment a therapeutically effective amount of a compound of formula I or a pharmaceutical composition thereof.

The term "pharmaceutically acceptable carrier, adjuvant, or vehicle" refers to a non-toxic carrier, adjuvant, or vehicle that may be administered to a patient, together with a compound of this invention, and which does not destroy the pharmacological activity thereof.

The term "patient" includes human and veterinary subjects.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

The term "GSK-3-mediated condition" or "state", as used herein, means any disease or other deleterious condition or state in which GSK-3, in particular GSK-3, is known to play a role. Such diseases or conditions include, without limitation, diabetes, Alzheimer's disease, Huntington's Disease, Parkinson's Disease, AIDS-associated dementia, amyotrophic lateral sclerosis (AML), multiple sclerosis (MS), schizophrenia, cardiomycete hypertrophy, reperfusion/ischemia, and baldness.

The term "Aurora-2-mediated condition" or "state", as used herein, means any disease or other deleterious condition in which Aurora is known to play a role. Such conditions include, without limitation, cancer. The term "cancer" includes, but is not limited to the following cancers: colon and ovarian.

The term "CDK-2-mediated condition" or "state", as used herein, means any disease or other deleterious condition in which CDK-2 is known to play a role. Such conditions include, without limitation, cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis.

The amount effective to inhibit protein kinase, for example, GSK-3, Aurora-2 and CDK-2, is one that inhibits the kinase activity at least 50%, more preferably at least 60% or 70%, even more preferably at least 80% or 90%, and most preferably at least 95%, where compared to the activity of the enzyme in the absence of an inhibitor. Any method may be used to determine inhibition. See, e.g., Examples 1–3.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, favoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In addition to the compounds of this invention, pharmaceutically acceptable derivatives or prodrugs of the compounds of this invention may also be employed in compositions to treat or prevent the above-identified diseases or disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization.

The amount of the protein kinase inhibitor that may be combined with the carrier materials to produce a single dosage form will vary depending upon the patient treated and the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of the inhibitor will also depend upon the particular compound in the composition.

Depending upon the particular protein kinase-mediated condition to be treated or prevented, additional drugs, which are normally administered to treat or prevent that condition, may be administered together with the inhibitors of this invention. For example, in the treatment of diabetes other anti-diabetic agents may be combined with the GSK-3 inhibitors of this invention to treat diabetes. These agents include, without limitation, insulin, in injectable or inhalation form, glitazones, and sulfonyl ureas.

Those additional agents may be administered separately from the protein kinase inhibitor-containing composition, as part of a multiple dosage regimen. Alternatively, those agents may be part of a single dosage form, mixed together with the protein kinase inhibitor of this invention in a single composition.

In order that the invention described herein may be more fully understood, the following examples are set forth. It should be understood that these examples are for illustrative purposes only and are not to be construed as limiting this invention in any manner.

EXAMPLE 1

$K_i$ Determination for the Inhibition of GSK-3

Compounds were screened for their ability to inhibit GSK-3β (AA 1-420) activity using a standard coupled enzyme system (Fox et al. (1998) *Protein Sci.* 7, 2249). Reactions were carried out in a solution containing 100 mM HEPES (pH 7.5), 10 mM $MgCl_2$, 25 mM NaCl, 300 μM NADH, 1 mM DTT and 1.5% DMSO. Final substrate concentrations in the assay were 20 μM ATP (Sigma Chemicals, St Louis, Mo.) and 300 μM peptide (HSSPHQS $(PO_3H_2)$EDEEE, American Peptide, Sunnyvale, Calif.). Reactions were carried out at 30° C. and 20 nM GSK-3β. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and the test compound of interest. The assay stock buffer solution (175 μl) was incubated in a 96 well plate with 5 μl of the test compound of interest at final concentrations spanning 0.002 μM to 30 μM at 30 ° C. for 10 min. Typically, a 12 point titration was conducted by preparing serial dilutions (from 10 mM compound stocks) with DMSO of the test compounds in daughter plates. The reaction was initiated by the addition of 20 μl of ATP (final concentration 20 μM). Rates of reaction were obtained using a Molecular Devices Spectramax plate reader (Sunnyvale, Calif.) over 10 min at 30° C. The $K_i$ values were determined from the rate data as a function of inhibitor concentration.

The following compounds were shown to have $K_i$ values less than 0.1 μM for GSK-3: compounds 18–25, 36–37, 43–75, 77–78, 80, 82–83, 85–90, 97–98, 105–106, 109, 120–126, 203–208, 213, 217–218, 220, 223, and 225.

The following compounds were shown to have $K_i$ values between 0.1 and 1.0 μM for GSK-3: compounds 8, 12, 14–17, 26–27, 33, 38, 40, 76, 84, 91–93, 95–96, 111–113, 224, and 227.

The following compounds were shown to have $K_i$ values between 1.0 and 20 μM for GSK-3: compounds 1–7, 9–11, 13, 28–32, 34–35, 39, 41–42, 79, 81, 103, 212, 215–216, 219, 222, and 226.

EXAMPLE 2

$K_i$ Determination for the Inhibition of Aurora-2

Compounds were screened in the following manner for their ability to inhibit Aurora-2 using a standard coupled enzyme assay (Fox et al. (1998) *Protein Sci.* 7, 2249).

To an assay stock buffer solution containing 0.1M HEPES 7.5, 10 mM $MgCl_2$, 1 mM DTT, 25 mM NaCl, 2.5 mM phosphoenolpyruvate, 300 mM NADH, 30 mg/ml pyruvate kinase, 10 mg/ml lactate dehydrogenase, 40 mM ATP, and 800 $\mu$M peptide (LRRASLG, American Peptide, Sunnyvale, Calif.) was added a DMSO solution of a compound of the present invention to a final concentration of 30 $\mu$M. The resulting mixture was incubated at 30° C. for 10 min. The reaction was initiated by the addition of 10 $\mu$L of Aurora-2 stock solution to give a final concentration of 70 nM in the assay. The rates of reaction were obtained by monitoring absorbance at 340 nm over a 5 minute read time at 30° C. using a BioRad Ultramark plate reader (Hercules, Calif.). The Ki values were determined from the rate data as a function of inhibitor concentration.

The following compounds were shown to have $K_i$ values less than 0.1 $\mu$M for Aurora-2: compounds 22–23, 37, 47, 52, 61, 73, 86, 114–116, 118–119, and 223.

The following compounds were shown to have $K_i$ values between 0.1 and 1.0 $\mu$M for Aurora-2: compounds 43, 46, 58, 60, 62, 70, and 117.

The following compounds were shown to have $K_i$ values between 1.0 and 20 $\mu$M for Aurora-2: compounds 18–21, 33, 36, 44, 45, 48–51, 53–57, 59, 63–69, 71–72, 74–75, 77–78, 80, 82–83, 85, 87–90, 203–208, and 213.

EXAMPLE 3

The Inhibition of CDK-2

Compounds were screened in the following manner for their ability to inhibit CDK-2 using a standard coupled enzyme assay (Fox et al (1998) *Protein Sci* 7, 2249).

To an assay stock buffer solution containing 0.1M HEPES 7.5, 10 mM $MgCl_2$, 1 mM DTT, 25 mM NaCl, 2.5 mM phosphoenolpyruvate, 300 mM NADH, 30 mg/ml pyruvate kinase, 10 mg/ml lactate dehydrogenase, 100 mM ATP, and 100 $\mu$M peptide (MAHHHRSPRKRAKKK, American Peptide, Sunnyvale, Calif.) was added a DMSO solution of a compound of the present invention to a final concentration of 30 $\mu$M. The resulting mixture was incubated at 30° C. for 10 min. The reaction was initiated by the addition of 10 $\mu$L of CDK-2/Cyclin A stock solution to give a final concentration of 25 nM in the assay. The rates of reaction were obtained by monitoring absorbance at 340 nm over a 5-minute read time at 30° C. using a BioRad Ultramark plate reader (Hercules, Calif.). The $K_i$ values were determined from the rate data as a function of inhibitor concentration.

The CDK-2 inhibitory activity of certain compounds of this invention is shown in Table 4.

TABLE 4

Inhibitory Activity of CDK-2

| Compound No. | CDK-2 | |
|---|---|---|
| | % inhibition @ 10 $\mu$M | % inhibition @ 2 $\mu$M |
| 44 | 94 | 87 |
| 46 | 95 | 82 |

Compound 98 was shown to have $K_i$ values between 0.1 and 1.0 $\mu$M for CDK-2.

The following compounds were shown to have $K_i$ values between 1.0 and 20 $\mu$M for CDK-2: compounds 91–93, 95–97, 106, 114–119, and 120–122.

EXAMPLE 4

As used hereinafter, the term "$R_t$(min)" refers to the HPLC retention time, in minutes, associated with a particular compound. HPLC analysis utilized to obtain the reported retention time was performed with HP1100 HPLC and analysis method was 8 minutes overal run with 0 minute, 10% B; 1 minute, 30% B; 5 minutes, 90% B; 6.5 minutes, 90% B; and 6.7 minutes, 10% B. A: 0.01% TFA in water, B: 0.01% TFA in acetonitrile. Analytical column was YMC ODS-AQ, 30×100 mm with 1 mL/min flow rate using diodo ray detector (5 wavelength were monitored at 300, 280, 254, 220, and 210 nm) at 25° C.

Preparation of 5-(3,4,5-Trimethoxyphenyl)-2,4-Dihydro-Pyrazol-3-one (k):

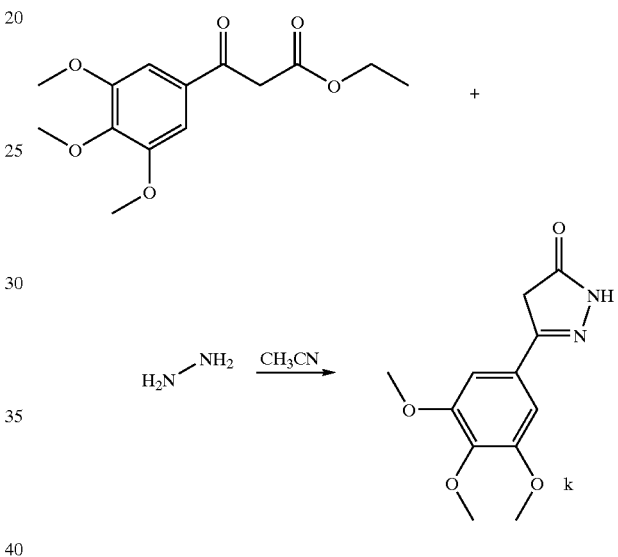

To a stirred solution of 3-oxo-3-(3,4,5-trimethoxyphenyl)-propionic acid ethyl ester (2.82 g, 10 mmol) in dry acetonitrile (15 mL) was added to anhydrous hydrazine (640 mL, 20 mmol) at room temperature. After 1 hour, the mixture was heated to reflux for 16 hours. The mixture was diluted with acetonitrile (20 mL) and the solid was filtered. The solid was washed with acetonitrile (10 mL) and dried under nitrogen to afford 2.2 g of title compound (k).

Preparation of 4-Dimethylaminomethylene-5-(3,4,5-Trimethoxyphenyl)-2,4-Dihydro-Pyrazol-3-one (1):

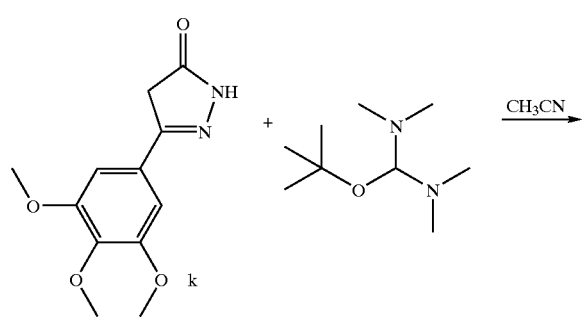

-continued

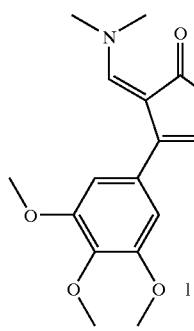

5-(3,4,5-Trimethoxyphenyl)-2,4-dihydro-pyrazol-3-one (k, 2 g) in dry actonitrile (10 mL) was added C-tert-Butoxy-N,N,N',N'-tetramethyl-methanediamine (3 mL) and stirred at 35° C. The reaction was monitored by HPLC. After 36 hours, the solid was filtered and rinsed with dry acetonitrile (5 mL) and dried under nitrogen pressure to yield the title compound (1).

The same method was used for the preparation of 4-dimethylaminomethylene-5-(3,4-dimethoxyphenyl)-2,4-dihydro-pyrazol-3-one.

Compounds 91–104 were prepared by using the synthetic routes as outlined in Scheme II and analogous methods as described above.

Compound 92: 4-[(3-Benzyloxy-phenylamino)-methylene]-5-(3,4-dimethoxy-phenyl)-2,4-dihydro-pyrazol-3-one HPLC ($R_t$): 4.767 minutes; MS: 429.17, [M+H]: 430.2; $^1$H NMR (500 MHz, DMSO-$d_6$): 8.48 (brs, 1H), 7.24–7.47 (m, 9H), 7.03 (d, J=8.4 Hz, 2H), 6.85 (dd, J=8.2 and 2.1 Hz, 1H), 5.15 (s, 2H), 3.82 (s, 3H) and 3.81 (s, 3H).

Compound 94: 4-[(2,3-Dihydro-benzo[1,4]dioxin-6-ylamino)-methylene]-5-(3,4,5-trimethoxy-phenyl)-2, 4-dihydro-pyrazol-3-one HPLC ($R_t$): 3.776 minutes; MS: 411.14, [M+H]: 412.2, [M−H]: 410.5; $^1$H NMR(500 MHz, DMSO-$d_6$) 11.9 (brs, 1H), 11.50 (s, 1H), 8.41 (s, 1H), 7.15 (d, J=2.5 Hz, 1H), 6.93 (m, 3H), 6.88 (d, J=8.6Hz, 1H), 4.25 (m, 4H), 3.85 (s, 6H, 2×CH$_3$) and 3.70 (s, 3H, CH$_3$).

Compound 95: 3-{[3-(3,4-Dimethoxy-phenyl)-5-oxo-1,5-dihydro-pyrazol-4-ylidenemethyl]-amino}-benzenesulfonamide HPLC ($R_t$): 2.67 and 3.07 minutes; MS: 402.10, [M+H]: 403.0, [M−H]: 401.0; $^1$H NMR (500 MHz, DMSO-$d_6$) 8.50 (s, 1H), 7.84 (s, 1H), 7.78 (m, 1H), 7.61 (d, J=4.6 Hz, 2H), 7.43 (s, 2H), 7.30 (d, J=8.3 Hz, 1H), 7.28 (s, 1H), 7.04 (d, J=8.3 Hz, 1H), 3.83 (s, 3H) and 3.82 (s, 3H).

Compound 99: 4-Phenylaminomethylene-5-(3,4,5-trimethoxy-phenyl)-2,4-dihydro-pyrazol-3-one HPLC ($R_t$): 5.75 minutes; m/e: 353, MS (ES+): 354.3; $^1$H NMR (500 MHz, CDCl$_3$): 11.7 (bs, 1H), 9.0 (s, 1H), 7.5 (m, 2H), 7.3 (m, 4H), 6.8 (s, 2H), 3.95 (s, 6H) and 3.9 (s, 3H).

Compound 100: 4-Cyclohexylaminomethylene-5-(3, 4,5-trimethoxy-phenyl)-2,4-dihydro-pyrazol-3-one HPLC ($R_t$): 5.69 minutes; m/e: 359.3, MS (ES+): 360.3; $^1$H NMR (500 MHz, CDCl$_3$): 10.0 (bs, 1H), 9.8 (s, 1H), 7.6 (d, J=10 Hz, 1H), 6.7 (s, 1H), 4.85 (s, 6H), 4.80 (s, 3H), 3.2 (bs, 1H) and 2.0–1.0 (m, 10H).

EXAMPLE 5

Compounds 105–110 were prepared by following the synthetic route as outlined in Scheme III.

Compound 105: 4-[(3'-Amino-6-methoxy-biphenyl-3-yl)-hydrazono]-5-(3,4-dimethoxy-phenyl)-2,4-dihydro-pyrazol-3-one HPLC ($R_t$): 5.11 minutes; m/e: 445.18, MS (ES+): 446.2.

Compound 106: 5-(3,4-Dimethoxy-phenyl)-4-[(4-methoxy-3-pyridin-3-yl-phenyl)-hydrazono]-2,4-dihydro-pyrazol-3-one HPLC ($R_t$): 4.95 minutes; m/e: 431.16, MS (ES+): 432.1.

Compound 107: 5-(3,4-Dimethoxy-phenyl)-4-[(4-methoxy-3-pyridin-4-yl-phenyl)-hydrazono]-2,4-dihydro-pyrazol-3-one HPLC ($R_t$): 4.773 minutes; m/e: 431.16, MS (ES+): 432.1.

Compound 108: 5-(3,4-Dimethoxy-phenyl)-4-[(3'-hydroxymethyl-6-methoxy-biphenyl-3-yl)-hydrazono]-2,4-dihydro-pyrazol-3-one HPLC ($R_t$): 6.563 minutes; m/e: 460.18, MS (ES+): 461.2.

Compound 109: 5-(3,4-Dimethoxy-phenyl)-4-[(6,3', 4',5'-tetramethoxy-biphenyl-3-yl)-hydrazono]-2,4-dihydro-pyrazol-3-one HPLC ($R_t$): 7.350 minutes; m/e: 520.2, MS (ES+): 521.2.

Compound 110: 5-(3,4-Dimethoxy-phenyl)-4-[(4'-dimethylamino-6-methoxy-biphenyl-3-yl)-hydrazono]-2,4-dihydro-pyrazol-3-one HPLC ($R_t$): 5.452 minutes; m/e: 473.21, MS (ES+): 474.1.

EXAMPLE 6

Compounds 111–116 were prepared by following the synthetic method as outlined in Scheme I.

Compound 111: 4-[(2,5-Diethoxy-4-morpholin-4-yl-phenyl)-hydrazono]-5-(3,4-dimethoxy-phenyl)-2,4-dihydro-pyrazol-3-one HPLC ($R_t$): 6.453 minutes; m/e: 497.22, MS (ES+): 498.3.

Compound 112: 5-(3,4-Dimethoxy-phenyl)-4-[(2,4, 6-trimethoxy-phenyl)-hydrazono]-2,4-dihydro-pyrazol-3-one HPLC ($R_t$): 6.584 minutes; m/e: 414.15, MS (ES+): 415.2.

Compound 113: 5-(4-Hydroxy-3-methoxy-phenyl)-4-[(2-methoxy-4-morpholin-4-yl-phenyl)-hydrazono]-2,4-dihydro-pyrazol-3-one HPLC ($R_t$): 5.420 minutes; m/e: 425.16, MS (ES+): 426.3.

Compound 114: 5-(3,4-Diethoxy-phenyl)-4-[(4-diethylamino-phenyl)-hydrazono]-2,4-dihydro-pyrazol-3-one HPLC ($R_t$): 5.340 minutes; m/e: 423.23, MS (ES+): 424.2.

Compound 115: 5-(3,4-Diethoxy-phenyl)-4-({4-[ethyl-(2-hydroxy-ethyl)-amino]-phenyl}-hydrazono)-2,4-dihydro-pyrazol-3-one HPLC ($R_t$): 4.942 minutes; m/e: 439.99, MS (ES+): 440.2.

Compound 116: 5-(3,4-Diethoxy-phenyl)-4-[(4-morpholin-4-yl-phenyl)-hydrazono]-2,4-dihydro-pyrazol-3-one HPLC ($R_t$): 6. 771 minutes; m/e: 437.21, MS (ES+): 438.1.

EXAMPLE 7

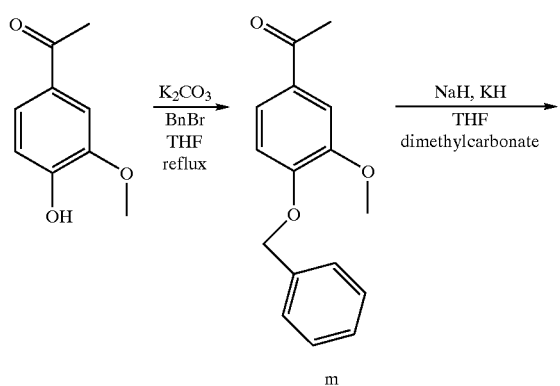

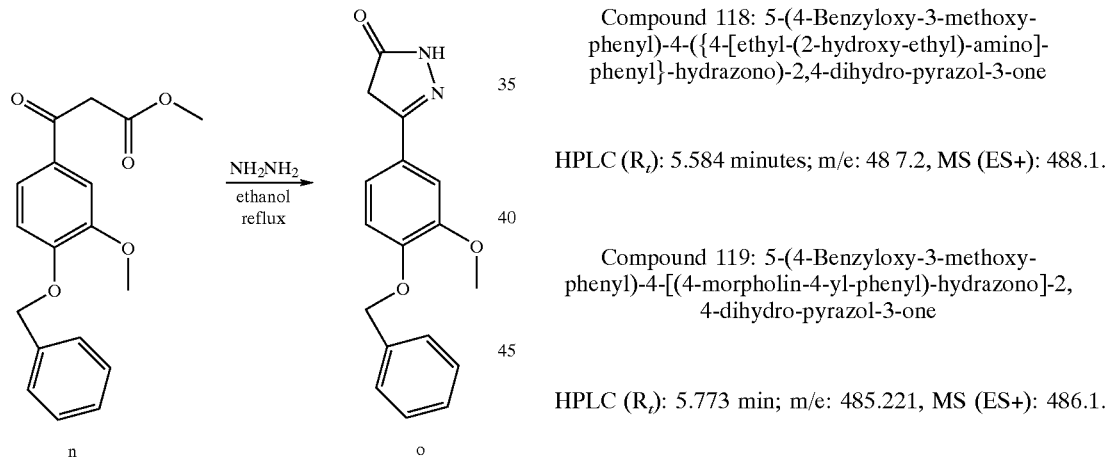

1-(4-Benzyloxy-3-methoxy-phenyl)-ethanone (m) was prepared and characterized as described in *J. Org. Chem.*, 57, p. 7248 (1992).

5-(4-Benzyloxy-3-methoxy-phenyl)-2,4-dihydro-pyrazol-3-one (o) was prepared from 1-(4-benzyloxy-3-methoxy-phenyl)-ethanone (m) using the method as described in Scheme I. 3-(4-Benzyloxy-3-methoxy-phenyl)-3-oxo-propionic acid methyl ester (n): m/e: 314.12, MS (ES+): 315.0. 5-(4-Benzyloxy-3-methoxy-phenyl)-2,4-dihydro-pyrazol-3-one (o): m/e: 296.12, MS (ES+): 297.0; $^1$H NMR (500 MHz, DMSO-$d_6$): 12.0 (bs, 1H), 9.8 (bs, 1H), 7.5–7.0 (m, 8H), 5.9 (s, 1H), 5.1 (s, 2H) and 3.8 (s, 3H).

Compounds 117–119 were prepared from 5-(4-benzyloxy-3-methoxy-phenyl)-2,4-dihydro-pyrazol-3-one (o) using the method as described in Scheme I.

Compound 117: 5-(4-Benzyloxy-3-methoxy-phenyl)-4-[(4-diethylamino-phenyl)-hydrazono]-2,4-dihydro-pyrazol-3-one HPLC ($R_t$): 5.945 minutes; m/e: 471.23, MS (ES+): 472.1.

Compound 118: 5-(4-Benzyloxy-3-methoxy-phenyl)-4-({4-[ethyl-(2-hydroxy-ethyl)-amino]-phenyl}-hydrazono)-2,4-dihydro-pyrazol-3-one HPLC ($R_t$): 5.584 minutes; m/e: 48 7.2, MS (ES+): 488.1.

Compound 119: 5-(4-Benzyloxy-3-methoxy-phenyl)-4-[(4-morpholin-4-yl-phenyl)-hydrazono]-2,4-dihydro-pyrazol-3-one HPLC ($R_t$): 5.773 min; m/e: 485.221, MS (ES+): 486.1.

EXAMPLE 8

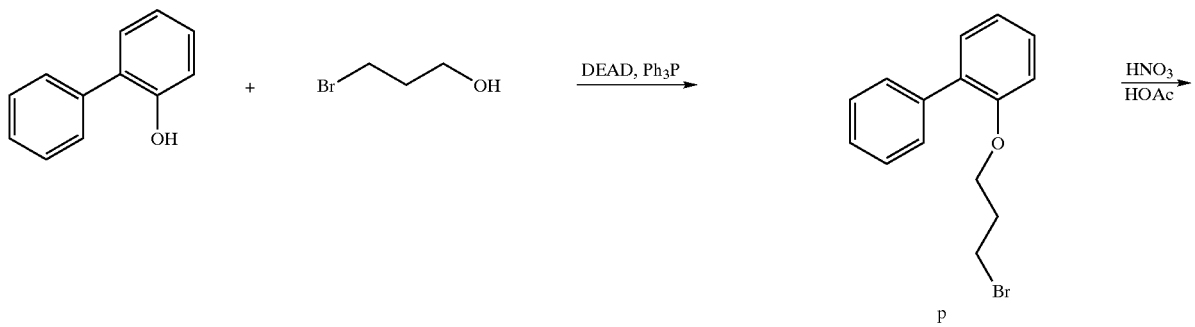

127
128
-continued
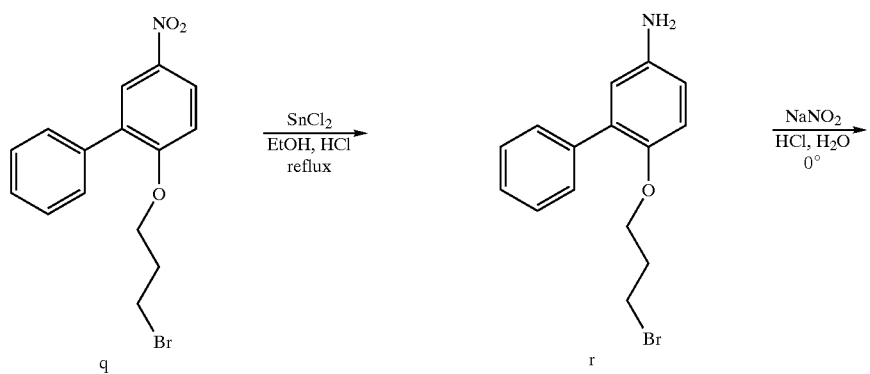
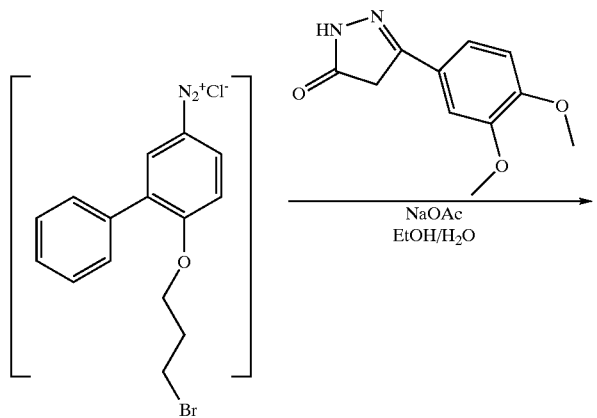
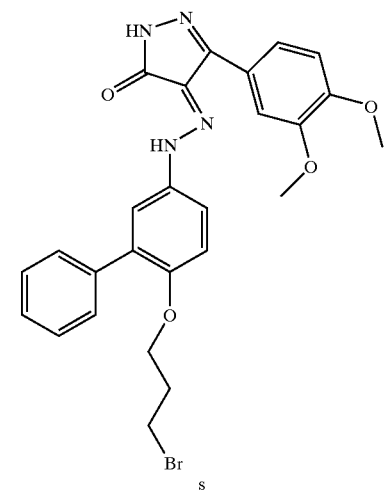
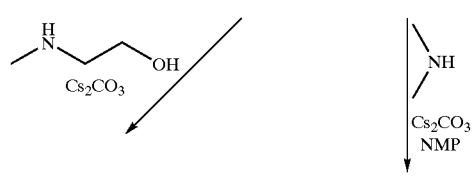

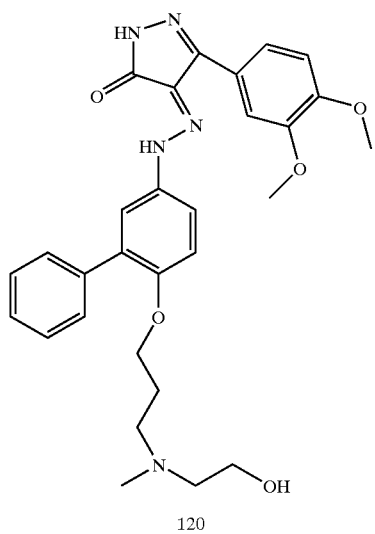

120

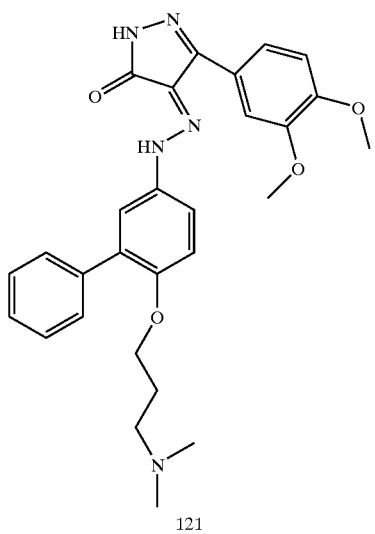

121

2-(3-Bromo-propoxy)-biphenyl (p) was prepared by treating biphenyl-2-ol (6.2 g, 36 mmol) and 3-bomopropanol (5 g, 36 mmol) with DEAD (6.3 g, 36 mmol) and triphenyl phosphine (9.5 g, 36 mmol) in 100 mL THF at room temperature overnight. The solvent was then evaporated. The crude product was purified by silica gel chromatography (eluent: 5% ethylacetate, 50% DCM, 45% hexane) to afford p in 50% yield: $^1$H NMR (500 MHz, CDCl$_3$): 7.6–6.9 (m, 9H), 4.1 (m, 2H), 3.5 (m, 2H) and 2.2 (m, 2H).

The bromide p (6 g, 26 mmol) from the previous step was nitrated in 10 ml acetic acid and 5 mL nitric acid at 0° C. After 2 hours, the reaction mixture was poured into 100 mL water and the product mixture was filtered and washed with water. The crude product was purified by silica gel chromatography (eluent: DCM) affording 3 g 2-(3-bromo-propoxy)-5-nitro-biphenyl (q) in 45% yield: $^1$H NMR (500 MHz, CDCl$_3$): 8.2 (m, 2H), 7.3 (m, 5H), 6.9 (m, 1H), 4.2 (m, 2H), 3.3 (m, 2H) and 2.2 (2H).

2-(3-Bromo-propoxy)-5-nitro-biphenyl (q, 530 mg, 1.57 mmol) was refluxed with stannous chloride hydrate (1.1 g, 4.8 mmol) in 5 mL ethanol and 3 mL concentrated HCl. After 1.5 hours, the solvent was evaporated and the mixture was basified with 2N NaOH. The mixture was then extracted with DCM, dried and evaporated, affording 250 mg 6-(3-bromo-propoxy)-biphenyl-3-ylamine (r) in 50% yield: $^1$H NMR (500 MHz, CDCl$_3$): 7.3 (m, 5H), 6.7 (m, 3H), 4.2 (bs, 2H), 3.9 (m, 2H), 3.5 (m, 2H) and 2.1 (2H).

6-(3-Bromo-propoxy)-biphenyl-3-ylamine (r, 250 mg, 0.82 mmol) was diazotized with sodium nitrite (67 mg, 0.98 mmol) in 1:1 water/ethanol and 0.5 mL concentrated HCl at 0° C. After approximately 1 hour, the diazonium solution was added dropwise to a suspension of 5-(3,4-dimethoxy-phenyl)-2,4-dihydro-pyrazol-3-one (200 mg, 0.9 mmol) and sodium acetate (1.1 g) in 10 mL 1:1 water/ethanol. The orange solid which precipitated was filtered and washed with water and dried. The crude product was purified by silica gel chromatography (eluent: 5% methanol/DCM) to afford 120 mg of 4-{[6-(3-bromo-propoxy)-biphenyl-3-yl]-hydrazono}-5-(3,4-dimethoxy-phenyl)-2,4-dihydro-pyrazol-3-one (s): HPLC (R$_t$) 5.02 min; m/e 536.1, MS (ES+): 538.9; $^1$H NMR (500 MHz, CDCl$_3$): 13.9 (bs, 1H), 9.0 (bs, 1H), 7.7–6.9 (m, 11H), 4.1 (m, 2H), 3.9 (s, 3H), 3.7 (s, 3H), 3.5 (m, 2H), 3.3 (m, 2H), 2.2 (m, 2H) and 2.1 (m, 2H).

5-(3,4-Dimethoxy-phenyl)-4-{[6-(3-dimethylamino-propoxy)-biphenyl-3-yl]-hydrazono}-2,4-dihydro-pyrazol-3-one (compound 121) was prepared by dissolving 4-{[6-(3-bromo-propoxy)-biphenyl-3-yl]-hydrazono}-5-(3,4-dimethoxy-phenyl)-2,4-dihydro-pyrazol-3-one (s) in 1 mL of a dimethylamine solution (2 M in THF) and heating to 50° C. for one hour. The solvent was then evaporated and the residue was purified by silica gel chromatography (eluent: 10% methanol/DCM) to afford 6 mg product (compound 121): HPLC (R$_t$): 5.490 minutes; m/e: 501.23, MS (ES+): 502.2.

4-{[6-(3-Bromo-propoxy)-biphenyl-3-yl]-hydrazono}-5-(3,4-dimethoxy-phenyl)-2,4-dihydro-pyrazol-3-one (s) and Cs$_2$CO$_3$ were dissolved in 1 mL (2-hydoxy)ethylmethyl amine and the resulting solution was heated to 50° C. for one hour. The solvent was evaporated and the residue was purified by silica gel chromatography (eluent: 10% methanol/DCM) to afford 15 mg 5-(3,4-dimethoxy-phenyl)-4-[(6-{3-[(2-hydroxy-ethyl)-methyl-amino]-propoxy}-biphenyl-3-yl)-hydrazono]-2,4-dihydro-pyrazol-3-one (compound 120): HPLC (R$_t$): 5.525 minutes; m/e: 531.24, MS (ES+): 532.2.

EXAMPLE 9

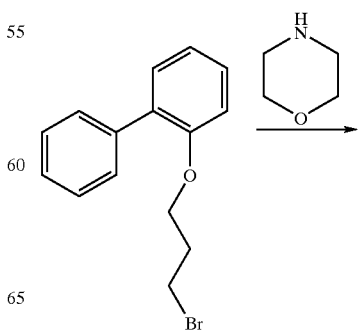

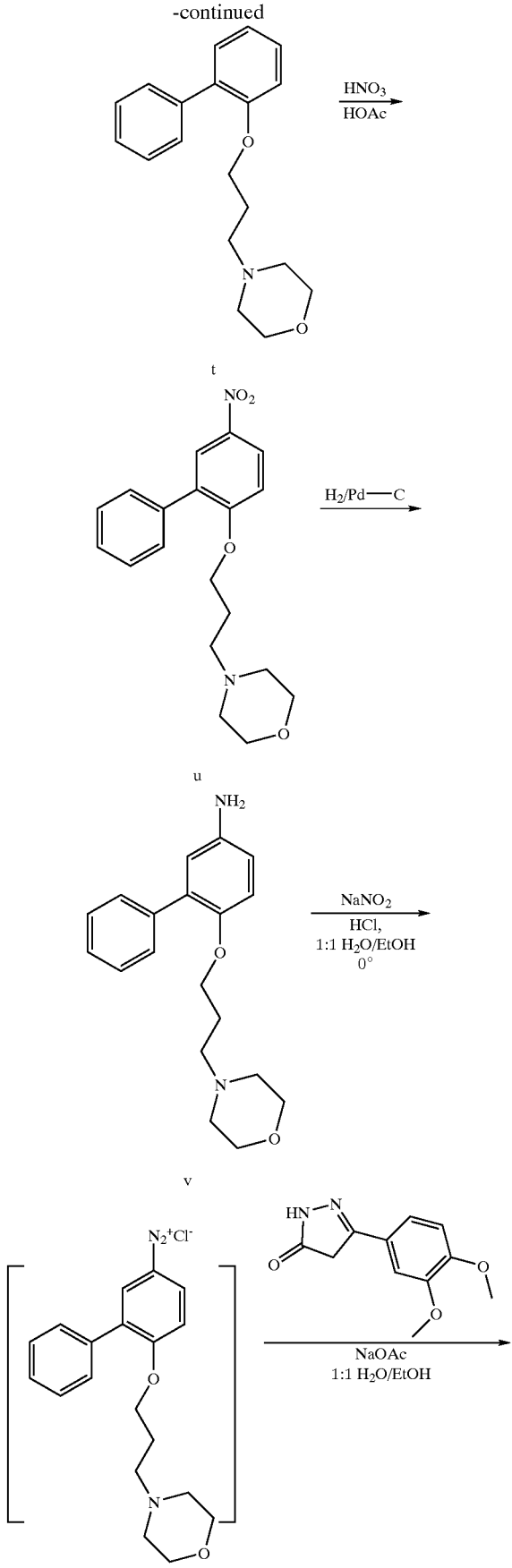

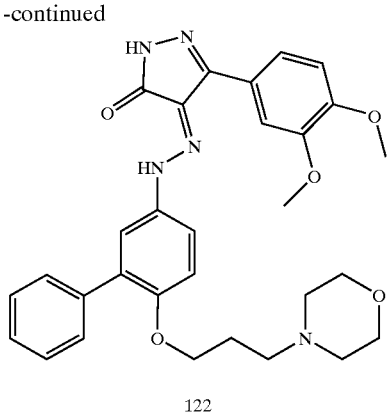

122

2-(3-Bromo-propoxy)-biphenyl (1.0 g) was reacted with morpholine (5 mL) at 50° C. for 1 hour to form 4-[3-(biphenyl-2-yloxy)-propyl]-morpholine. The excess morpholine was evaporated and water was added, followed by extraction with ethyl acetate. Removal of ethyl acetate afforded 900 mg of 4-[3-(biphenyl-2-yloxy)-propyl]-morpholine (t) as an oil which was used without further purification: m/e: 297.17, MS (ES+): 298.2; $^1$H NMR (500 MHz, CDCl$_3$): 7.8–7.0 (m, 9H), 4.0 (m, 2H), 3.7 (m, 4H), 2.5 (m, 6H) and 1.8 (m, 2H).

4-[3-(Biphenyl-2-yloxy)-propyl]-morpholine (t, 500 mg, 1.46 mmol) was dissolved in 3 mL acetic acid and the reaction mixture was cooled in an ice bath. Concentrated nitric acid (3 mL) was added dropwise and the mixture was stirred for 15 minutes at 0° C., then at room temperature for one hour. The reaction was subsequently poured into 100 mL water and the pH of the reaction mixture was raised to >7 with 2N NaOH. The aqueous solution was extracted with ethyl acetate and dried. The solvent was then removed to afford 500 mg 4-[3-(5-nitro-biphenyl-2-yloxy)-propyl]-morpholine (u) which was used without further purification: m/e: 342.15, MS (ES+): 343.1; $^1$H NMR (500 MHz, CDCl$_3$): 8.2–6.8 (m, 9H), 4.1(m, 2H), 3.7 (m, 4H), 2.5 (m, 6H) and 1.8 (m, 2H).

4-[3-(5-Nitro-biphenyl-2-yloxy)-propyl]-morpholine (u, 400 mg, 1.1 mmol) was dissolved in 10 mL ethanol and hydrogenated at 1 atm. using 10% Pd—C as a catalyst. After the reaction was allowed to stir overnight, the reaction mixture was filtered and the solvent was evaporated. The residue was purified by silica gel chromatography (eluent: 5% methanol/DCM) to afford 160 mg 6-(3-morpholin-4-yl-propoxy)-biphenyl-3-ylamine (v): m/e: 312.18, MS (ES+): 313.2.

6-(3-Morpholin-4-yl-propoxy)-biphenyl-3-ylamine (v, 160 mg, 0.51 mmol) was diazotized with sodium nitrite (43 mg, 0.62 mmol) in 1:1 water/ethanol and 0.5 mL concentrated HCl at 0° C. After approximately 1 hour, the diazonium solution was added dropwise to a suspension of 5-(3,4-dimethoxy-phenyl)-2,4-dihydro-pyrazol-3-one (120 mg, 0.51 mmol) and sodium acetate 1.1 g in 10 mL 1:1 water/ethanol. The orange solid which precipitated was filtered and washed with water and dried. The product was purified by silica gel chromatography (eluent: 5% methanol:DCM) to afford 150 mg of 4-{[6-(3-bromo-propoxy)-biphenyl-3-yl]-hydrazono}-5-(3,4-dimethoxy-phenyl)-2,4-dihydro-pyrazol-3-one (compound 122) in 55% yield: HPLC (R$_t$): 5.552 minutes; m/e: 543.24, MS (ES+): 544.2.

EXAMPLE 10

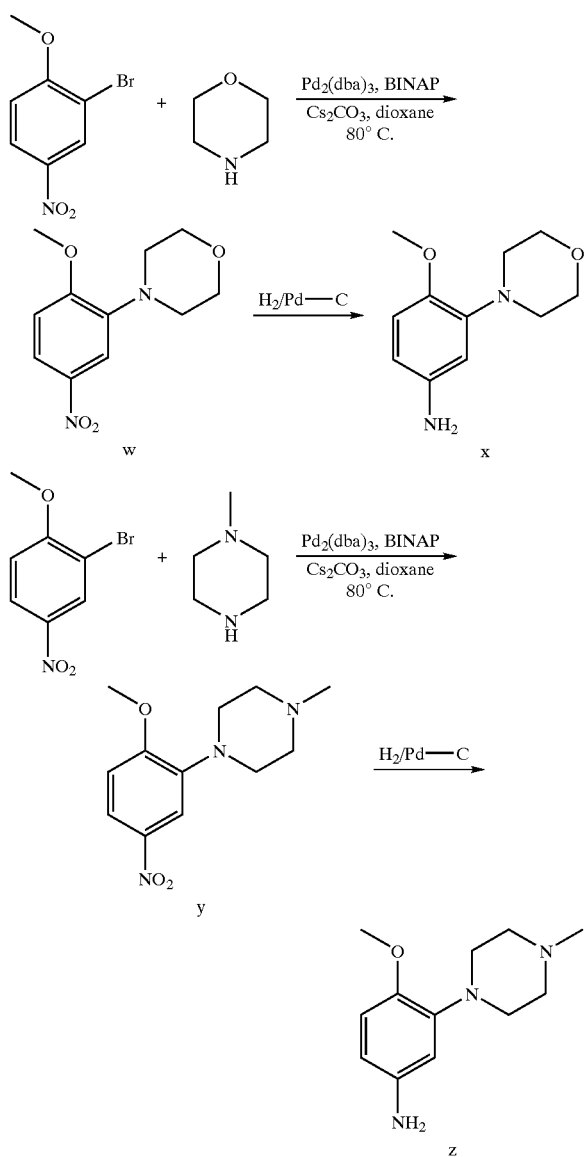

Compounds x and z were prepared following the method as described by Buchwald et al., *J. Org. Chem.* 65, pp. 1158–1174 (2000).

2-Bromo-1-methoxy-4-nitro-benzene (810 mg, 4 mmol), morpholine (420 µL, 4.8 mmol), cesium carbonate (1.8 g, 5.6 mmol), $Pd_2(dba)_3$ (75 mg, 0.02 mmol) and BINAP (75 mg, 0.03 mmol) were added to 5 mL dry dioxane under an argon atmosphere and heated to 80° C. for 6 hours. After cooling, the solvent was evaporated and the residue was purified by silica gel chromatagraphy (eluent: 5% MeOH/DCM) to afford 390 mg 4-(2-methoxy-5-nitro-phenyl)-morpholine (w): m/e: 238.09, MS (ES+): 239.3 $^1$H NMR (500 MHz, $CDCl_3$): 8.0 (d, J=10 Hz, 1H), 7.8 (s, 1H), 6.9 (d, J=10 Hz, 1H), 4.1 (s, 3H), 3.9 (m, 4H) and 3.2(m, 4H).

4-(2-Methoxy-5-nitro-phenyl)-morpholine (w, 390 mg) was dissolved in 10 mL ethanol and reduced under 1 atm $H_2$ using 10% Pd—C as a catalyst. After 14 hours, the catalyst was filtered off and the solvent was evaporated, affording 240 mg 4-methoxy-3-morpholin-4-yl-phenylamine (x) which was used without further purification: m/e: 208.12, MS (ES+): 209.2.

4-Methoxy-3-(4-methyl-piperazin-1-yl)-phenylamine (z) was prepared in a similar fashion. 1-(2-Methoxy-5-nitro-phenyl)-4-methyl-piperazine (y): m/e: 251.12, MS (ES+): 252.2. 4-Methoxy-3-(4-methyl-piperazin-1-yl)-phenylamine (z): m/e: 221.1, MS (ES+): 222.2.

Using the general diazotization and coupling procedures described earlier, compounds 123–126 were prepared from compound x or z.

Compound 123: 5-(3,4-Dimethoxy-phenyl)-4-[(4-methoxy-3-morpholin-4-yl-phenyl)-hydrazono]-2,4-dihydro-pyrazol-3-one HPLC ($R_t$): 5.631 minutes; m/e: 439.18, MS (ES+): 440.2.

Compound 124: 4-[(4-Methoxy-3-morpholin-4-yl-phenyl)-hydrazono]-5-(3,4,5-trimethoxy-phenyl)-2,4-dihydro-pyrazol-3-one HPLC ($R_t$): 5.841 minutes; m/e: 469.19, MS (ES+): 470.2.

Compound 125: 5-(3,4-Dimethoxy-phenyl)-4-{[4-methoxy-3-(4-methyl-piperazin-1-yl)-phenyl]-hydrazono}-2,4-dihydro-pyrazol-3-one HPLC ($R_t$): 4.638 minutes; m/e: 452.21, MS (ES+): 453.3.

Compound 126: 5-(4-Benzyloxy-3-methoxy-phenyl)-4-{[4-methoxy-3-(4-methyl-piperazin-1-yl)-phenyl]-hydrazono}-2,4-dihydro-pyrazol-3-one HPLC ($R_t$): 5.937 minutes; m/e: 528.24, MS (ES+): 529.3.

EXAMPLE 11

Compounds 127–132 were prepared by following the method as described in Scheme I.

Compound 127: 4-[(4-Chloro-phenyl)-hydrazono]-5-(6-methoxy-pyridin-3-yl)-2,4-dihydro-pyrazol-3-one HPLC ($R_t$): 3.787 minutes; m/e: 328.9, MS (ES+): 329.9.

Compound 128: 4-[(4-Methoxy-phenyl)-hydrazono]-5-(6-methoxy-pyridin-3-yl)-2,4-dihydro-pyrazol-3-one HPLC ($R_t$): 3.469 minutes; m/e: 325.02, MS (ES+): 326.02.

Compound 129: 4-[(3-Bromo-phenyl)-hydrazono]-5-(6-methoxy-pyridin-3-yl)-2,4-dihydro-pyrazol-3-one HPLC ($R_t$): 3.819 minutes; m/e: 374.99, MS (ES+): 375.99.

Compound 130: 5-(6-Methoxy-pyridin-3-yl)-4-(pyridin-3-yl-hydrazono)-2,4-dihydro-pyrazol-3-one HPLC ($R_t$): 2.252 minutes; m/e: 296.11, MS (ES+): 297.11.

Compound 131: 5-(4-Methoxy-phenyl)-4-(pyridin-3-yl-hydrazono)-2,4-dihydro-pyrazol-3-one HPLC ($R_t$): 2.695 minutes; m/e: 295.1, MS (ES+): 296.1.

Compound 132: 4-{[4-(4-Methyl-piperazin-1-yl)-phenyl]-hydrazono}-5-(3,4,5-trimethoxy-phenyl)-2,4-dihydro-pyrazol-3-one HPLC ($R_t$): 2.695 minutes (100%); m/e: 452.4, MS (ES+): 453.4.

EXAMPLE 12

Compounds 133–162 were prepared by following the methods as described herein.

Compound 133: 4-[(6-Methoxy-biphenyl-3-yl)-hydrazono]-5-(3,4,5-trimethoxy-phenyl)-2,4-dihydro-pyrazol-3-one HPLC ($R_t$): 1.562 minutes; m/e: 460.44, MS (ES+): 461.44.

Compound 134: 5-(3,4-Dimethoxy-phenyl)-4-[(6-methoxy-biphenyl-3-yl)-hydrazono]-2,4-dihydro-pyrazol-3-one HPLC ($R_t$): 1.520 minutes; m/e: 430.4, MS (ES+): 431.41.

Compound 135: 5-(3,4-Dimethoxy-phenyl)-4-[(6-methoxy-biphenyl-3-yl)-hydrazono]-2,4-dihydro-pyrazol-3-one HPLC ($R_t$): 1.528 minutes; m/e: 430.29, MS (ES+): 431.29.

Compound 136: 4-[(6-Methoxy-biphenyl-3-yl)-hydrazono]-5-(2,3,4-trimethoxy-phenyl)-2,4-dihydro-pyrazol-3-one HPLC ($R_t$): 1.910 minutes; m/e: 460.28, MS (ES+): 461.28.

Compound 137: 5-(3,4-Dimethoxy-phenyl)-4-[(2-methoxy-biphenyl-4-yl)-hydrazono]-2,4-dihydro-pyrazol-3-one HPLC ($R_t$): 1.546 minutes; m/e: 430.5, MS (ES+): 431.50.

Compound 138: 4-[(2-Methoxy-biphenyl-4-yl)-hydrazono]-5-(3,4,5-trimethoxy-phenyl)-2,4-dihydro-pyrazol-3-one HPLC ($R_t$): 1.639 minutes; m/e: 460.34, MS (ES+): 461.34.

Compound 139: 5-(2,4-Dimethoxy-phenyl)-4-[(2-methoxy-biphenyl-4-yl)-hydrazono]-2,4-dihydro-pyrazol-3-one HPLC ($R_t$): 1.539 minutes; m/e: 430.48, MS (ES+): 431.48.

Compound 140: 5-(2,5-Dimethoxy-phenyl)-4-[(2-methoxy-biphenyl-4-yl)-hydrazono]-2,4-dihydro-pyrazol-3-one HPLC ($R_t$): 1.591 minutes; m/e: 430.33, MS (ES+): 431.33.

Compound 141: 4-[(2-Methoxy-biphenyl-4-yl)-hydrazono]-5-(2,3,4-trimethoxy-phenyl)-2,4-dihydro-pyrazol-3-one HPLC ($R_t$): 1.584 minutes; m/e: 460.33, MS (ES+): 461.33.

Compound 142: 4-[(3'-Amino-6-methyl-biphenyl-3-yl)-hydrazono]-5-(3,4,5-trimethoxy-phenyl)-2,4-dihydro-pyrazol-3-one HPLC ($R_t$): 1.157 minutes; m/e: 459.26, MS (ES+): 460.26.

Compound 143: 4-[(4-Methyl-3-thiophen-3-yl-phenyl)-hydrazono]-5-(3,4,5-trimethoxy-phenyl)-2,4-dihydro-pyrazol-3-one HPLC ($R_t$): 1.657 minutes; m/e: 450.25, MS (ES+): 451.25.

Compound 144: N-(2'-Methyl-5'-{N'-[5-oxo-3-(3,4,5-trimethoxy-phenyl)-1,5-dihydro-pyrazol-4-ylidene]-hydrazino}-biphenyl-3-yl)-acetamide HPLC ($R_t$): 1.384 minutes; m/e: 501.28, MS (ES+): 502.28.

Compound 145: 4-[(4'-Ethoxy-6-methyl-biphenyl-3-yl)-hydrazono]-5-(3,4,5-trimethoxy-phenyl)-2,4-dihydro-pyrazol-3-one HPLC ($R_t$): 1.764 minutes; m/e: 488.29, MS (ES+): 489.29.

Compound 146: 4-[(4-Methyl-3-pyridin-3-yl-phenyl)-hydrazono]-5-(3,4,5-trimethoxy-phenyl)-2,4-dihydro-pyrazol-3-one HPLC ($R_t$): 1.077 minutes; m/e: 445.27, MS (ES+): 446.27.

Compound 147: 4-[(3-Benzo[1,3]dioxol-5-yl-4-methyl-phenyl)-hydrazono]-5-(3,4,5-trimethoxy-phenyl)-2,4-dihydro-pyrazol-3-one HPLC ($R_t$): 1.636 minutes; m/e: 488.24, MS (ES+): 489.24.

Compound 148: 4-[(4-Methyl-3-pyridin-4-yl-phenyl)-hydrazono]-5-(3,4,5-trimethoxy-phenyl)-2,4-dihydro-pyrazol-3-one HPLC ($R_t$): 1.071 minutes; m/e: 445.27, MS (ES+): 446.27.

Compound 149: 4-[(4'-Acetyl-6-methyl-biphenyl-3-yl)-hydrazono]-5-(3,4,5-trimethoxy-phenyl)-2,4-dihydro-pyrazol-3-one HPLC ($R_t$): 1.551 minutes; m/e 486.30, MS (ES+): 487.30.

Compound 150: 4-[(3',4',5'-Trimethoxy-6-methyl-biphenyl-3-yl)-hydrazono]-5-(3,4,5-trimethoxy-phenyl)-2,4-dihydro-pyrazol-3-one HPLC ($R_t$): 1.538 minutes; m/e: 534.32, MS (ES+): 535.32.

Compound 151: 4-[(3'-Amino-6-methyl-biphenyl-3-yl)-hydrazono]-5-(2,4-dimethoxy-phenyl)-2,4-dihydro-pyrazol-3-one HPLC ($R_t$): 1.151 minutes; m/e: 429.29, MS (ES+): 430.29.

Compound 152: 5-(2,4-Dimethoxy-phenyl)-4-[(4'-hydroxymethyl-6-methyl-biphenyl-3-yl)-hydrazono]-2,4-dihydro-pyrazol-3-one HPLC ($R_t$): 1.360 minutes; m/e 444.29, MS (ES+): 445.29.

Compound 153: 4-[(3-Benzo[1,3]dioxol-5-yl-4-methyl-phenyl)-hydrazono]-5-(2,4-dimethoxy-phenyl)-2,4-dihydro-pyrazol-3-one HPLC ($R_t$): 1.587 minutes; m/e: 458.27, MS (ES+): 459.27.

Compound 154: 5-(2,4-Dimethoxy-phenyl)-4-[(3',4',5'-trimethoxy-6-methyl-biphenyl-3-yl)-hydrazono]-2,4-dihydro-pyrazol-3-one HPLC ($R_t$): 1.511 minutes; m/e: 504.32, MS (ES+): 505.32.

Compound 155: 5-(2,5-Dimethoxy-phenyl)-4-[(6-methyl-4'-phenoxy-biphenyl-3-yl)-hydrazono]-2,4-dihydro-pyrazol-3-one HPLC ($R_t$): 1.842 minutes; m/e: 506.29, MS (ES+): 507.29.

Compound 156: N-(5'-{N'-[3-(2,5-Dimethoxy-phenyl)-5-oxo-1,5-dihydro-pyrazol-4-ylidene]-hydrazino}-2'-methyl-biphenyl-3-yl)-acetamide HPLC ($R_t$): 1.316 minutes; m/e: 471.56, MS (ES+): 472.56.

Compound 157: 5-(2,5-Dimethoxy-phenyl)-4-[(4'-ethoxy-6-methyl-biphenyl-3-yl)-hydrazono]-2,4-dihydro-pyrazol-3-one HPLC ($R_t$): 1.696 minutes; m/e: 458.21, MS (ES+): 459.21.

Compound 158: 5-(2,5-Dimethoxy-phenyl)-4-[(4-methyl-3-pyridin-3-yl-phenyl)-hydrazono]-2,4-dihydro-pyrazol-3-one HPLC ($R_t$): 1.060 minutes; m/e: 415.49, MS (ES+): 416.49.

Compound 159: 5-(2,5-Dimethoxy-phenyl)-4-[(4'-hydroxymethyl-6-methyl-biphenyl-3-yl)-hydrazono]-2,4-dihydro-pyrazol-3-one HPLC ($R_t$): 1.351 minutes; m/e: 444.33, MS (ES+): 445.33.

Compound 160: 5-(2,5-Dimethoxy-phenyl)-4-[(3',4',5'-trimethoxy-6-methyl-biphenyl-3-yl)-hydrazono]-2,4-dihydro-pyrazol-3-one HPLC ($R_t$): 1.501 minutes; m/e: 504.38, MS (ES+): 505.38.

Compound 161: 4-[(6-Methyl-4'-phenoxy-biphenyl-3-yl)-hydrazono]-5-(3,4,5-trimethoxy-phenyl)-2,4-dihydro-pyrazol-3-one HPLC ($R_t$): 1.890 minutes; m/e: 536.32, MS (ES+): 537.32.

Compound 162: 4-[(3'-Ethoxy-6-methyl-biphenyl-3-yl)-hydrazono]-5-(3,4,5-trimethoxy-phenyl)-2,4-dihydro-pyrazol-3-one HPLC ($R_t$): 1.761 minutes; m/e: 488.32, MS (ES+): 489.32.

EXAMPLE 13

Compounds 163–202 were prepared by following the methods as described herein. The characterization data for these compounds is summarized in Table 5 below. Compound numbers correspond to the compound numbers listed in table 1.

TABLE 5

Characterization Data for Compounds 163–202

| Compound No. | [M + H]⁺ | $R_t$ (min.) |
|---|---|---|
| 163 | 445.36 | 1.40 |
| 164 | 416.29 | 1.09 |
| 165 | 505.30 | 1.56 |
| 166 | 507.40 | 1.87 |
| 167 | 421.24 | 1.65 |
| 168 | 472.30 | 1.40 |
| 169 | 459.36 | 1.75 |
| 170 | 416.30 | 1.11 |
| 171 | 405.25 | 1.58 |
| 172 | 421.29 | 1.64 |
| 173 | 459.33 | 1.76 |
| 174 | 416.31 | 1.09 |
| 175 | 457.29 | 1.54 |
| 176 | 451.27 | 1.65 |
| 177 | 489.33 | 1.75 |
| 178 | 446.31 | 1.09 |
| 179 | 535.35 | 1.52 |
| 180 | 435.30 | 1.57 |
| 181 | 500.39 | 1.30 |
| 182 | 577.40 | 1.90 |
| 183 | 491.31 | 1.74 |
| 184 | 542.41 | 1.49 |
| 185 | 529.41 | 1.79 |
| 186 | 529.36 | 1.81 |
| 187 | 515.40 | 1.50 |
| 188 | 529.35 | 1.69 |
| 189 | 575.43 | 1.64 |
| 190 | 475.35 | 1.67 |
| 191 | 500.35 | 1.27 |
| 192 | 577.43 | 1.91 |
| 193 | 542.38 | 1.48 |
| 194 | 529.38 | 1.78 |
| 195 | 529.36 | 1.67 |
| 196 | 545.41 | 1.61 |
| 197 | 527.39 | 1.62 |
| 198 | 575.42 | 1.62 |
| 199 | 431.29 | 1.58 |
| 200 | 487.36 | 1.46 |
| 201 | 475.33 | 1.37 |
| 202 | 487.34 | 1.53 |

While we have hereinbefore presented a number of embodiments of this invention, it is apparent that our basic construction can be altered to provide other embodiments which utilize the compounds and methods of this invention. Therefore, it will be appreciated that the scope of this invention is to be defined by the appended claims rather than by the specific embodiments which have been represented by way of example.

What is claimed is:

1. A compound of formula I:

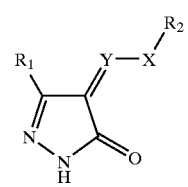

I or a pharmaceutically acceptable derivative or prodrug thereof, wherein:

$R_1$ is selected from carbocyclyl; heterocyclyl; aryl; heteroaryl; —CN; —C(O)R; —CO$_2$R; or —CON(R)$_2$; wherein said carbocyclyl, or heterocyclyl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, —NRS(O)$_2$R, =O, =S, =NN(R)$_2$, =N—OR, =NN(R)COR, =NNRCO$_2$R, =NNRSO$_2$R, =N—CN, or =NR; and wherein said aryl or heteroaryl is substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, or —NRS(O)$_2$R, wherein when R$_1$ is aryl or heteroaryl, R$_1$ has at least one non-hydrogen substituent;

R$_2$ is selected from; -carbocyclyl; heterocyclyl; aryl; or heteroaryl; wherein said carbocyclyl, or heterocyclyl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, —NRS(O)$_2$R, =O, =S, =NN(R)$_2$, =N—OR, =NN(R)COR, =NNRCO$_2$R, =NNRSO$_2$R, =N—CN, or =NR; and wherein said aryl or heteroaryl is substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, or —NRS(O)$_2$R, wherein when R$_2$ is aryl or heteroaryl, R$_2$ has at least one non-hydrogen substituent;

X is O, S or —NH;

Y is CH;

each R is independently selected from H; alkyl; carbocyclyl; heterocyclyl; aryl; heteroaryl; or any two R groups taken together form a carbocyclyl, heterocyclyl, aryl or heteroaryl group; wherein said alkyl, carbocyclyl, or heterocyclyl is optionally substituted with one to four substituents independently selected from halo, —R', —OR', —SR', —NO$_2$, —CN, —N(R')$_2$, —NR'C(O)R', —NR'C(O)N(R')$_2$, —N(R')CO$_2$R', —CO$_2$R', —C(O)R', —C(O)N(R')$_2$, —S(O)$_2$R', —S(O)$_2$N(R')$_2$, —S(O)R', —N(R')S(O)$_2$R', =O, =S, =NN(R')$_2$, =N—OR', =NN(R')COR', =NN(R')CO$_2$R', =NN(R')SO$_2$R', =N—CN, or =NR'; and wherein said aryl or heteroaryl is optionally substituted with one to four substituents independently selected from halo, —R', —OR', —SR', —NO$_2$, —CN, —N(R')$_2$, —NR'C(O)R', —NR'C(O)N(R')$_2$, —N(R')CO$_2$R', —CO$_2$R', —C(O)R', —C(O)N(R')$_2$, —S(O)$_2$R', —S(O)$_2$N(R')$_2$, —S(O)R', or —N(R')S(O)$_2$R';

each R' is independently selected from H; alkyl; carbocyclyl; heterocyclyl; aryl; heteroaryl; or any two R' groups taken together form a carbocyclyl, heterocyclyl, aryl or heteroaryl group; wherein said alkyl, carbocyclyl, or heterocyclyl is optionally substituted with one to four substituents independently selected from halo, CF$_3$, —R", —OR", —SR", —NO$_2$, —CN, —N(R")$_2$, —NR"C(O)R", —NR"C(O)N(R")$_2$, —N(R")CO$_2$R", —CO$_2$R", —C(O)R", —C(O)N(R")$_2$, —S(O)$_2$R", —S(O)$_2$N(R")$_2$, —S(O)R", —N(R")S(O)$_2$R", =O, =S, =NN(R")$_2$, =N—OR", =NN(R")COR", =NN(R")CO$_2$R", =NN(R")SO$_2$R", =N—CN, or =NR"; and wherein said aryl or heteroaryl is optionally substituted with one to four substituents independently selected from halo, CF$_3$, —R", —OR", —SR", —NO$_2$, —CN, —N(R")$_2$, —NR"C(O)R", —NR"C(O)N(R")$_2$, —N(R")CO$_2$R", —CO$_2$R", —C(O)R", —C(O)N(R")$_2$, —S(O)$_2$R", —S(O)$_2$N(R")$_2$, —S(O)R", or —N(R")S(O)$_2$R"; and each R" is independently selected from H or alkyl.

2. A compound of formula I:

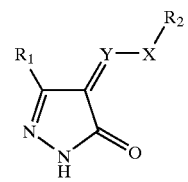

or a pharmaceutically acceptable derivative or prodrug thereof, wherein:

R$_1$ is selected from carbocyclyl; heterocyclyl; aryl; heteroaryl; or —CN; wherein said carbocyclyl or heterocyclyl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, —NRS(O)$_2$R, =O, =S, =NN(R)$_2$, =N—OR, =NN(R)COR, =NNRCO$_2$R, =NNRSO$_2$R, =N—CN, or =NR; and wherein said aryl or heteroaryl is substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, or —NRS(O)$_2$R, wherein when R$_1$ is aryl or heteroaryl, R$_1$ has at least one non-hydrogen substituent;

R$_2$ is selected from aryl; heteroaryl; carbocyclyl; or heterocyclyl; wherein said carbocyclyl or heterocyclyl is optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, —NRS(O)$_2$R, =O, =S, =NN(R)$_2$, =N—OR, =NN(R)COR, =NNRCO$_2$R, =NNRSO$_2$R, =N—CN, or =NR; and wherein said aryl or heteroaryl is substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, or —NRS(O)$_2$R, wherein when R$_2$ is aryl or heteroaryl, R$_2$ has at least one non-hydrogen substituent;

X is O, S or —NH;

Y is N;

each R is independently selected from H; alkyl; carbocyclyl; heterocyclyl; aryl; heteroaryl; or any two R groups taken together form a carbocyclyl, heterocyclyl, aryl or heteroaryl group; wherein said alkyl, carbocyclyl, or heterocyclyl is optionally substituted with one to four substituents independently selected from halo, —R', —OR', —SR', —NO$_2$, —CN, —N(R)$_2$, —NR'C(O)R', —NR'C(O)N(R')$_2$, —N(R')CO$_2$R', —CO$_2$R', —C(O)R', —C(O)N(R')$_2$, —S(O)$_2$R', —S(O)$_2$N(R')$_2$, —S(O)R', —N(R')S(O)$_2$R', =O, =S, =NN(R')$_2$, =N—OR', =NN(R')COR', =NN(R')CO$_2$R', =NN(R')SO$_2$R', =N—CN, or =NR'; and wherein said aryl or heteroaryl is optionally substituted with one to four substituents independently selected from halo, —R', —OR', —SR', —NO$_2$, —CN, —N(R')$_2$, —NR'C(O)R', —NR'C(O)N(R')$_2$, —N(R')CO$_2$R', —CO$_2$R', —C(O)R', —C(O)N(R')$_2$, —S(O)$_2$R', —S(O)$_2$N(R')$_2$, —S(O)R', or —N(R')S(O)$_2$R';

each R' is independently selected from H; alkyl; carbocyclyl; heterocyclyl; aryl; heteroaryl; or any two R' groups taken together form a carbocyclyl, heterocyclyl, aryl or heteroaryl group; wherein said alkyl, carbocyclyl, or heterocyclyl is optionally substituted with one to four substituents independently selected from halo, CF$_3$, —R", —OR", —SR", —NO$_2$, —CN, —N(R")$_2$, —NR"C(O)R", —NR"C(O)N(R")$_2$, —N(R")CO$_2$R", —CO$_2$R", —C(O)R", —C(O)N(R")$_2$, —S(O)$_2$R", —S(O)$_2$N(R")$_2$, —S(O)R", —N(R")S(O)$_2$R", =O, =S, =NN(R")$_2$, =N—OR", =NN(R")COR", =NN(R")CO$_2$R", =NN(R")SO$_2$R", =N—CN, or =NR"; and wherein said aryl or heteroaryl is optionally substituted with one to four substituents independently selected from halo, CF$_3$, —R", —OR", —SR", —NO$_2$, —CN, —N(R")$_2$, —NR"C(O)R", —NR"C(O)N(R")$_2$, —N(R")CO$_2$R", —CO$_2$R", —C(O)R", —C(O)N(R")$_2$, —S(O)$_2$R", —S(O)$_2$N(R")$_2$, —S(O)R", or —N(R")S(O)$_2$R"; and each R" is independently selected from H or alkyl;

with the proviso that:
i) when X is O and R$_1$ is heterocyclyl, aryl or heteroaryl, then R$_2$ is not heteroaryl or heterocyclyl; and
ii) R$_1$ excludes the following groups:

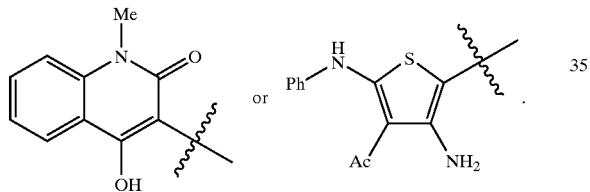

3. The compound according to claim 1 or 2, wherein R$_2$ is substituted phenyl.

4. The compound according to claim 3, wherein R$_1$ is substituted aryl or substituted heteroaryl.

5. The compound according to claim 4, wherein R$_1$ is substituted phenyl or substituted pyridyl.

6. A compound of formula I:

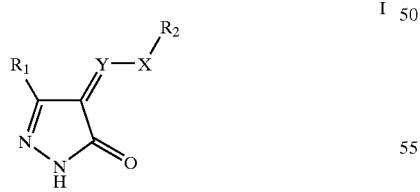

I or a pharmaceutically acceptable derivative or prodrug thereof,
wherein X is —NH;
Y is CH;
R$_1$ is phenyl or pyridyl wherein said phenyl and pyridyl are substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, or —NRS(O)$_2$R, wherein when R$_1$ is aryl or heteroaryl, R$_1$ has at least one non-hydrogen substituent;

R$_2$ is phenyl optionally substituted with one to four substituents independently selected from halo, —R, —OR, —SR, —NO$_2$, —CN, —N(R)$_2$, —NRC(O)R, —NRC(O)N(R)$_2$, —NRCO$_2$R, —CO$_2$R, —C(O)R, —C(O)N(R)$_2$, —S(O)$_2$R, —S(O)$_2$N(R)$_2$, —S(O)R, —NRS(O)$_2$R, =O, =S, =NN(R)$_2$, =N—OR, =NN(R)COR, =NNRCO$_2$R, =NNRSO$_2$R, =N—CN, or =NR;

each R is independently selected from H; alkyl; carbocyclyl; heterocyclyl; aryl; heteroaryl; or any two R groups taken together form a carbocyclyl, heterocyclyl, aryl or heteroaryl group; wherein said alkyl, carbocyclyl, or heterocyclyl is optionally substituted with one to four substituents independently selected from halo, —R', —OR', —SR', —NO$_2$, —CN, —N(R')$_2$, —NR'C(O)R', —NR'C(O)N(R')$_2$, —N(R')CO$_2$R', —CO$_2$R', —C(O)R', —C(O)N(R')$_2$, —S(O)$_2$R', —S(O)$_2$N(R'), —S(O)R', —N(R')S(O)$_2$R', =O, =S, =NN(R')$_2$, =N—OR', =NN(R')COR', =NN(R')CO$_2$R', =NN(R')SO$_2$R', =N—CN, or =NR'; and wherein said aryl or heteroaryl is optionally substituted with one to four substituents independently selected from halo, —R', —OR', —SR', —NO$_2$, —CN, —N(R')$_2$, —NR'C(O)R', —NR'C(O)N(R')$_2$, —N(R')CO$_2$R', —CO$_2$R', —C(O)R', —C(O)N(R')$_2$, —S(O)$_2$R', —S(O)$_2$N(R')$_2$, —S(O)R', or —N(R')S(O)$_2$R';

each R' is independently selected from H; alkyl; carbocyclyl; heterocyclyl; aryl; heteroaryl; or any two R' groups taken together form a carbocyclyl, heterocyclyl, aryl or heteroaryl group; wherein said alkyl, carbocyclyl, or heterocyclyl is optionally substituted with one to four substituents independently selected from halo, CF$_3$, —R", —OR", —SR", —NO$_2$, —CN, —N(R")$_2$, —NR"C(O)R", —NR"C(O)N(R")$_2$, —N(R")CO$_2$R", —CO$_2$R", —C(O)R", —C(O)N(R")$_2$, —S(O)$_2$R", —S(O)$_2$N(R")$_2$, —S(O)R", —N(R")S(O)$_2$R", =O, =S, =NN(R")$_2$, =N—OR", =NN(R")COR", =NN(R")CO$_2$R", =NN(R")SO$_2$R", =N—CN, or =NR"; and wherein said aryl or heteroaryl is optionally substituted with one to four substituents independently selected from halo, CF$_3$, —R", —OR", —SR", —NO$_2$, —CN, —N(R")$_2$, —NR"C(O)R", —NR"C(O)N(R")$_2$, —N(R")CO$_2$R", —CO$_2$R", —C(O)R", —C(O)N(R")$_2$, —S(O)$_2$R", —S(O)$_2$N(R")$_2$, —S(O)R", or —N(R")S(O)$_2$R"; and each R" is independently selected from H or alkyl.

7. The compound according to any one of claims 1–5, wherein X is O.

8. The compound according to claim 6, wherein:
R$_1$ is phenyl or pyridyl, wherein said phenyl or pyridyl is substituted with —R$_8$, —O-(alkyl optionally substituted with —CO$_2$R$_3$, —OR$_3$ or —N(R$_3$)$_2$), —O-aralkyl, —O-carbocyclyl, —CO$_2$R$_3$, —SO$_2$R$_3$, —SO$_2$N(R$_3$)$_2$, —CF$_3$, halo, —CN, or heterocyclyl optionally substituted with =O or alkyl;

R$_2$ is phenyl substituted with —NO$_2$, —N(R$_3$)$_2$, —OR$_3$, —O-aryl, —O-aralkyl, —O-heterocyclylalkyl, —O-(alkyl optionally substituted with R$^+$ or R$_{10}$), —O—CF$_3$, —CF$_3$, halo, —CN, —C(O)NH$_2$, —C(O)

N(R₁₀)₂, —CO₂R₃, —S(O)₂NH₂, —S(O)₂N(R₁₀)₂, —S(O)₂N(R₄)₂, —S(O)₂R₁₀, R₃, R₄, —NR₃C(O)R₁₀, R₁₀, R⁺, —C(O)-aryl, or aryl optionally substituted with —NR"C(O)R", —N(R")₂, —CF₃, halo, —CN, —C(O)R", —OR", —O-aryl, or R₁₀;

each R₃ is independently selected from H or alkyl;

each R₄ is independently heteroaryl or heterocyclyl, wherein heterocyclyl is optionally substituted with =O, —CO₂R" or alkyl;

R₈ is alkyl substituted by —OR"; and each R₁₀ is independently alkyl optionally substituted with one or four substituents selected from the group consisting of —OR", —CO₂R", SO₂N(R")₂, —N(R")₂, NR"C(O)R" and CN.

9. A compound selected from the group consisting of:

TABLE 1

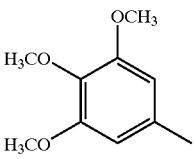

| Compound No. | Y | R₁ | R₂ |
|---|---|---|---|
| 13 | N | 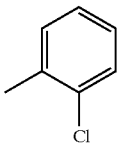 | 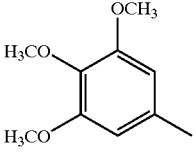 |
| 22 | N | 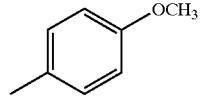 | 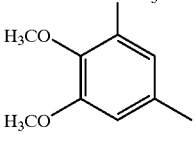 |
| 23 | N | 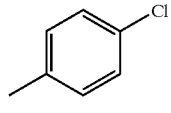 | 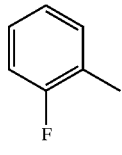 |
| 27 | N | 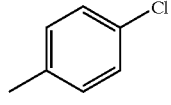 | 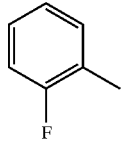 |
| 28 | N | 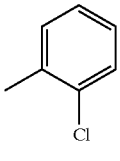 | 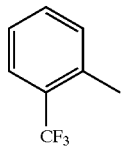 |
| 32 | N | 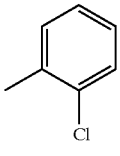 | |

TABLE 1-continued
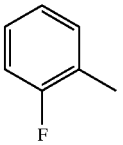
| Compound No. | Y | R₁ | R₂ |
|---|---|---|---|
| 33 | N | 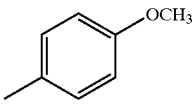 | 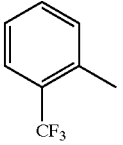 |
| 34 | N | 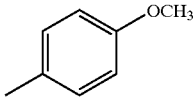 | 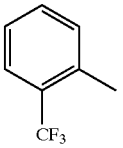 |
| 35 | N | 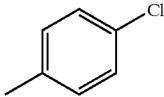 | 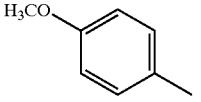 |
| 36 | N | 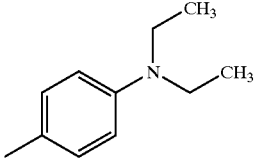 | 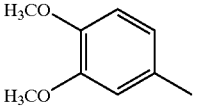 |
| 37 | N | 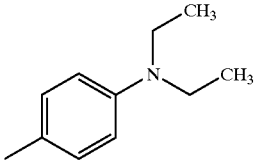 | 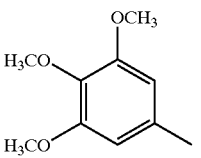 |
| 38 | N | 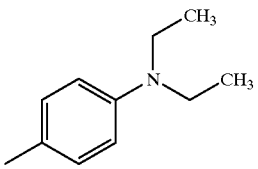 | 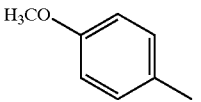 |
| 39 | N | 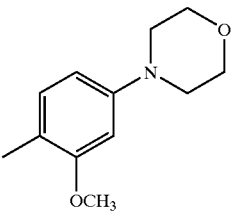 | 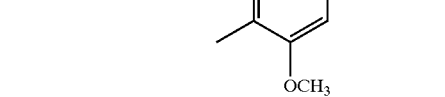 |

TABLE 1-continued
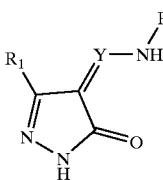
| Compound No. | Y | R₁ | R₂ |
|---|---|---|---|
| 40 | N | 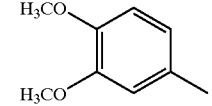 | 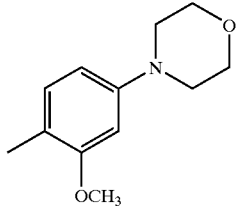 |
| 41 | N | 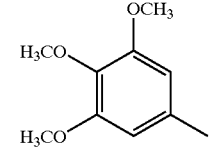 | 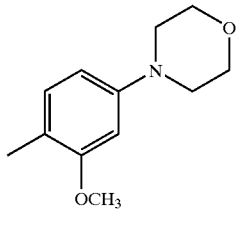 |
| 42 | N | 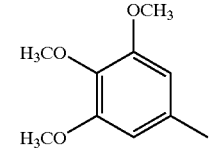 | 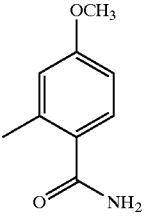 |
| 43 | N | 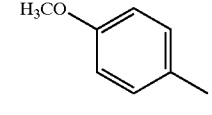 | 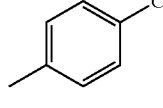 |
| 44 | N | 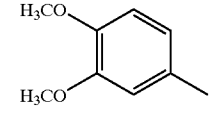 | 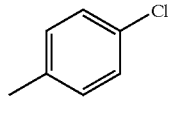 |
| 45 | N | 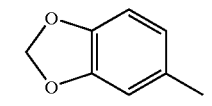 | 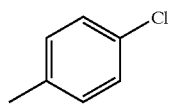 |
| 46 | N | 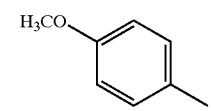 | 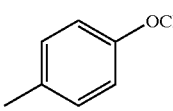 |
| 47 | N | 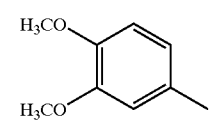 | 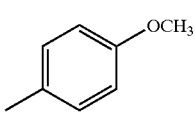 |

TABLE 1-continued
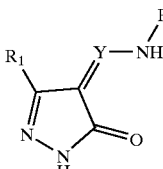
| Compound No. | Y | R₁ | R₂ |
|---|---|---|---|
| 48 | N | 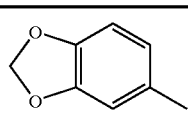 | 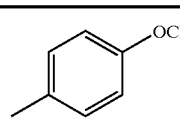 |
| 49 | N | 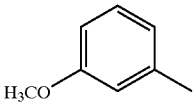 | 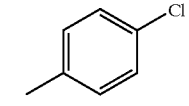 |
| 50 | N | 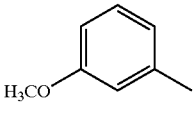 | 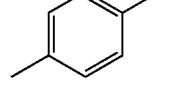 |
| 51 | N | 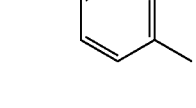 | 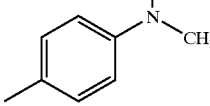 |
| 52 | N | 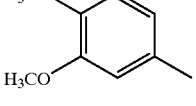 | 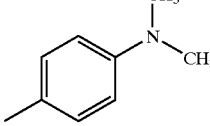 |
| 53 | N | 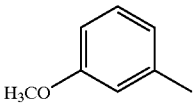 | 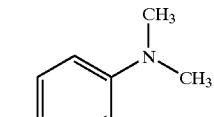 |
| 54 | N | 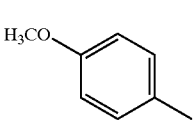 | 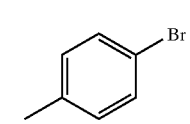 |
| 55 | N | 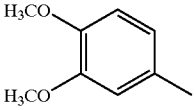 | 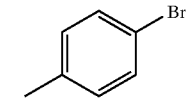 |
| 56 | N | 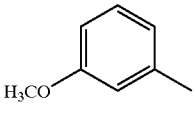 | 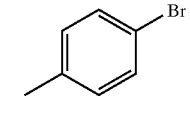 |
| 57 | N | 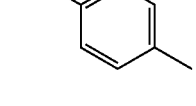 | 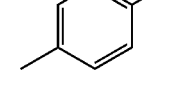 |

TABLE 1-continued

| Compound No. | Y | R₁ | R₂ |
|---|---|---|---|
| 58 | N | 3,4-dimethoxyphenyl | 4-cyanophenyl |
| 59 | N | 3-methoxyphenyl | 4-cyanophenyl |
| 60 | N | 4-methoxyphenyl | 4-morpholinophenyl |
| 61 | N | 3,4-dimethoxyphenyl | 4-morpholinophenyl |
| 62 | N | 3-methoxyphenyl | 4-morpholinophenyl |
| 63 | N | 4-methoxyphenyl | 4-(trifluoromethyl)phenyl |
| 64 | N | 3,4-dimethoxyphenyl | 4-(trifluoromethyl)phenyl |
| 65 | N | 3-methoxyphenyl | 4-(trifluoromethyl)phenyl |
| 66 | N | 4-methoxyphenyl | 3-(trifluoromethyl)phenyl |

TABLE 1-continued
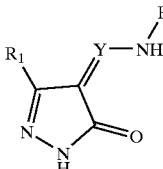
| Compound No. | Y | R₁ | R₂ |
|---|---|---|---|
| 67 | N | 3,4-(H₃CO)₂-C₆H₃- | 3-CF₃-C₆H₄- |
| 68 | N | 3-H₃CO-C₆H₄- | 3-CF₃-C₆H₄- |
| 69 | N | 4-H₃CO-C₆H₄- | 3-Cl-C₆H₄- |
| 70 | N | 3,4-(H₃CO)₂-C₆H₃- | 3-Cl-C₆H₄- |
| 71 | N | 3-H₃CO-C₆H₄- | 3-Cl-C₆H₄- |
| 72 | N | 4-H₃CO-C₆H₄- | 3-OCH₃-C₆H₄- |
| 73 | N | 3,4-(H₃CO)₂-C₆H₃- | 3-OCH₃-C₆H₄- |
| 74 | N | 3-H₃CO-C₆H₄- | 3-OCH₃-C₆H₄- |
| 75 | N | 4-NC-C₆H₄- | 4-Cl-C₆H₄- |
| 76 | N | 4-NC-C₆H₄- | 4-OCH₃-C₆H₄- |
| 77 | N | 4-H₃CO-C₆H₄- | 4-NO₂-C₆H₄- |

TABLE 1-continued
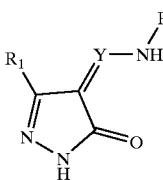
| Compound No. | Y | R₁ | R₂ |
|---|---|---|---|
| 78 | N | 3-methoxyphenyl | 4-nitrophenyl |
| 79 | N | 4-methoxyphenyl | 4-biphenyl |
| 80 | N | 3,4-dimethoxyphenyl | 4-biphenyl |
| 81 | N | 3-methoxyphenyl | 4-biphenyl |
| 82 | N | 4-methoxyphenyl | 4'-fluoro-4-biphenyl |
| 83 | N | 3,4-dimethoxyphenyl | 4'-fluoro-4-biphenyl |
| 84 | N | 3-methoxyphenyl | 4'-fluoro-4-biphenyl |
| 85 | N | 4-methoxyphenyl | 4-phenoxyphenyl |

TABLE 1-continued
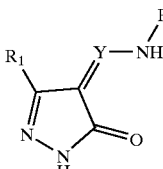
| Compound No. | Y | $R_1$ | $R_2$ |
|---|---|---|---|
| 86 | N | 3,4-dimethoxyphenyl | 4-phenoxyphenyl |
| 87 | N | 3-methoxyphenyl | 4-phenoxyphenyl |
| 88 | N | 4-methoxyphenyl | 3-phenoxyphenyl |
| 89 | N | 3,4-dimethoxyphenyl | 3-phenoxyphenyl |
| 90 | N | 3-methoxyphenyl | 3-phenoxyphenyl |
| 91 | CH | 4-methoxyphenyl | 4-phenoxyphenyl |
| 92 | CH | 3,4-dimethoxyphenyl | 3-benzyloxyphenyl |
| 93 | CH | 4-methoxyphenyl | 3-benzoylphenyl |
| 94 | CH | 3,4,5-trimethoxyphenyl | 2,3-dihydro-1,4-benzodioxin-6-yl |

TABLE 1-continued
| Compound No. | Y | R₁ | R₂ |
|---|---|---|---|
| 95 | CH | 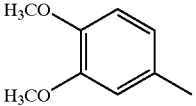 | 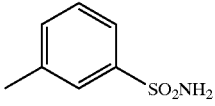 |
| 96 | CH | 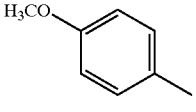 | 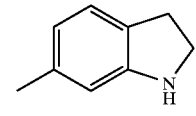 |
| 97 | CH | 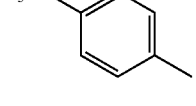 | 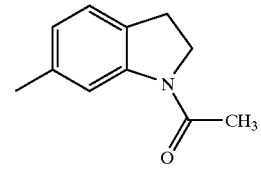 |
| 98 | CH | 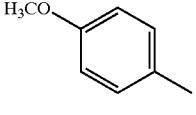 | 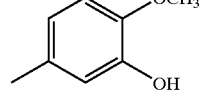 |
| 105 | N | 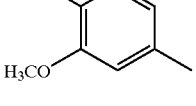 | 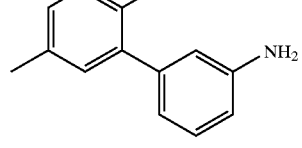 |
| 106 | N | 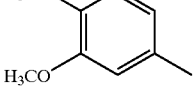 | 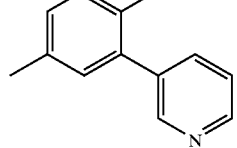 |
| 107 | N | 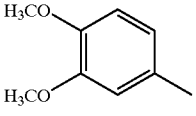 | 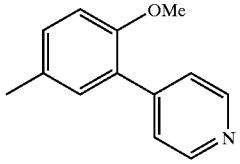 |
| 108 | N | 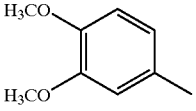 | 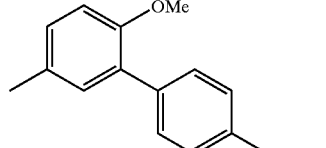 |

TABLE 1-continued

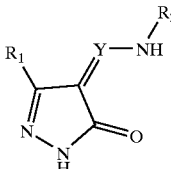

| Compound No. | Y | R₁ | R₂ |
|---|---|---|---|
| 109 | N | 3,4-dimethoxyphenyl | 2,3',4',5'-tetramethoxy-biphenyl-methyl |
| 110 | N | 3,4-dimethoxyphenyl | 2-methoxy-4'-(dimethylamino)biphenyl-methyl |
| 111 | N | 3,4-dimethoxyphenyl | 2,5-diethoxy-4-methyl-phenyl with morpholino |
| 112 | N | 3,4-dimethoxyphenyl | 2,3,5-trimethoxy-6-methylphenyl |
| 113 | N | 4-hydroxy-3-methoxyphenyl | 3-methoxy-4-methylphenyl with morpholino |
| 114 | N | 3,4-diethoxyphenyl | 4-(N,N-diethylamino)-methylphenyl |
| 115 | N | 3,4-diethoxyphenyl | 4-[N-ethyl-N-(2-hydroxyethyl)amino]methylphenyl |

TABLE 1-continued

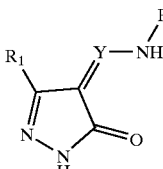

| Compound No. | Y | R₁ | R₂ |
|---|---|---|---|
| 116 | N | EtO—, EtO— phenyl | 4-(morpholin-4-yl)phenyl |
| 117 | N | PhCH₂O—, MeO— phenyl | 4-(N,N-diethylamino)phenyl |
| 118 | N | PhCH₂O—, MeO— phenyl | 4-[N-ethyl-N-(2-hydroxyethyl)amino]phenyl |
| 119 | N | PhCH₂O—, MeO— phenyl | 4-(morpholin-4-yl)phenyl |
| 120 | N | H₃CO—, H₃CO— phenyl | 2-{3-[N-methyl-N-(2-hydroxyethyl)amino]propoxy}-5-methylbiphenyl |
| 121 | N | H₃CO—, H₃CO— phenyl | 2-[3-(N,N-dimethylamino)propoxy]-5-methylbiphenyl |
| 122 | N | H₃CO—, H₃CO— phenyl | 2-[3-(morpholin-4-yl)propoxy]-5-methylbiphenyl |

TABLE 1-continued
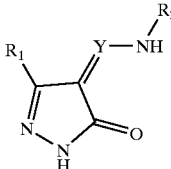
| Compound No. | Y | R₁ | R₂ |
|---|---|---|---|
| 123 | N | 3,4-(H₃CO)₂C₆H₃– | 2-OCH₃-5-(morpholin-4-yl)C₆H₃– |
| 124 | N | 3,4-(H₃CO)₂C₆H₃– | 2-OCH₃-5-(4-methylpiperazin-1-yl)C₆H₃– |
| 125 | N | 3,4,5-(H₃CO)₃C₆H₂– | 2-OCH₃-5-(morpholin-4-yl)C₆H₃– |
| 126 | N | 3-MeO-4-PhCH₂O-C₆H₃– | 2-OCH₃-5-(4-methylpiperazin-1-yl)C₆H₃– |
| 127 | N | 6-H₃CO-pyridin-3-yl | 4-Cl-C₆H₄– |
| 128 | N | 6-H₃CO-pyridin-3-yl | 4-OCH₃-C₆H₄– |
| 129 | N | 6-H₃CO-pyridin-3-yl | 3-Br-C₆H₄– |
| 132 | N | 3,4,5-(H₃CO)₃C₆H₂– | 4-(4-methylpiperazin-1-yl)C₆H₄– |

TABLE 1-continued
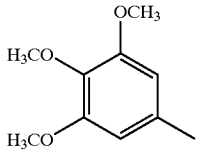
| Compound No. | Y | R₁ | R₂ |
|---|---|---|---|
| 133 | N | 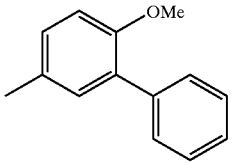 | 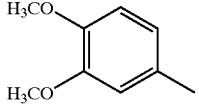 |
| 134 | N | 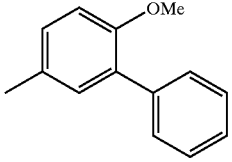 | 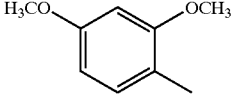 |
| 135 | N | 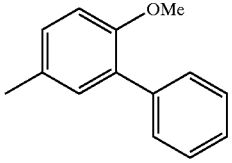 | 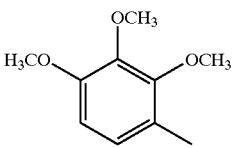 |
| 136 | N | 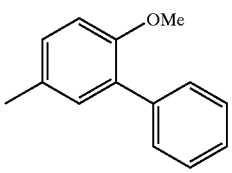 | 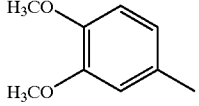 |
| 137 | N | 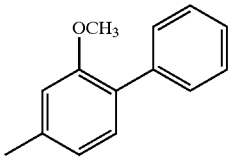 | 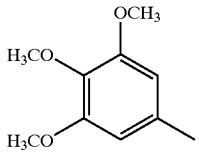 |
| 138 | N | 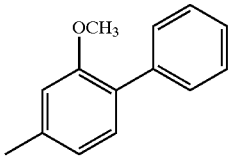 | 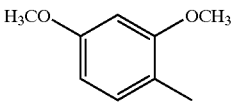 |
| 139 | N | 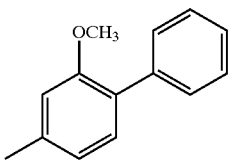 | |

TABLE 1-continued
| Compound No. | Y | R₁ | R₂ |
| --- | --- | --- | --- |
| 140 | N | 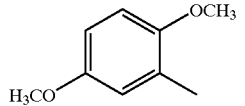 | 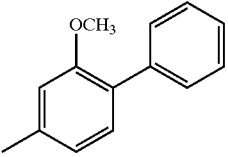 |
| 141 | N | 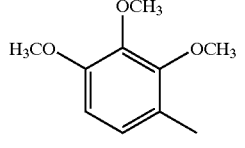 | 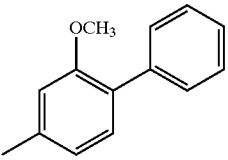 |
| 142 | N | 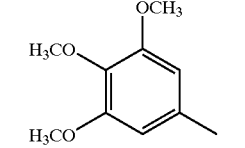 | 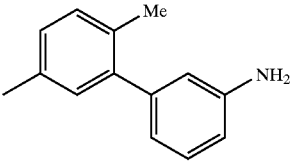 |
| 143 | N | 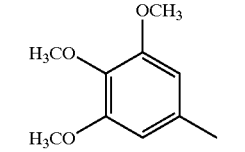 | 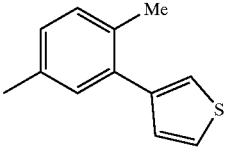 |
| 144 | N | 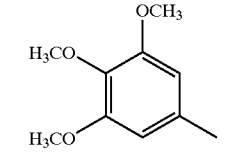 | 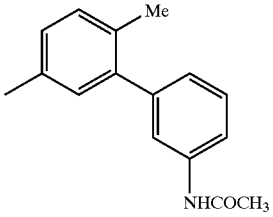 |
| 145 | N | 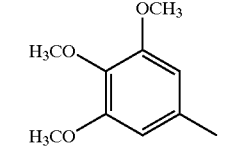 | 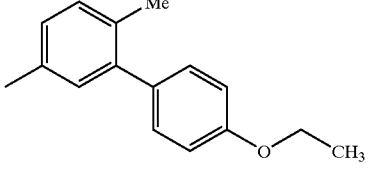 |
| 146 | N | 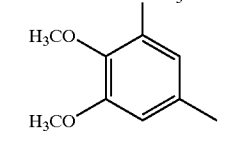 | 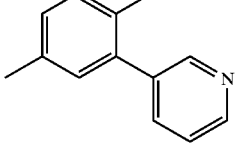 |

TABLE 1-continued
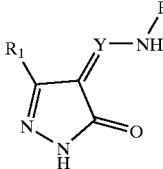
| Compound No. | Y | R₁ | R₂ |
| --- | --- | --- | --- |
| 147 | N | 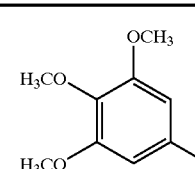 | 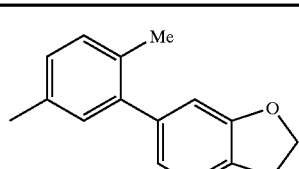 |
| 148 | N | 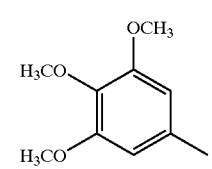 | 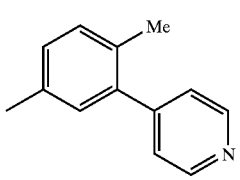 |
| 149 | N | 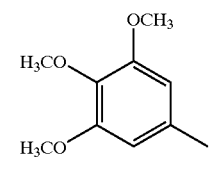 | 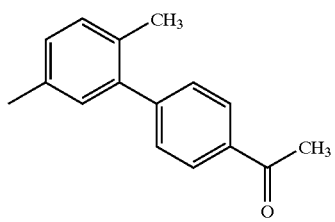 |
| 150 | N | 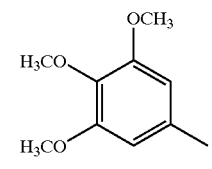 | 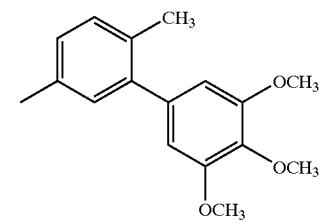 |
| 151 | N | 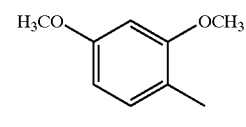 | 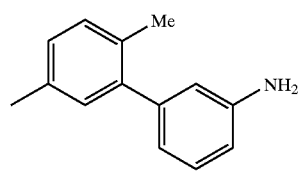 |
| 152 | N | 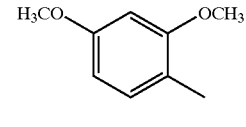 | 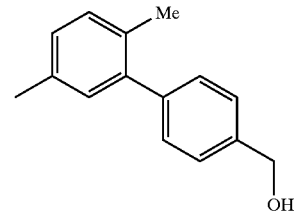 |

TABLE 1-continued

| Compound No. | Y | R₁ | R₂ |
|---|---|---|---|
| 153 | N | 2,5-dimethoxy-4-methylphenyl | 2-methyl-5-(benzo[1,3]dioxol-5-yl)phenyl (Me on C2, benzodioxole on C5) |
| 154 | N | 2,5-dimethoxy-4-methylphenyl | 2-methyl-5-(3,4,5-trimethoxyphenyl)phenyl |
| 155 | N | 2,5-dimethoxy-4-methylphenyl | 2-methyl-5-(4-phenoxyphenyl)phenyl |
| 156 | N | 2,5-dimethoxy-4-methylphenyl | 2-methyl-5-(3-acetamidophenyl)phenyl |
| 157 | N | 2,5-dimethoxy-4-methylphenyl | 2-methyl-5-(4-ethoxyphenyl)phenyl |
| 158 | N | 2,5-dimethoxy-4-methylphenyl | 2-methyl-5-(pyridin-3-yl)phenyl |

TABLE 1-continued
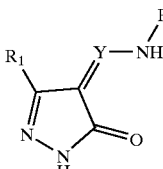
| Compound No. | Y | R₁ | R₂ |
|---|---|---|---|
| 159 | N | 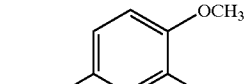 | 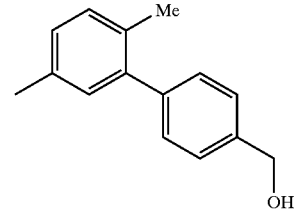 |
| 160 | N | 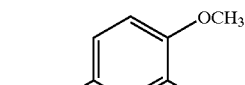 | 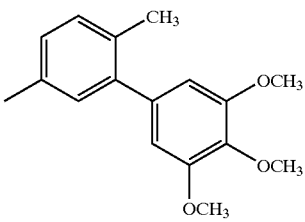 |
| 161 | N | 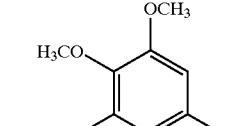 | 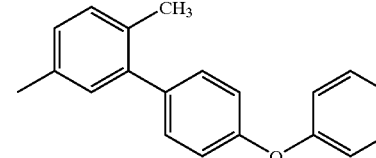 |
| 162 | N | 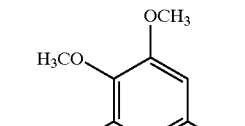 | 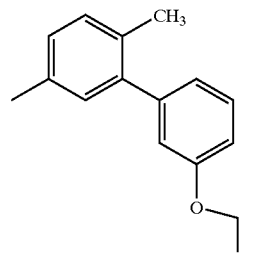 |
| 163 | N | 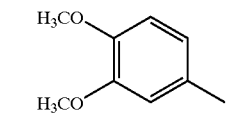 | 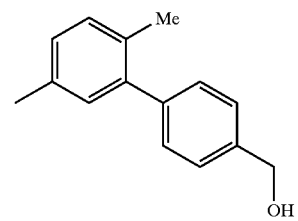 |
| 164 | N | 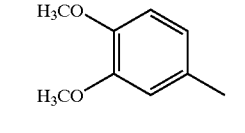 | 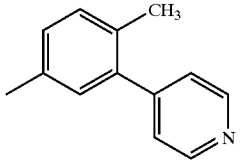 |

TABLE 1-continued
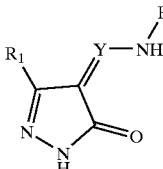
| Compound No. | Y | R₁ | R₂ |
|---|---|---|---|
| 165 | N | 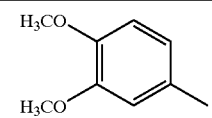 | 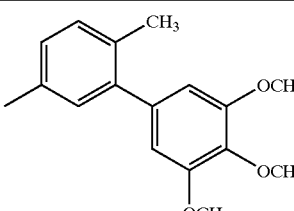 |
| 166 | N | 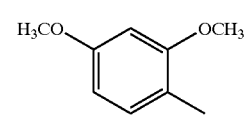 | 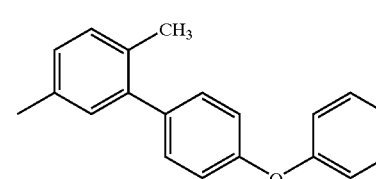 |
| 167 | N | 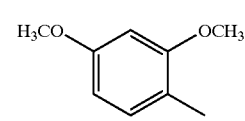 | 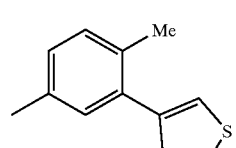 |
| 168 | N | 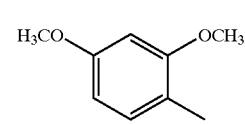 | 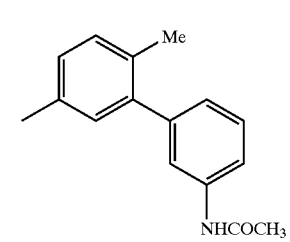 |
| 169 | N | 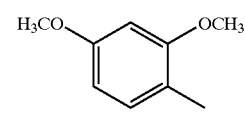 | 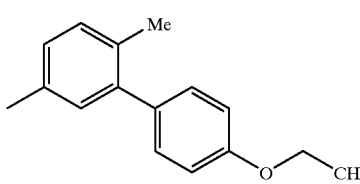 |
| 170 | N | 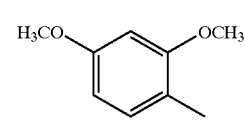 | 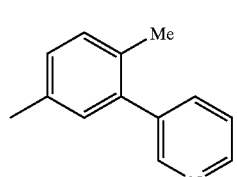 |
| 171 | N | 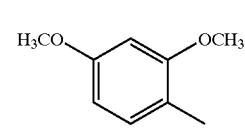 | 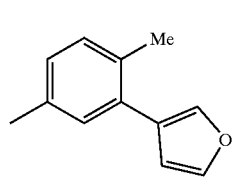 |

TABLE 1-continued
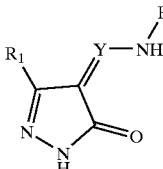
| Compound No. | Y | R₁ | R₂ |
|---|---|---|---|
| 172 | N | 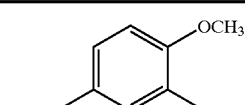 | 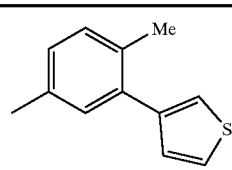 |
| 173 | N | 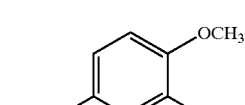 | 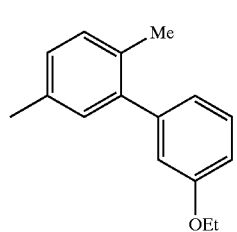 |
| 174 | N | 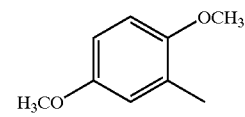 | 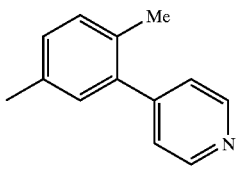 |
| 175 | N | 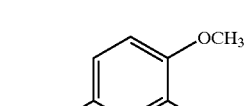 | 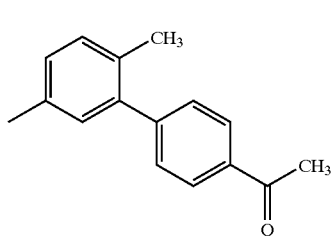 |
| 176 | N | 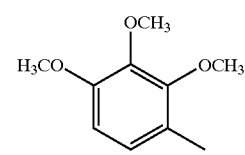 | 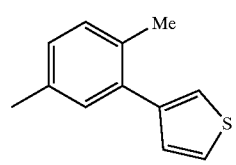 |
| 177 | N | 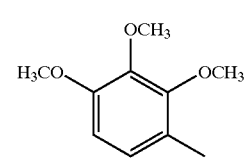 | 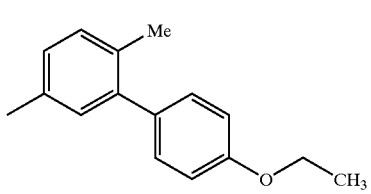 |
| 178 | N | 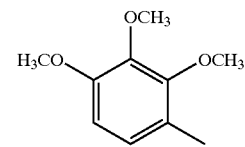 | 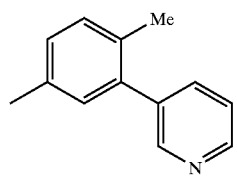 |

TABLE 1-continued
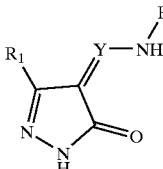
| Compound No. | Y | R₁ | R₂ |
|---|---|---|---|
| 179 | N | 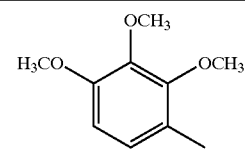 | 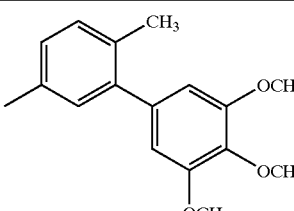 |
| 180 | N | 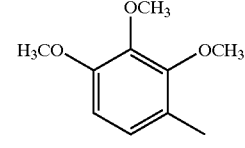 | 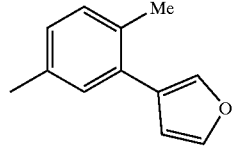 |
| 181 | N | 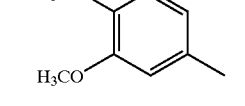 | 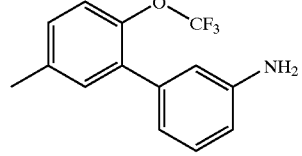 |
| 182 | N | 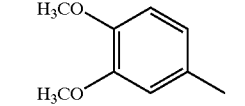 | 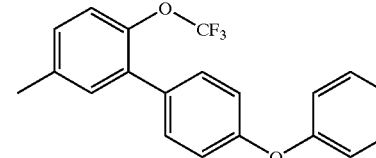 |
| 183 | N | 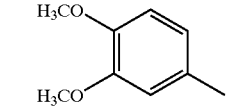 | 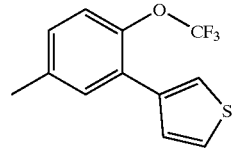 |
| 184 | N | 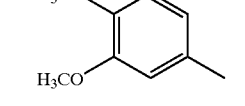 | 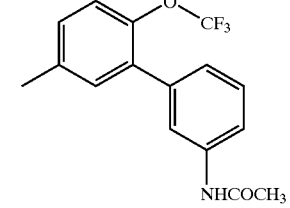 |
| 185 | N | 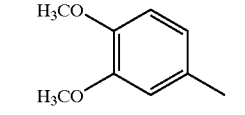 | 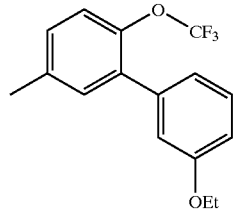 |

TABLE 1-continued

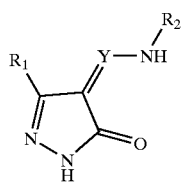

| Compound No. | Y | R₁ | R₂ |
|---|---|---|---|
| 186 | N | 3,4-dimethoxyphenyl | 2-(trifluoromethoxy)-5-methyl-4'-ethoxybiphenyl |
| 187 | N | 3,4-dimethoxyphenyl | 2-(trifluoromethoxy)-5-methyl-4'-(hydroxymethyl)biphenyl |
| 188 | N | 3,4-dimethoxyphenyl | 2-(trifluoromethoxy)-5-methyl-3',4'-(methylenedioxy)biphenyl |
| 189 | N | 3,4-dimethoxyphenyl | 2-(trifluoromethoxy)-5-methyl-3',4',5'-trimethoxybiphenyl |
| 190 | N | 3,4-dimethoxyphenyl | 2-(trifluoromethoxy)-5-methyl-2-(furan-3-yl)phenyl |
| 191 | N | 2,4-dimethoxy-6-methylphenyl | 2-(trifluoromethoxy)-5-methyl-3'-aminobiphenyl |
| 192 | N | 2,4-dimethoxy-6-methylphenyl | 2-(trifluoromethoxy)-5-methyl-4'-phenoxybiphenyl |

TABLE 1-continued
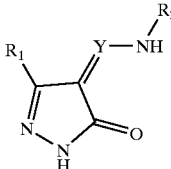
| Compound No. | Y | R₁ | R₂ |
| --- | --- | --- | --- |
| 193 | N | 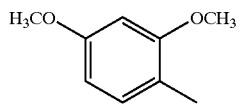 | 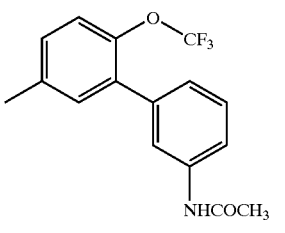 |
| 194 | N | 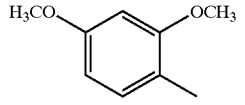 | 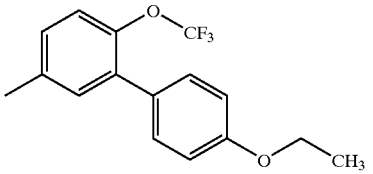 |
| 195 | N | 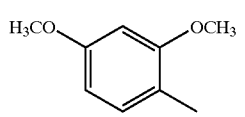 | 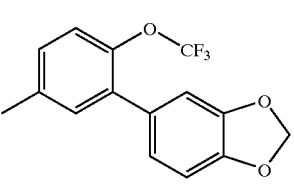 |
| 196 | N | 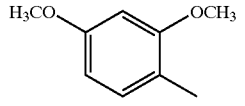 | 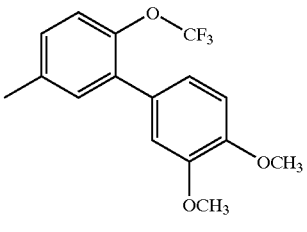 |
| 197 | N | 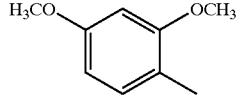 | 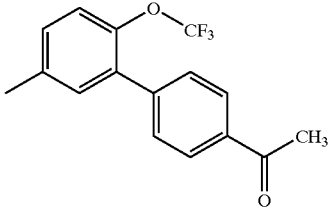 |
| 198 | N | 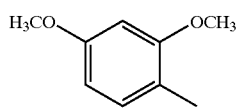 | 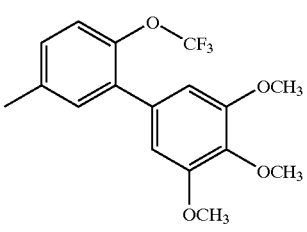 |

TABLE 1-continued
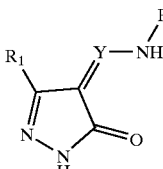
| Compound No. | Y | R₁ | R₂ |
|---|---|---|---|
| 199 | N | 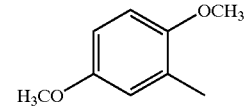 | 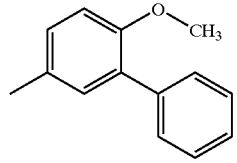 |
| 200 | N | 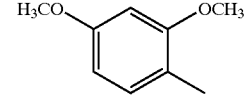 | 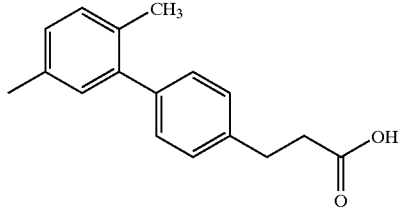 |
| 201 | N | 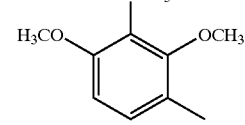 | 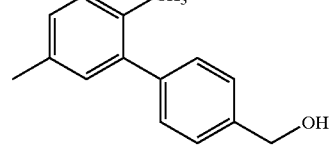 |
| 202 | N | 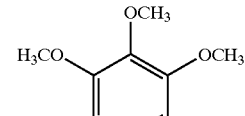 | 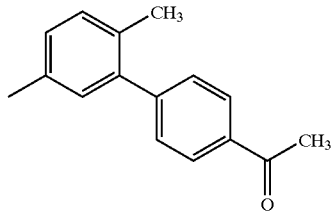 |
| 203 | N | 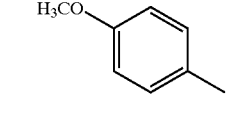 | 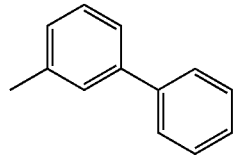 |
| 204 | N | 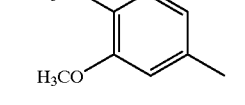 | 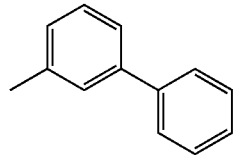 |
| 205 | N | 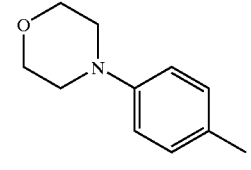 | 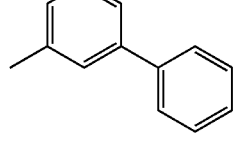 |

TABLE 1-continued
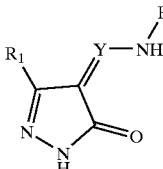
| Compound No. | Y | R₁ | R₂ |
|---|---|---|---|
| 206 | N | 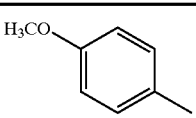 | 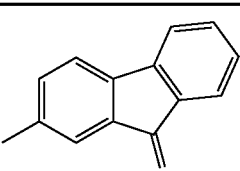 |
| 207 | N | 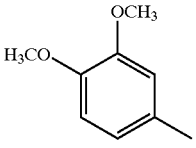 | 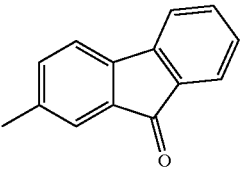 |
| 208 | N | 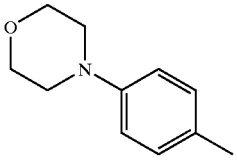 | 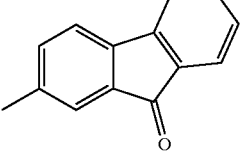 |
| 209 | N | 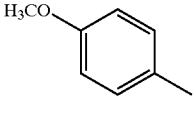 | 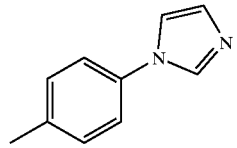 |
| 210 | N | 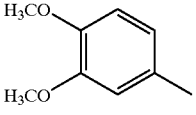 | 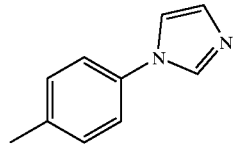 |
| 211 | N | 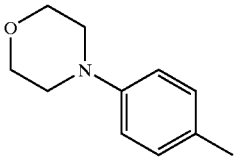 | 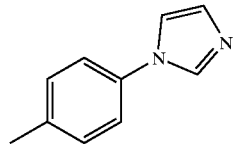 |
| 212 | N | 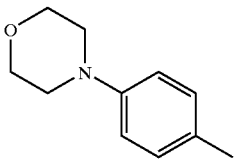 | 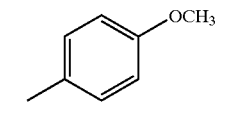 |
| 213 | N | 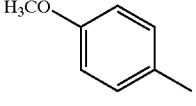 | 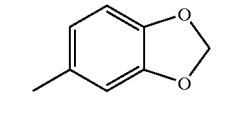 |

TABLE 1-continued
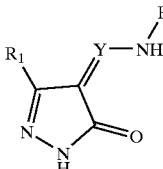
| Compound No. | Y | R₁ | R₂ |
|---|---|---|---|
| 214 | N | 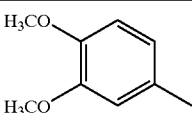 | 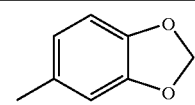 |
| 215 | N | 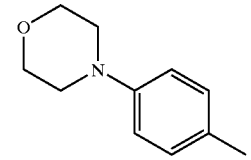 | 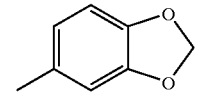 |
| 216 | N | 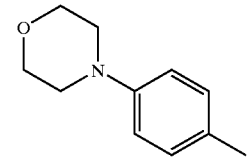 | 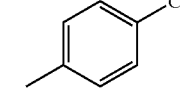 |
| 217 | N | 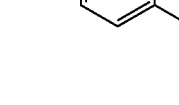 | 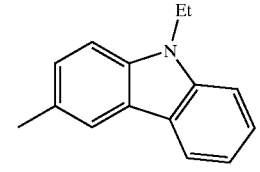 |
| 218 | N | 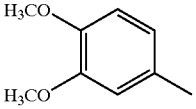 | 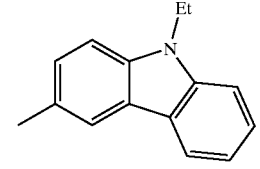 |
| 219 | N | 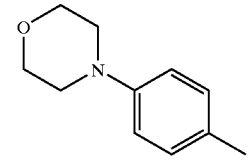 | 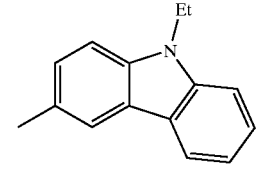 |
| 220 | N | 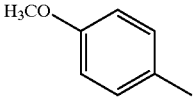 | 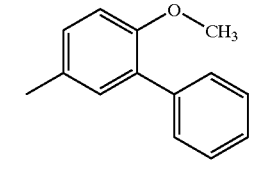 |
| 221 | N | 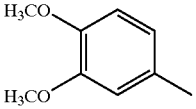 | 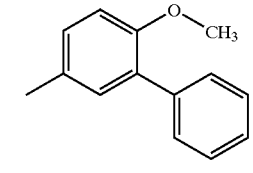 |

TABLE 1-continued
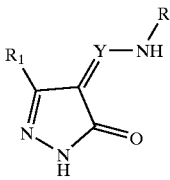
| Compound No. | Y | R₁ | R₂ |
|---|---|---|---|
| 222 | N | 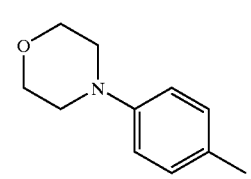 | 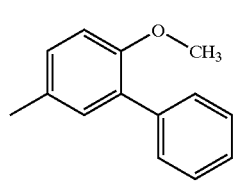 |
| 223 | N | 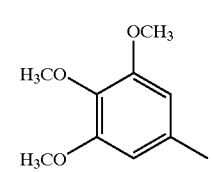 | 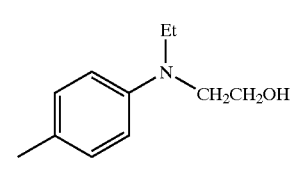 |
| 224 | CH | 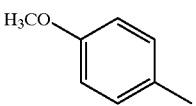 | 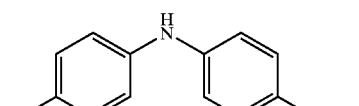 |
| 225 | N | 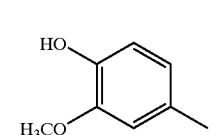 | 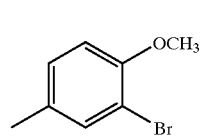 |
| 226 | N | 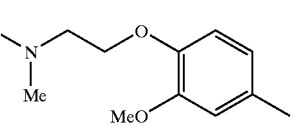 | 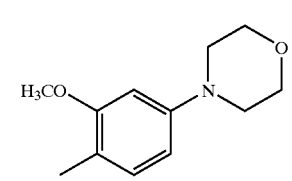 |
| 227 | CH | 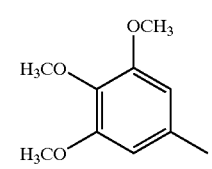 | 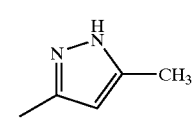 |
| 228 | N | 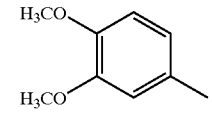 | 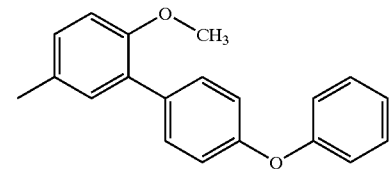 |
| 229 | N | 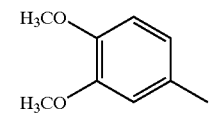 | 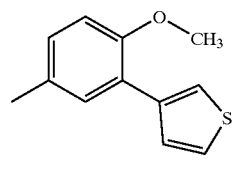 |

TABLE 1-continued

| Compound No. | Y | R₁ | R₂ |
|---|---|---|---|
| 230 | N | 3,4-dimethoxyphenyl | 2-methoxy-5-(3-ethoxyphenyl)phenyl |
| 231 | N | 3,4-dimethoxyphenyl | 2-methoxy-5-(4-ethoxyphenyl)phenyl |
| 232 | N | 3,4-dimethoxyphenyl | 2-methoxy-5-(furan-2-yl)phenyl |
| 233 | N | 3,4-dimethoxyphenyl | 2-methoxy-5-(3,4-dimethoxyphenyl)phenyl |
| 234 | N | 3,4-dimethoxyphenyl | 2-methoxy-5-(2-hydroxyphenyl)phenyl |
| 235 | N | 3,4-dimethoxyphenyl | 2-methoxy-5-(furan-3-yl)phenyl |

TABLE 1-continued
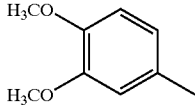
| Compound No. | Y | R₁ | R₂ |
|---|---|---|---|
| 236 | N | 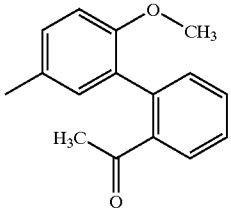 | 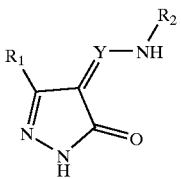 |
| 237 | N | 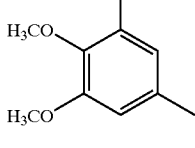 | 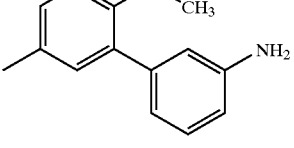 |
| 238 | N | 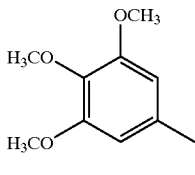 | 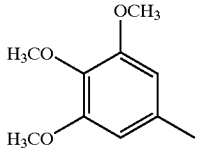 |
| 239 | N | 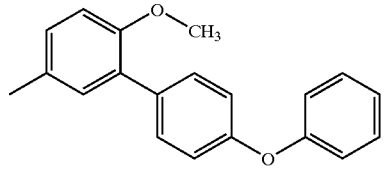 | 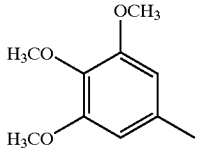 |
| 240 | N | 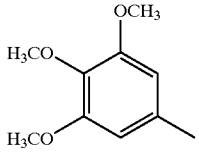 | 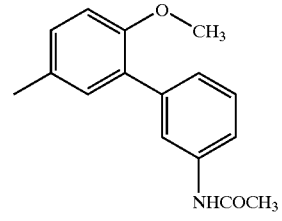 |
| 241 | N | 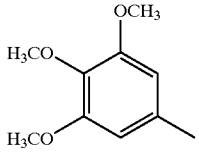 | 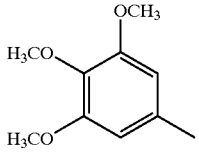 |

TABLE 1-continued
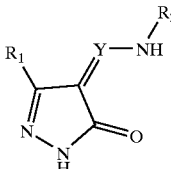
| Compound No. | Y | R₁ | R₂ |
|---|---|---|---|
| 242 | N | 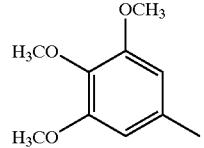 | 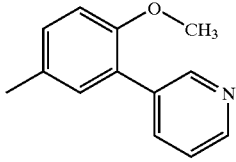 |
| 243 | N | 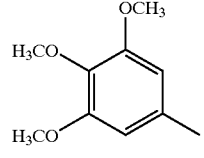 | 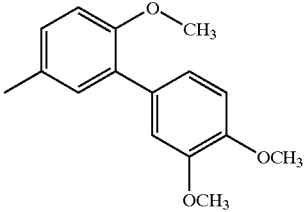 |
| 244 | N | 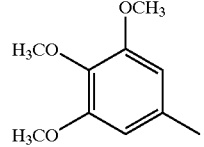 | 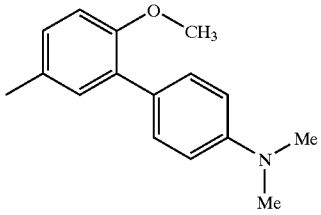 |
| 245 | N | 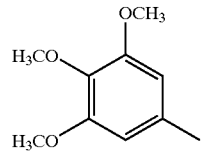 | 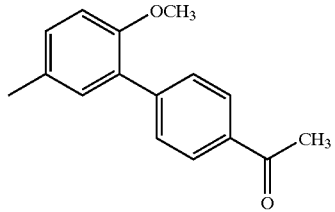 |
| 246 | N | 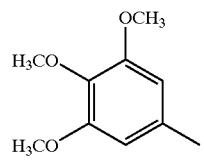 | 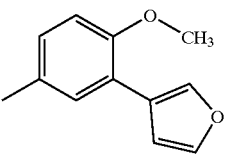 |
| 247 | N | 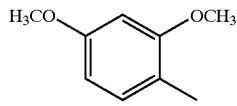 | 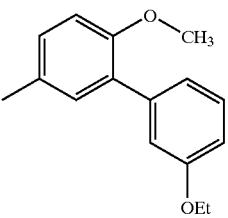 |

TABLE 1-continued
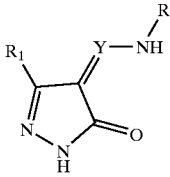
| Compound No. | Y | R₁ | R₂ |
| --- | --- | --- | --- |
| 248 | N | 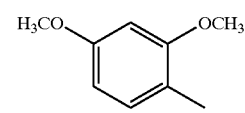 | 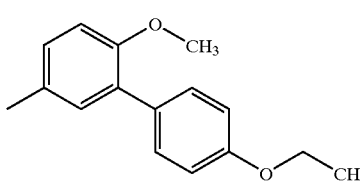 |
| 249 | N | 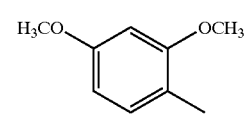 | 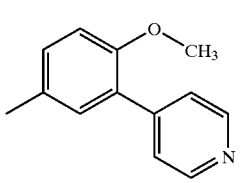 |
| 250 | N | 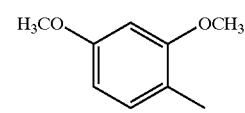 | 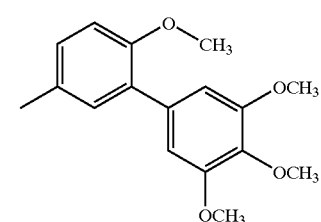 |
| 251 | N | 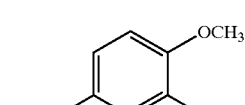 | 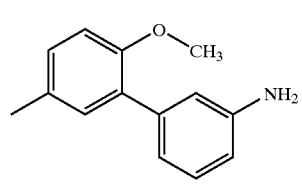 |
| 252 | N | 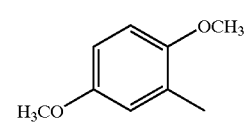 | 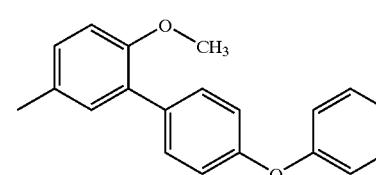 |
| 253 | N | 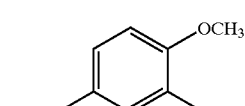 | 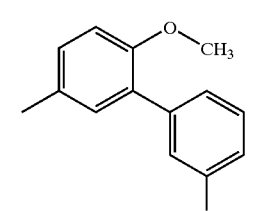 |

TABLE 1-continued
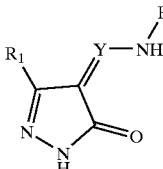
| Compound No. | Y | R₁ | R₂ |
| --- | --- | --- | --- |
| 254 | N | 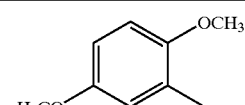 | 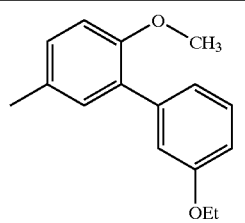 |
| 255 | N | 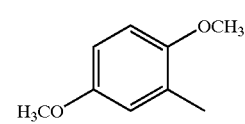 | 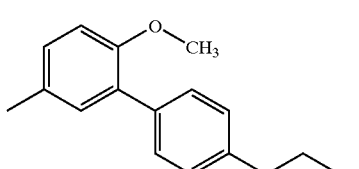 |
| 256 | N | 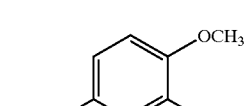 | 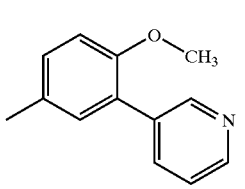 |
| 257 | N | 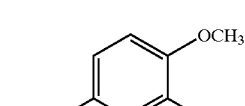 | 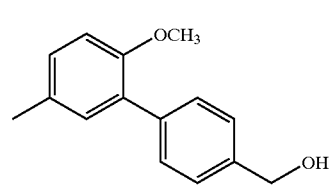 |
| 258 | N | 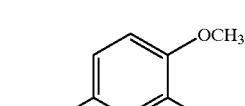 | 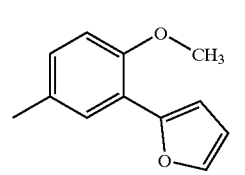 |
| 259 | N | 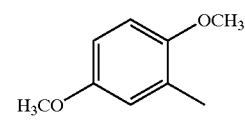 | 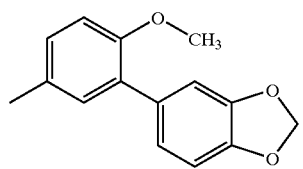 |
| 260 | N | 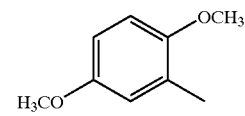 | 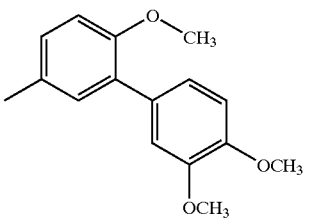 |

TABLE 1-continued
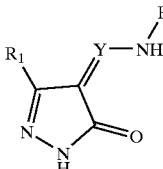
| Compound No. | Y | R₁ | R₂ |
|---|---|---|---|
| 261 | N | 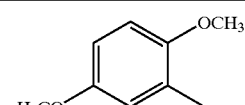 | 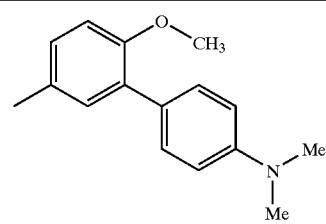 |
| 262 | N | 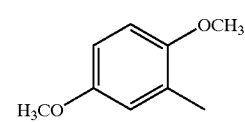 | 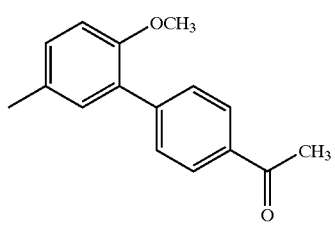 |
| 263 | N | 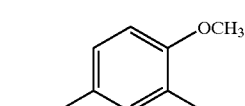 | 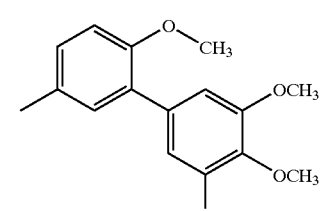 |
| 264 | N | 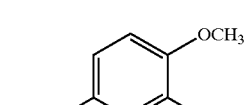 | 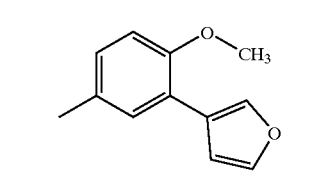 |
| 265 | N | 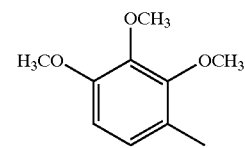 | 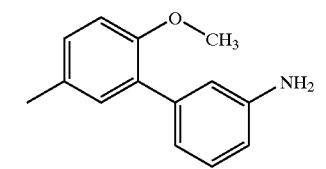 |
| 266 | N | 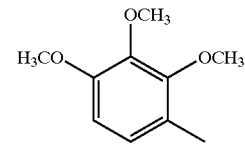 | 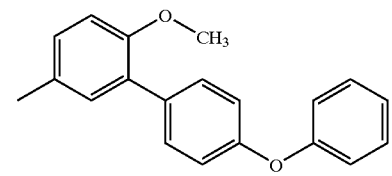 |
| 267 | N | 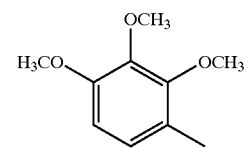 | 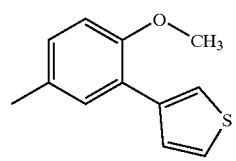 |

TABLE 1-continued
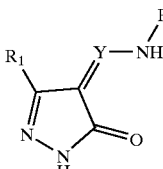
| Compound No. | Y | R₁ | R₂ |
|---|---|---|---|
| 268 | N | 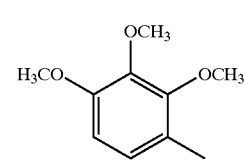 | 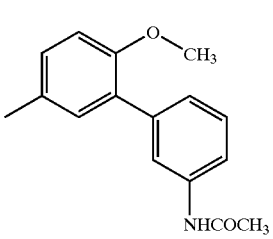 |
| 269 | N | 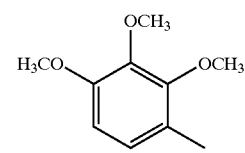 | 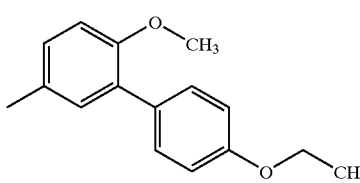 |
| 270 | N | 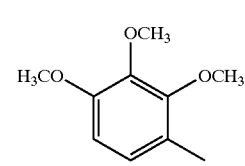 | 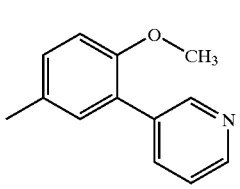 |
| 271 | N | 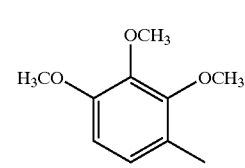 | 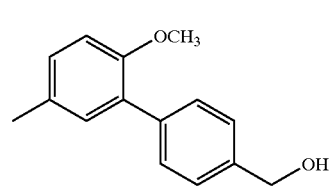 |
| 272 | N | 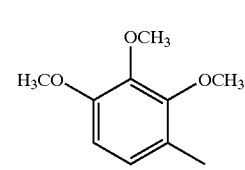 | 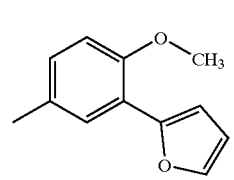 |
| 273 | N | 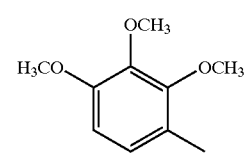 | 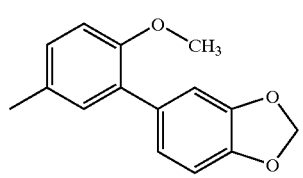 |
| 274 | N | 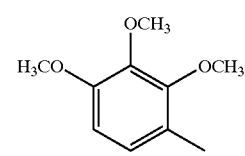 | 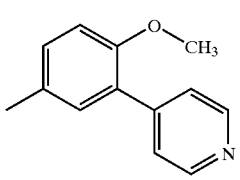 |

TABLE 1-continued
| Compound No. | Y | R₁ | R₂ |
| --- | --- | --- | --- |
| 275 | N | 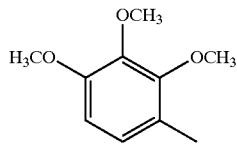 | 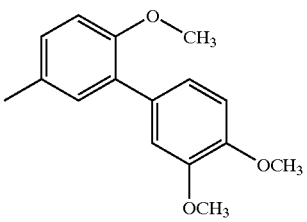 |
| 276 | N | 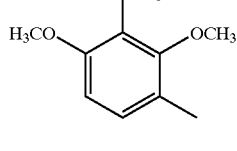 | 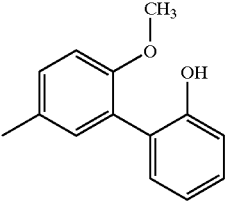 |
| 277 | N | 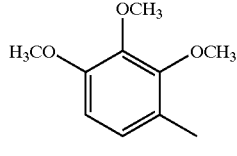 | 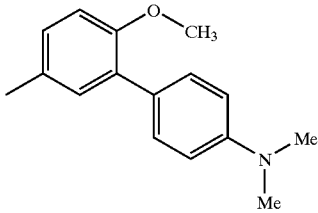 |
| 278 | N | 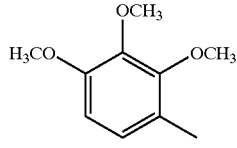 | 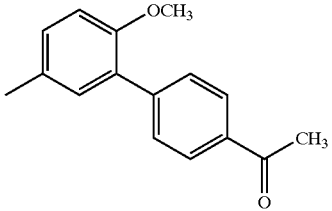 |
| 279 | N | 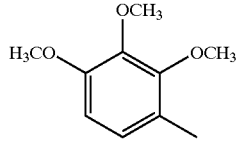 | 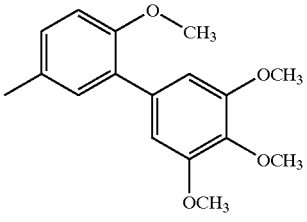 |
| 280 | N | 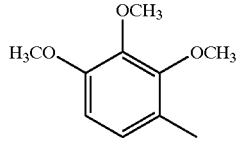 | 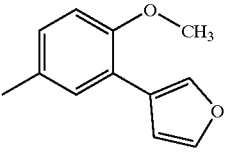 |

TABLE 1-continued
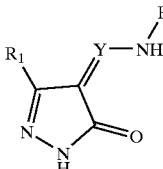
| Compound No. | Y | R₁ | R₂ |
| --- | --- | --- | --- |
| 281 | N | 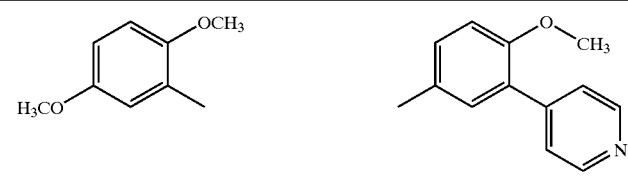 | 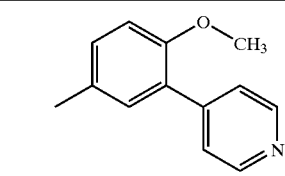 |
| 282 | N | 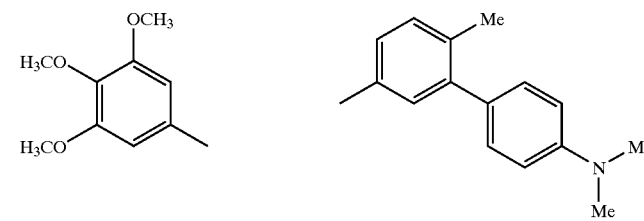 | 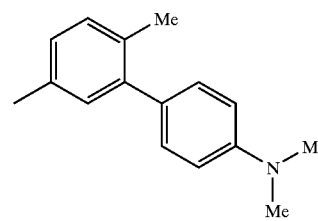 |
| 283 | N | 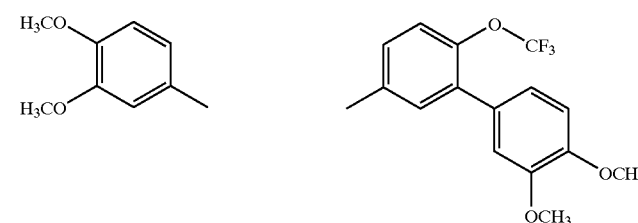 | 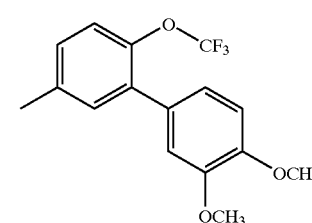 |
| 284 | N |  | 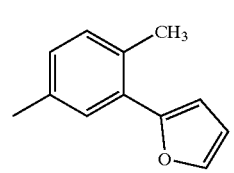 |
| 285 | N |  | 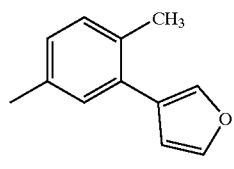 |
| 286 | N | 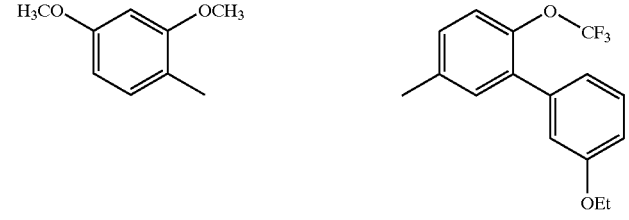 | 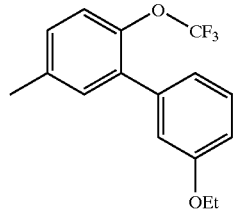 |
| 287 | N | 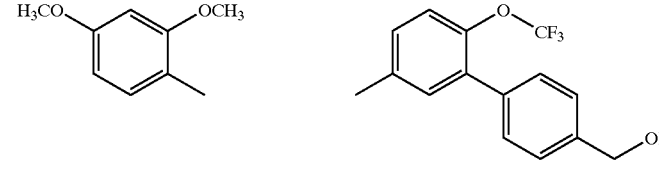 | 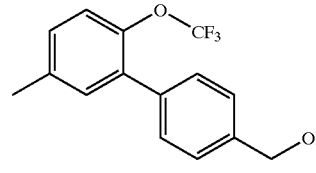 |

TABLE 1-continued
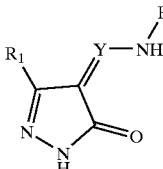
| Compound No. | Y | R₁ | R₂ |
|---|---|---|---|
| 288 | N | 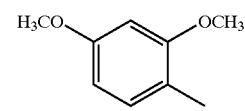 | 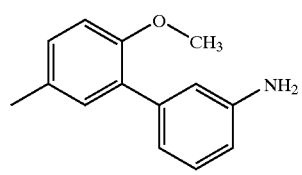 |
| 289 | N | 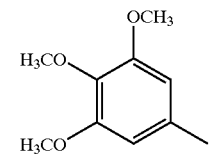 | 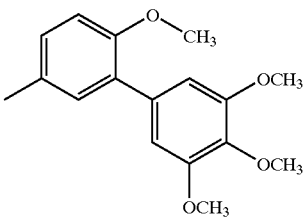 |
| 290 | N | 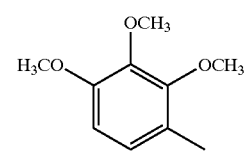 | and 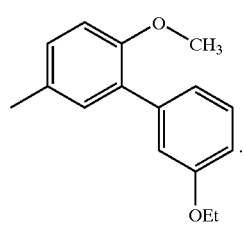 . |
10. A composition comprising a compound according to either of claim 1 or 2, and a pharmaceutically acceptable carrier, adjuvant, or vehicle.
* * * * *